(12) United States Patent
Osslund

(10) Patent No.: US 9,352,043 B2
(45) Date of Patent: May 31, 2016

(54) HIGH CONCENTRATION ANTIBODY FORMULATIONS

(75) Inventor: Timothy David Osslund, Camarillo, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 13/702,658

(22) PCT Filed: May 11, 2011

(86) PCT No.: PCT/US2011/036062
§ 371 (c)(1),
(2), (4) Date: Apr. 18, 2013

(87) PCT Pub. No.: WO2011/143307
PCT Pub. Date: Nov. 17, 2011

(65) Prior Publication Data
US 2013/0202620 A1    Aug. 8, 2013

Related U.S. Application Data

(60) Provisional application No. 61/334,986, filed on May 14, 2010.

(51) Int. Cl.
| | |
|---|---|
| A61K 39/00 | (2006.01) |
| A61K 39/395 | (2006.01) |
| C07K 1/00 | (2006.01) |
| C07K 16/00 | (2006.01) |
| C07K 16/18 | (2006.01) |
| A61K 47/24 | (2006.01) |
| A61K 9/00 | (2006.01) |
| A61K 47/12 | (2006.01) |
| C07K 16/22 | (2006.01) |

(52) U.S. Cl.
CPC .............. A61K 47/24 (2013.01); A61K 9/0019 (2013.01); A61K 39/39591 (2013.01); A61K 47/12 (2013.01); C07K 16/22 (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,331,647 A | 5/1982 | Goldenberg |
| 4,376,110 A | 3/1983 | David et al. |
| 4,411,993 A | 10/1983 | Gillis |
| 4,427,115 A | 1/1984 | Laipply |
| 4,543,439 A | 9/1985 | Frackelton, Jr. et al. |
| RE32,011 E | 10/1985 | Zimmerman et al. |
| 4,837,440 A | 6/1989 | Burtscher et al. |
| 4,902,614 A | 2/1990 | Wakabayashi et al. |
| 5,070,108 A | 12/1991 | Margolis |
| 5,145,684 A | 9/1992 | Liversidge et al. |
| 5,223,409 A | 6/1993 | Ladner et al. |
| 5,399,363 A | 3/1995 | Liversidge et al. |
| 5,453,492 A | 9/1995 | Butzow et al. |
| 5,466,468 A | 11/1995 | Schneider et al. |
| 5,543,158 A | 8/1996 | Gref et al. |
| 5,552,157 A | 9/1996 | Yagi et al. |
| 5,565,213 A | 10/1996 | Nakamori et al. |
| 5,567,434 A | 10/1996 | Szoka, Jr. |
| 5,571,714 A | 11/1996 | Dasch et al. |
| 5,627,052 A | 5/1997 | Schrader et al. |
| 5,641,515 A | 6/1997 | Ramtoola |
| 5,698,426 A | 12/1997 | Huse |
| 5,738,868 A | 4/1998 | Shinkarenko et al. |
| 5,780,263 A | 7/1998 | Hastings et al. |
| 5,795,587 A | 8/1998 | Gao et al. |
| 5,795,965 A | 8/1998 | Tsuchiya et al. |
| 5,811,238 A | 9/1998 | Stemmer et al. |
| 5,830,721 A | 11/1998 | Stemmer et al. |
| 5,837,458 A | 11/1998 | Minshull et al. |
| 5,877,397 A | 3/1999 | Lonberg et al. |
| 6,054,561 A | 4/2000 | Ring |
| 6,057,421 A | 5/2000 | Muller et al. |
| 6,117,911 A | 9/2000 | Grainger et al. |
| 6,133,426 A | 10/2000 | Gonzalez et al. |
| 6,180,370 B1 | 1/2001 | Queen et al. |
| 6,207,153 B1 | 3/2001 | Dan et al. |
| 6,395,511 B1 | 5/2002 | Brunkow et al. |
| 6,489,445 B1 | 12/2002 | Brunkow et al. |
| 6,495,736 B1 | 12/2002 | Brunkow et al. |
| 6,703,199 B1 | 3/2004 | Koide |
| 6,803,453 B1 | 10/2004 | Brunkow et al. |
| 6,806,055 B2 | 10/2004 | Berman et al. |
| 6,815,201 B2 | 11/2004 | Pinter |
| 6,818,748 B2 | 11/2004 | Fulton et al. |
| 6,875,432 B2 | 4/2005 | Liu et al. |

(Continued)

FOREIGN PATENT DOCUMENTS

| | | |
|---|---|---|
| JP | 4-141095 | 5/1992 |
| WO | WO-91/13152 | 9/1991 |

(Continued)

OTHER PUBLICATIONS

Paul, 1993, Fundamental Immunology, Raven Press, NY, pp. 292-295.*
Casset et al. (2003, Biochem Biophys Res Comm. 307:198-205).*
MacCallum et al. (1996, J Mol Biol. 262:732-745).*
Vajdos et al. (2002, J Mol Biol. 320(2):415-428).*
Holm et al. (2007, Mol Immunol. 44(6)1075-1084).*
Chen et al. (1999, J Mol Biol. 293:865-881).*
A diagram of a relevant part of the human genome (D64), citation in Appeal, European Patent No. 1133558, dated Apr. 15, 2010.

(Continued)

*Primary Examiner* — Elizabeth C Kemmerer
(74) *Attorney, Agent, or Firm* — Marshall, Gerstein & Borun LLP

(57) ABSTRACT

Discloses herein are high concentration antibody formulations comprising an anti-sclerostin immunoglobulin and an acetate salt and/or an acetate buffer and methods of use.

27 Claims, No Drawings

(56) References Cited

U.S. PATENT DOCUMENTS

| | | |
|---|---|---|
| 7,192,583 B2 | 3/2007 | Brunkow et al. |
| 7,226,902 B2 | 6/2007 | Winkler et al. |
| 7,381,409 B2 | 6/2008 | Winkler et al. |
| 7,572,899 B2 | 8/2009 | Brunkow et al. |
| 7,578,999 B2 | 8/2009 | Winkler et al. |
| 7,592,429 B2 | 9/2009 | Paszty et al. |
| 7,642,238 B2 | 1/2010 | Shaughnessy |
| 7,758,858 B2 | 7/2010 | Brunkow et al. |
| 7,868,134 B2 | 1/2011 | Winkler et al. |
| 7,872,106 B2 | 1/2011 | Paszty et al. |
| 8,178,099 B2 | 5/2012 | Ellies |
| 2003/0165410 A1 | 9/2003 | Taylor |
| 2003/0166247 A1 | 9/2003 | Brunkow et al. |
| 2003/0186915 A1 | 10/2003 | Pan et al. |
| 2003/0229041 A1 | 12/2003 | Sutherland et al. |
| 2004/0009535 A1 | 1/2004 | Brunkow et al. |
| 2004/0023356 A1 | 2/2004 | Krumlauf et al. |
| 2004/0058321 A1 | 3/2004 | Brunkow et al. |
| 2004/0141875 A1 | 7/2004 | Doshi |
| 2004/0146888 A1 | 7/2004 | Paszty et al. |
| 2004/0158045 A1 | 8/2004 | Brunkow et al. |
| 2005/0014650 A1 | 1/2005 | Seitz et al. |
| 2005/0085418 A1 | 4/2005 | Winkler et al. |
| 2005/0106683 A1 | 5/2005 | Winkler et al. |
| 2005/0238646 A1 | 10/2005 | Ledbetter et al. |
| 2006/0182740 A1 | 8/2006 | Yang et al. |
| 2006/0233801 A1 | 10/2006 | Brunkow et al. |
| 2007/0072797 A1 | 3/2007 | Robinson et al. |
| 2007/0110747 A1 | 5/2007 | Paszty et al. |
| 2007/0172479 A1 | 7/2007 | Warne et al. |
| 2007/0292444 A1 | 12/2007 | Krumlauf et al. |
| 2008/0160014 A1 | 7/2008 | Warne et al. |
| 2008/0182788 A1 | 7/2008 | Brunkow et al. |
| 2008/0234219 A1 | 9/2008 | Brunkow et al. |
| 2009/0074763 A1 | 3/2009 | Padhi et al. |
| 2009/0117118 A1 | 5/2009 | Winkler et al. |
| 2009/0304713 A1 | 12/2009 | Paszty et al. |
| 2010/0015665 A1 | 1/2010 | Latham et al. |
| 2010/0036091 A1 | 2/2010 | Robinson et al. |
| 2010/0151524 A1 | 6/2010 | Winkler et al. |
| 2011/0044978 A1 | 2/2011 | Ke et al. |
| 2011/0097342 A1 | 4/2011 | Paszty et al. |
| 2011/0150866 A1 | 6/2011 | Brunkow et al. |

FOREIGN PATENT DOCUMENTS

| | | |
|---|---|---|
| WO | WO-92/01047 | 1/1992 |
| WO | WO-92/02551 | 2/1992 |
| WO | WO-92/06693 | 4/1992 |
| WO | WO-95/30003 | 11/1995 |
| WO | WO-96/04375 | 2/1996 |
| WO | WO-98/21335 | 5/1998 |
| WO | WO-99/03996 | 1/1999 |
| WO | WO-99/06554 | 2/1999 |
| WO | WO-99/15556 | 4/1999 |
| WO | WO-00/32773 | 6/2000 |
| WO | WO-00/44777 | 8/2000 |
| WO | WO-00/75317 | 12/2000 |
| WO | WO-01/64885 | 9/2001 |
| WO | WO-01/92308 | 12/2001 |
| WO | WO-01/98491 | 12/2001 |
| WO | WO-02/24888 | 3/2002 |
| WO | WO-02/30463 | 4/2002 |
| WO | WO-03/050513 | 6/2003 |
| WO | WO-03/087763 | 10/2003 |
| WO | WO-03/106657 | 12/2003 |
| WO | WO-2004/082608 | 9/2004 |
| WO | WO-2004/094477 | 11/2004 |
| WO | WO-2004/098491 | 11/2004 |
| WO | WO-2005/003158 | 1/2005 |
| WO | WO-2005/014650 | 2/2005 |
| WO | WO-2005/115356 | 12/2005 |
| WO | WO-2006/015373 | 2/2006 |
| WO | WO-2006/065746 | 6/2006 |
| WO | WO-2006/102070 | 9/2006 |
| WO | WO-2006/119062 | 11/2006 |
| WO | WO-2006/119107 | 11/2006 |
| WO | WO-2007/080129 | 7/2007 |
| WO | WO-2008/061013 | 5/2008 |
| WO | WO-2008/092894 | 8/2008 |
| WO | WO-2008/115732 | 9/2008 |
| WO | WO-2008/133722 | 11/2008 |
| WO | WO-2009/039175 | 3/2009 |
| WO | WO-2009/047356 | 4/2009 |
| WO | WO-2009/056634 | 5/2009 |
| WO | WO-2009/079471 | 6/2009 |
| WO | WO-2009/131553 | 10/2009 |
| WO | WO-2009/149189 | 12/2009 |
| WO | WO-2010/100179 | 9/2010 |
| WO | WO-2010/100200 | 9/2010 |
| WO | WO-2010/115932 | 10/2010 |
| WO | WO-2010/130830 | 11/2010 |
| WO | WO-2012/028683 | 3/2012 |
| WO | WO-2012/058393 | 5/2012 |

OTHER PUBLICATIONS

Abbas et. al. (Eds.), Cellular and Molecular Immunology, Third Edition, Section II, p. 54 (1997).
Alberts et. al. (Eds.), Molecular Biology of the Cell, Third Edition, Chapter 23, p. 1212 (1994).
Albertsen et. al., A physical map and candidate genes in the BRCA1 region on chromosome 17q12-21. *Nat. Genet.*, 7:472-9 (1994).
Alting-Mees et. al., Monoclonal antibody expression libraries: A rapid alternative to hybridomas. *Strat. Molec. Biol.*, 3:1-9 (1990).
Alves et. al., Sclerosteosis: A marker of Dutch ancestry? *Rev. Bras. Genet.*, 4:825-34 (1982).
Andersson et. al., Molecular genetics and pathophysiology of 17β-hydroxysteriod dehydrogenase 3 deficiency. *J. Clin. Endocrinol. Metab.*, 81(1): 130-6 (1996).
Angal et. al., A single amino acid substitution abolishes the heterogeneity of chimeric mouse/human (IgG4) antibody. *Mol. Immunol.*, 30(1):105-8 (1993).
Annex EW6 to Declaration filed in connection with the European Patent EP 1133558 Opposition, Expert opinion of Prof. Dr. Edgar Wingender, dated Sep. 24, 2009.
Anonymous, Amgen presents denosumab and sclerostin antibody data at American Society for Bone and Mineral Research Annual Meeting. Amgen Media Press Release. <www.amgen.com/media/media_pr_detail.jsp?releaseID=907028> (2006).
Anonymous, UCB on track. UCB News <http://hugin.info/133973/R/1176122/233395.pdf> (2007).
Arnett et. al., Effect of pH on bone resorption by rat osteoclasts in vitro. *Endocrinol.*, 119(1): 119-124 (1986).
Attana Application Example, Opposition against European Patent No. 1721979 by Opponent: Novartis AG, dated Jun. 15, 2011.
Avsian-Kretchmer et. al., Comparative genomic analysis of the eight-membered ring cystine knot-containing bone morphogenetic protein antagonists. *Molec. Endocrinol.*, 18(1):1-12 (2004).
Babcook et. al., A novel strategy for generating monoclonal antibodies from single, isolated lymphocytes producing antibodies of defined specificities. *Proc. Natl. Acad. Sci. USA*, 93:7843-8 (1996).
Baines et. al., Purification of immunoglobulin G (IgG). *Meth. Molec. Biol.*, 10:79-104 (1992).
Balemans et. al., Extracellular regulation of BMP signaling in vertebrates: A cocktail of modulators. *Dev. Biol.*, 250:231-50 (2002).
Balemans et. al., Increased bone density in sclerosteosis is due to the deficiency of a novel secreted protein (SOST). *Hum. Mol. Genet.*, 10:537-43 (2001).
Balemans et. al., Localization of the gene for sclerosteosis to the van Buchem disease-gene region on chromosome 17q12-q21. *Am. J. Hum. Genet.*, 64:1661-9 (1999).
Balint et. al., Antibody engineering by parsimonious mutagenesis. *Gene*, 137(1):109-18 (1993).
Bateman et. al., Granulins: The structure and function of an emerging family of growth factors. *J. Endocrinol.*, 158: 145-51 (1998).
Baxevanis (Ed.) et. al., Bioinformatics: A practical guide to the analysis of genes and proteins, John Wiley & Sons, Inc. p. 234 (1998).
Beighton et. al., Heterozygous manifestations in the heritable disorders of the skeleton. *Pediatr. Radiol.*, 27: 397-401 (1997).

(56) References Cited

OTHER PUBLICATIONS

Beighton et. al., The clinical features of sclerosteosis. *Clin. Genet.*, 25:175-81 (1984).
Beighton et. al., The syndromic status of sclerosteosis and van Buchem disease. *Ann. Intern. Med.*, 84:393-7 (1976).
Bellows et. al., Parathyroid hormone reversibly suppresses the differentiation of osteoprogenitor cells in functional osteoblasts. *Endocrinol.*, 127(6): 3111-6 (1990).
Bendayan, Possibilities of false immunocytochemical results generated by the use of monoclonal antibodies: The example of the antiproinsulin antibody. *J. Histochem. Cytochem.*, 43(9):881-6 (1995).
Bendig, Humanization of rodent monoclonal antibodies by CDR grafting. *Methods*, 8:83-93 (1995).
Bergfeld et. al., Release of ATP from human erythrocytes in response to a brief period of hypoxia and hypercapnia. *Cardiovascular Res.*, 26: 40-7 (1992).
Berman et. al., The protein data bank. *Acta. Cryst.*, 58(1):899-907 (2002).
Bigger versions of Figures from Declaration of Professor Teresa Attwood, citation in Appeal, European Patent No. 1133558, dated Apr. 13, 2010.
Bird et. al., Single-chain antigen-binding proteins. *Science*, 242:423-6 (1988).
Birren et. al., EMBL sequence database accession No. AC003098.2, Nov. 14, 1997.
Bishop (Ed.), Guide to Human Genome Computing, Second Edition, Academic Press, Chapter 1: Introduction to human genome computer via the world wide web, pp. 1-14 (2003).
Black et. al., A somatic cell hybrid map of the long arm of human chromosome 17, containing the familial breast cancer ILocus (BRCAI). *Am. J. Hum. Genet.*, 52:702-10 (1993).
Blum et. al., Study plan for German students in the summer of 1998, University Bioinformatik lecture announcement (1998).
Boden et. al., Glucocorticoid-induced differentiation of fetal rat calvarial osteoblasts is mediated by bone morphogenetic protein-6. *Endocrinology*, 138(7):2820-8 (1997).
Boerner et. al., Production of antigen-specific human monoclonal antibodies from in vitro-primed human splenocytes. *J. Immunol.*, 147:86-95 (1991).
Bonaldo et. al., EMBL Sequence Database Accession No. Al113131, Sep. 4, 1998.
Bonaldo et. al., Normalization and subtraction: Two approaches to facilitate gene discovery. *Genome Res.*, 6(9):791-806 (1996).
Bondestam, Ligands & Signaling Components of the Transforming Growth Factor, Helsinki University Biomedical Dissertations (2002).
Bork et. al., Go hunting in sequence databases by watch out for the traps. *Trends Genet.*, 12: 425-7 (1996).
Bos et. al., Ras ongogenes in human cancer: A review. *Cancer Res.*, 49: 4682-9 (1989).
Bost et. al., Antibodies against a peptide sequence within the HIV envelope protein crossreacts with human interleukin-2. *Immunol. Invest.*, 17(6&7):577-86 (1988).
Bostrom et. al., Ligand and signaling components of the transforming growth factor β family. *J. Orth. Res.*, 13:357-67 (1995).
Bottcher et. al., NCBI Sequence database accession No. NM_004329, Aug. 2, 2009.
Bouffard et. al., A physical map of human chromosome 7: An integrated YAC contig map with average STS spacing of 79 kb. *Genome Res.*, 7: 673-92 (1997).
Bowie et. al., A method to identify protein sequences that fold into a known three-dimensional structure. *Science*, 253:164-70 (1991).
Bowie et. al., Deciphering the message in protein sequences: Tolerance to amino acid substitutions. *Science*, 247(4948):1306-10 (1990).
Bradley et. al., Modifying the mouse: Design and desire. *Bio/Technology*, 10:534-9 (1992).
Brandao-Burch et. al., Acidosis inhibits bone formation by osteoblasts in vitro by preventing mineralization. *Calcif. Tissue Int.*, 77: 167-74 (2005).
Brenner et. al., Population statistics of protein structures: Lessons from structural classifications. *Curr. Op. Struct. Biol.*, 7(3):369-76 (1997).
Brown, Hybridization analysis of DNA blots, *Current Protocols in Protein Science*, 13:A.4H.1-A.4H.9 (1990).
Brown, Hybridization analysis of DNA blots, *Current Protocols in Protein Science*, 2.10.1-2.10.16 (2000).
Bruggemann et. al., Production of human antibody repertoires in transgenic mice. *Curr. Opin. Biotechnol.*, 8:455-8 (1997).
Brunkow et. al., Bone dysplasia sclerosteosis results from loss of the SOST gene product, a novel cysteine knot-containing protein. *Am. J. Hum. Genet.*, 68:577-89 (2001).
Burton et. al., Human antibodies from combinatorial libraries. *Adv. Immunol.*, 57:191-280 (1994).
Butcher et. al., Increased salt concentration reversibly destabilizes p53 quaternary structure and sequence-specific DNA binding. *Biochem. J.*, 298: 513-6 (1994).
Byrne et. al., CD4+CD45RBHi T cell transfer induced colitis in mice is accompanied by osteopenia which is treatable with recombinant human osteoprotegerin. *Gut.*, 54:78-86 (2005).
Campbell et. al., Totipotency or multipotentiality of cultured cells: Applications and progress. *Theriogenology*, 47:63-72 (1997).
Caverzasio et. al., Characteristics and regulation of Pi transport in osteogenic cells for bone metabolism. *Kindey Int.*, 49: 975-80 (1996).
Chan et. al., A new paradigm in the treatment of osteoporosis: Wnt pathway proteins and their antagonists. *Curr. Opin. Invest. Drugs*, 8:293-8 (2007).
Chandran et. al., Recent trends in drug delivery systems: Liposomal drug delivery system—Preparation and characterization. *Indian J. Exp. Biol.*, 35(8):801-9 (1997).
Charlier et. al., A pore mutation in a novel KQT-like potassium channel gene in an idiopathic epilepsy family. *Nat. Genet.*, 18:53-5 (1998).
Chenu et. al., Glutamate receptors are expressed by bone cells and are involved in bone resorption. *Bone*, 22(4): 295-9 (1998).
Chou et. al., Empirical predication of protein conformation. *Ann. Rev. Biochem.*, 47:251-76 (1979).
Chou et. al., Prediction of the secondary structure of proteins from their amino acid sequence. *Adv. Enzymol. Relat. Areas Mol. Biol.*, 47:145-8 (1978).
Clark, Antibody humanization: A case of the 'Emperor's New Clothes'?. *Immunology Today*, 21(8):397-402 (2000).
Cogan et. al., NCBI Sequence Database Accession No. NM_033346, Jul. 19, 2005.
Collins, Identifying human disease genes by positional cloning. The Harvey Lectures, Series 86:149-64 (1992).
Collins, Positional cloning moves from perditional to traditional. *Nat. Genet.*, 9:347-50 (1995).
Colman, Effects of amino acid sequence changes on antibody-antigen interactions. *Biomolec. Res. Inst.*, 55:33-6 (1994).
Communication from the European Patent Office providing an "Observation by a Third Party according to Article 115 EPC" submitted in connection with the Opposition to European Patent No. 1 133 558, dated Dec. 3, 2008.
Cook et. al., Structural basis for a functional antagonist in the transforming growth factor β superfamily. *J. Biol. Chem.*, 280(48):40177-86 (2005).
Cormier, Markers of bone metabolism. *Curr. Opin. in Rheu.*, 7:243-8 (1995).
Couvreur et. al., Polyalkylcyanoacrylates as colloidal drug carriers. *Crit. Rev. Ther. Drug Carrier Syst.*, 5(1):1-20 (1988).
Craig et. al., Sclerostin binds and regulates the activity of cysteine rich protein 61. *Biochem. Biophys. Res. Commun.*, 293(1): 36-40 (2010).
Craig et. al., Sclerostin-erbB-3 interactions: Modulation of erbB-3 activity by sclerostin. *Biochem. Biophys. Res. Commun.*, 402: 421-4 (2010).
Crameri et. al., DNA shuffling of a family of genes from diverse species accelerates directed evolution. *Nature*, 391:288-91 (1998).
Dall'Acqua et. al., Antibody humanization by framework shuffling. *Methods*, 36(1):43-60 (2005).

(56) References Cited

OTHER PUBLICATIONS

Davies, et. al., Affinity improvement of single antibody VH domains: Residues in all three hypervariable regions affect antigen binding. *Immunotechnology*, 2(3): 169-79 (1996).
de Jong et. al., Evolution of the α-crystallin/small heat-shock protein family. *Mol. Biol. Evol.*, 10(1): 103-26 (1993).
Dean et. al., Matrix vesicles produced by osteoblast-like cells in culture become significantly enriched in proteoglycan-degrading metalloproteinases after addition of β-glycerophosphate and ascorbic acid. *Calcif. Tissue*, 54: 399-408 (1994).
Declaration filed in connection with the European Patent EP 1133558 Opposition, Expert opinion of Dr. Auristela Freire de Paes Alves, Ph.D., dated Sep. 9, 2009.
Declaration filed in connection with the European Patent EP 1133558 Opposition, Expert opinion of Dr. Walter Sebald, dated Sep. 24, 2009.
Declaration filed in connection with the European Patent EP 1133558 Opposition, Expert opinion of Prof. Dr. Edgar Wingender, dated Sep. 24, 2009.
Declaration filed in connection with the European Patent EP 1133558 Opposition, Expert opinion of Prof. Dr. Thomas Muller, dated Sep. 23, 2009.
Declaration of Alistair J. Henry, citation in Appeal, European Patent No. 1133558, dated Apr. 2, 2010.
Declaration of Dr. Raymond Dalgleish dated Dec. 8, 2011, citation in Appeal, European Patent No. 1133558.
Declaration of Prof. Edgar Wingender filed in connection with that Opposition regarding European Patent EP 1133558 B1, dated Mar. 10, 2011.
Declaration of Professor Teresa Attwood, citation in Appeal, European Patent No. 1133558, dated Apr. 13, 2010.
Declaration of Tim Arnett, citation in Appeal, European Patent No. 1133558, dated Apr. 2, 2010.
Delmas et. al., The use of biochemical markers of bone turnover in osteoporosis. *Osteoporosis International*, Suppl. 6:S2-17 (2000).
Diagram of the candidate interval, citation by Propriator in Opposition against European Patent No. 1721979 on Feb. 20, 2012.
Ducy et. al., 5-HT and bone biology. *Curr. Opin. Pharmacol.*, 11: 34-8 (2011).
Ducy et. al., Genetic control of cell differentiation in the skeleton. *Curr. Opin. Cell Biol.*, 10: 614-9 (1998).
Durham et. al., Alterations in insulin-like growth factor (IGF)-dependent IGF-binding protein-4 proteolysis in transformed osteoblastic cells. *Endocrinology*, 136(4):1374-80 (1995).
Ebara et. al., Mechanism for the action of bone morphogenetic proteins and regulation of their activity. *Spine*, 27(165):S10-5 (2002).
Eli Lilly Statement of Grounds of Appeal, Opposition to European Patent Application No. 1133558 B1, dated Sep. 28, 2009.
Eli Lilly, Biacore experiment comparison results, Setup assay to measure BMP binding to captured SOST, referenced on p. 41 of reference C193, dated Sep. 28, 2009.
Epstein et. al., Endocrine function in sclerosteosis. *S. Afr. Med. J.*, 55:1105-10 (1979).
European Patent Office Communication, Opposition to European Patent No. 1133558, dated Nov. 4, 2008.
European Patent Office, "Opinion of the Enlarged Board of Appeal dated Dec. 1992 G 1/92", available from [http://documents.epo.org/projects/babylon/eponet.nsf/0/907016FA57B46FD0C12572C8006CD2E2/$File/g920001.pdf], Jun. 15, 2011.
Expert Opinion from Dr. Catalina Lopez-Correa, submitted in Opposition to European Patent No. 1133558, dated Mar. 6, 2009.
Expert opinion of Professor Dr.-Ing Ulrich Vollrath, citation in Appeal of European Patent No. 1133558, dated Apr. 12, 2005.
Extract from Sigma Aldrich catalogue, Opposition against European Patent No. 1721979 by Opponent: Laudens, dated Jun. 15, 2011.
Eyre et. al., Characterization of aromatase and 17β-hydroxysteroid dehydrogenase expression in rat osteoblastic cells. *J. Bone Miner. Res.*, 13(6): 996-1004 (1998).
Foster et. al., Establishment of interference in osteoblasts by an osteopetrosis-inducing Avian Leukosis virus. *Virology*, 205: 376-8 (1994).
Fouser et. al., Feedback regulation of collagen gene expression: A Trojan horse approach. *Proc. Natl. Acad. Sci. USA*, 88: 10158-62 (1991).
Frost et. al., On the rat model of human osteopenias and osteoporoses. *Bone and Mineral*, 18:227-36 (1992).
Fujiwara et. al., GenBank Sequence Database Accession No. D79813, Feb. 9, 1996.
Gardner et. al., Bone mineral density in sclerosteosis; Affected individuals and gene carriers. *J. Clin. Endocrinol. Metab.*, 90(12): 6392-5 (2005).
Gavarini et. al., Opposite effects of PSD-95 and MPP3 PDZ proteins on serotonin 5-hydroxytryptamine2C receptor desensitization and membrane stability. *Molec. Biol.*, 17: 4619-31 (2006).
Gazzerro et. al., Bone morphogenetic proteins induce the expression of noggin which limits their activity in cultured rat osteoblasts. *J. Clin. Invest.*, 102(12):2106-14 (1998).
Gazzerro et. al., Potential drug targets within bone morphogenetic protein signaling pathways. *Curr. Opin. Pharmacol.*, 7: 325-3 (2007).
Geissler et la., Male pseudohermaphroditism caused by mutations of testicular 17β-hydroxysteroid hehydrogenase 3. *Nat. Genetics*, 7: 34-9 (1994).
Gencic et. al., Conservative amino acid substitution in the myelin proteolipid protein of Jimpymsd mice. *J. Neurosci.*, 10(1):117-24 (1990).
Geysen et. al., Cognitive features of continuous antigenic determinants. *J. Molec. Recog.*, 1(1):32-41 (1988).
Gitelman et. al., Vgr-1/BMP-6 induces osteoblastic differentiation of pluripotential mesenchymal cells. *Cell Growth & Differentiation*, 6:827-36 (1995).
Glasky et. al., Stability of specific immunoglobulin secretion by EBV-transformed lymphoblastoid cells and human-murine heterohybridomas. *Hybridoma*, 8:377-89 (1989).
Gowen et. al., Actions of recombinant human γ-interferon and tumor necrosis factor α on the proliferation and osteoblastic characteristics of human trabecular bone cells in vitro. *Arthritis Rheumatism*, 31(12): 1500-7 (1988).
Graner et. al., Splice variants of the *Drosophila* PS2 integrins differentially interact with RGD-containing fragments of the extracellular proteins tiggrin, Ten-m and D-laminin α2. *J. Biol. Chem.*, 273(29): 18235-41 (1998).
Green et al., Cytosolic pH regulation in osteoblasts. *J. Gen. Physiol.*, 95: 121-45 (1990).
Green et. al., Antigen-specific human monoclonal antibodies from mice engineered with human Ig heavy and light chain YACs. *Nat. Genet.*, 7:13 (1994).
Greene et. al., Screening Recombinant DNA Libraries. *Current Protocols in Molecular Biology*, Ch. 6(1) (1990).
Gribskov et. al., Profile analysis. *Meth. Enzym.*, 183:146-59 (1990).
Gribskov et. al., Profile analysis: Detection of distantly related proteins. *Proc. Nat. Acad. Sci. USA*, 84(13):4355-8 (1987).
Groeneveld et. al., Bone morphogenetic proteins in human bone regeneration. *Eur. J. Endocrinol.*, 142:9-21 (2000).
Gronthos et. al., Integrin expression and function on human osteoblast-like cells. *J. Bone Miner. Res.*, 12(8): 1189-97 (1997).
Groppe et. al., Structural basis of BMP signalling inhibition by the cystine knot protein noggin. *Nature*, 420:636-42 (2002).
Guinness-Hey, Increased trabecular bone mass in rats treated with human synthetic parathyroid hormone. *Metab. Bone Dis. Relat. Res.*, 5:177-81 (1984).
Harlow et. al., Antibodies: A Laboratory Manual, Cold Spring Harbor Laboratory, 141-157 (1988).
Harris, Processing of C-terminal lysine and arginine residues of proteins isolated from mammalian cell culture. *J. Chromatogr.*, 705:129-34 (1995).
Hart et. al., Crystal structure of the human TβR2 ectodomain-TGF-β3 complex. *Nat. Struc. Biol.*, 9(3):203-8 (2002).
Hay et. al., ATCC Cell Line and Hybridomas, American Type Culture Collection, 8th Ed., pp. 149, 258, 428 (1994).

(56) References Cited

OTHER PUBLICATIONS

He et. al., High-throughput dynamic light scattering method for measuring viscosity of concentrated protein solutions. *Anal. Biochem.*, 399(1): 141-3 (2010).
Heinecke et. al., Receptor oligomerization and beyond: A case study in bone morphogenetic proteins, *BMC Biol.*, 7: 59 (2009).
Hill et. al., Multiple extracellular signals promote osteoblast survival and apoptosis. *Endocrinology*, 138(9):3849-58 (1997).
Hillier et. al., EMBL Sequence Database Accession No. AA393939, May 19, 1997.
Hillier et. al., GenBank Sequence Database Accession No. AA393768, Apr. 24, 1997.
Hillier et. al., Generation and analysis of 280,000 human expressed sequence tags. *Genome Res.*, 6: 807-28 (1996).
Hilliker et. al., Truncation of the amino terminus of PTH alters its anabolic activity on bone in vivo. *Bone*, 19(5): 469-77 (1996).
Hirschhorn, Letter to the editor: Dominance and homozygosity in man. *Am. J. Med. Genetics*, 18: 541 (1984).
Hock et. al., Perspective: Osteoblast apoptosis and bone turnover. *J. Bone Miner. Res.*, 16(6):975-84 (2001).
Hoffman et. al., BMP Signaling Pathways in Cartilage and Bone Formation, *Crit. Rev. Eukaryotic Gene Exp.*, 11(1-3):23-45 (2001).
Hoggard et. al., Localization of leptin receptor mRNA splice variants in murine peripheral tissues by RT-PCR and in situ hybridization. *Biochem. Biophys. Res. Commun.*, 232: 383-7 (1997).
Hollinger et. al., Engineered antibody fragments and the rise of single domains. *Nat. Biotech.*, 23(9):1126-36 (2005).
Holm et. al., Protein folds and families: Sequence and structure alignments. *Nucl. Acid Res.*, 27(1):244-7 (1999).
Holt, et. al., Domain antibodies: Proteins for therapy. *Trends Biotechnol.*, 21(11):484-90 (2003).
Hoogenboom et. al., By-passing immunisation: Human antibodies from synthetic repertoires of germline VH gene segmens rearranged in vitro. *J. Molec. Biol.*, 227:381-8 (1992).
Hoogewerf et. al., Glycosaminoglycans mediate cell surface oligomerization of chemokines. *Biochemistry*, 36: 13570-8 (1997).
Horton et. al., Arg-Gly-Asp (RGD) peptides and the anti-vitronectin receptor antibody 23C6 inhibit dentine resorption and cell spreading by osteoclasts. *Exp. Cell Res.*, 195: 368-75 (1991).
Hsu et. al.,The Xenopus dorsalizing factor gremlin indentified a novel family of secreted proteins that antagonize BMP activities. *Molec. Cell*, 1:673-83 (1998).
Hufner et. al., Evidence for an osteoblast-activating factor in a patient with peripheral T-cell lymphoma and osteosclerosis. *Klin. Wochenscher.*, 67: 402-7 (1989).
Hulley et. al., Inhibition of mitogen-activated protein kinase activity and proliferation of an early osteoblast cell line (MBA 15.4) by dexamethasone: Role of protein phosphatases. *Endocrinol.*, 139(5): 2423-31 (1998).
Huse et. al., Generation of a large combinatorial library of the immunoglobulin repertoire in phage lambda. *Science*, 246:1275-81 (1989).
Hwang et. al., Use of human germline genes in a CDR homoloy-based approach to antibody humanization. *Methods*, 36(1):35-42 (2005).
Ide et. al., GenBank Sequence Database Accession No. BAA19765, Feb. 7, 1999.
Ide et. al., GenBank Sequence Datacase Accession No. D89675, Feb. 7, 1999.
Iemura et. al., Direct binding of follistatin to a complex of bone-morphogenetic protein and its receptor inhibits ventral and epidermal cell fates in early Xenopus embryo. *Proc. Natl. Acad. Sci. USA*, 95:9337-42 (1998).
Innis et. al., Evolutionary trace analysis of TGF-B and related growth factors: Implications for stie-directed mutagenesis. *Protein Engineering*, 13(12):839-47 (2000).
Jakobovits et. al., Production of antigen-specific human antibodies from mice engineered with human heavy and light chain YACs a. *Ann. N.Y. Acad. Sci.*, 764:525-35 (1995).

Jee et. al., Overview: Animal models of osteopenia and osteoporosis. *J. Musculoskel. Neuron. Interact.*, 1:193-207 (2001).
Jilka et. al., Increased bone formation by prevention of osteoblast apoptosis with parathyroid hormone. *J. Clin. Invest.*, 104:439-46 (1999).
Jilka et. al., Osteoblast programmed cell death (apoptosis): Modulation by growth factors and cytokines. *J. Bone Miner. Res.*, 13(5): 793-802 (1998).
Jones, Progress in protein structure predication. *Curr. Opin. Struct. Biol.*, 7(3):377-387 (1997).
Kabat et. al., Sequences of proteins of immunological interest, U.S. Department of Health and Human Services, *NIH, USA* (1987) (Table of Contents).
Kalu, The ovariectomized rat model of postmenopausal bone loss. *Bone and Mineral*, 15:175-92 (1991).
Kang et. al., Linkage of recognition and replication functions by assembling combinatorial antibody Fab libraries along phage surfaces. *Proc. Natl. Acad. Sci. USA*, 88:4363-6 (1991).
Katagiri et. al., The non-osteogenic mouse pluripotent cell line, C3H10T1/2, is induced to differentiate into osteoblastic cells by recombinant human bone morphogenetic protein-2. *Biochem. Biophys. Res. Comm.*, 172(1):295-9 (1990).
Kawabata et. al., Signal transduction by bone morphogenetic proteins. *Cytokine and Growth Factor Reviews*, 9(1):49-61 (1998).
Keller et. al., Molecular recognition of BMP-2 and BMP receptor IA. *Nat. Struct. Mol. Biol.*, 11(5):481-488 (2004).
Khalil, TGF-β: From latent to active. *Microbes and Infection*, 1(15):1255-63 (1999).
Khosla et. al., Concise review for primary-care physicians. Treatment pptions for osteoporosis. *Mayo Clin. Proc.*, 70:978-82 (1995).
Kirsch et. al., BMP-2 antagonists emerge from alterations in the low-affinity binding epitope for receptor BMPR-II, *EMBO J.*, 19(13): 3314-24 (2000).
Kohler et. al., Continuous cultures of fused cells secreting antibody of predefined specificity. *Nature*, 256:495 (1975).
Koli et. al., Latency, activation, and binding proteins of TGF—. *Microscopy Res. Tech.*, 52:354-62 (2001).
Koreth et. al., Microsatellites and PCR genomic analysis. *J. Pathology*, 178:239-48 (1996).
Kramer et. al., The gapped duplex DNA approach to oligonucleotide-directed mutation construction. *Nuc. Acids Res.*, 12:9441 (1984).
Krause et. al., Distinct modes of inhibition by sclerostin on bone morphogenetic protein and Wnt signaling pathways. *J. Biol. Chem.*, 285(53): 41614-26 (2010).
Kunkel et. al., Rapid and efficient site-specific mutagenesis without phenoypic selection. *Meth. Enzymol.*, 154:367-82 (1987).
Kunkel, Rapid and efficient site-specific mutagenesis without phenotypic selection. *Proc. Natl. Acad. Sci. USA*, 82:488-92 (1985).
Kurahashi et. al., Regions of genomic instability on 22q11 and 11q23 as the etiology for the recurrent constitutional t (11;22). *Hum. Molec. Genet.*, 9: 1665-70 (2000).
Kusu et. al., Sclerostin is a novel secreted osteoclast-derived bone morphogenetic protein antagonist with unique ligand specificity. *J. Biol. Chem.*, 278:24113-7 (2003).
Labat et. al., Retroviral expression in mononuclear blood cells isolated from a patient with osteopetrosis (Albers-Schonberg disease). *J. Bone Miner. Res.*, 5(5): 425-35 (1989).
Labat, A new approach to the study of the origin of genetic disease: Retroviral etiology of osteopetrosis. *Biomed. Pharmacother.*, 45: 23-7 (1991).
Lasic, Novel applications of liposomes. *Trends Biotechnol.*, 16(7):307-21 (1998).
Latham, The biochemical and cellular characterization of sclerostin, The causative gene for sclerostenosis. *Calcified Tissue International*, 70(4):244 (2002).
Leppert et. al., Benign familial neonatal epilepsy with mutations in two potassium channel genes. *Curr. Opin. Neurol.*, 12: 143-7 (1999).
Lewiecki et. al., Sclerostin monoclonal antibody therapy with AMG 785: A potential treatment for osteoporosis. *Exp. Opin. Biol. Ther.*, 11(1): 117-27 (2011).
Li et. al., Sclerostin binds to LRP5/6 and antagonizes canonical Wnt signaling. *J. Biol. Chem.*, 280: 19883-7 (2005).

(56) References Cited

OTHER PUBLICATIONS

Li et. al., Treatment with an anti-sclerostin antibody directly stimulates bone formation in a dose-dependent manner in ovariectomized rats with established osteopenia. J. Bone Min. Res., 22(Suppl. S1): S65 (2007).

Lian et. al., Bone Formation: Osteoblast Lineage Cells, Growth Factors, Matrix Proteins, and the Mineralization Process, Primer on the Metabolic Bone Diseases and Disorders of Mineral Metabolism, 4th Edition, 14-29 (1999).

Lierop et. al., Van Buchem disease: Clinical, biochemical and densitometric features of patients and disease carriers. *J. Bone Miner. Res. Accepted Article* (2012).

Liu et. al., GenBank Sequence Database Accession No. U25110, Feb. 2, 1996.

Liu et. al., Human type II receptor for bone morphogenic proteins (BMPs): Extension of the two-kinase receptor model to the BMPs. *Molec. Cell. Biol.*, 15(7):3479-86 (1995).

Lonberg et. al., Antigen-specific human antibodies from mice comprising four distinct genetic modifications. *Nature*, 368:856 (1994).

Loots et. al., Genomic deletion of a long-range bone enhancer misregulates sclerostin in Van Buchem disease. *Genome Res.*, 15: 928-35 (2005).

Low et. al., Mimicking somatic hypermutation: Affinity maturation of antibodies displayed on bacteriophage using a bacterial mutator strain. *J. Mol. Biol.*, 250:350-68 (1996).

Lowik et. al., Wnt signaling is involved in the inhibitory action of sclerostin on BMP-stimulated bone formation. *J. Musculoskeleton Neuronal Interact.* 6: 357 (2006).

Luckman et. al., Heterocycle-containing bisphosphonates cause apoptosis and inhibit bone resorption by preventing protein prenylation: Evidence from structure-activity relationships in J774 macrophages. *J. Bone Miner. Res.*, 13(11): 1668-78 (1998).

Luckman et. al., Nitrogen-containing bisphosphonates inhibit the mevalonate pathway and prevent post-translational prenylation of GTP-binding proteins, including Ras. *J. Bone Miner. Res.*, 13(4): 581-9 (1998).

Malone et. al., Bone anabolism achieved by reducing sclerostin bioavailability with an anti-sclerostin antibody. 37th International Sun Valley Workshop on Skeletal Tissue Biology. Aug. 5-8, 2007.

Mango et. al., Carboxy-terminal truncation activates glp-1 protein to specify vulval fates in Caenorhabditis elegans. *Lett. Nature*, 352: 811-15 (1991).

Margalit et. al., Comparative analysis of structurally defined herparin binding sequences reveals a distinct spatial distribution of basic residues. *J. Biol. Chem.*, 268 (26): 19228-31 (1993).

Margalit, Liposome-mediated drug targeting in topical and regional therapies. *Crit. Rev. Ther. Drug Carrier Syst.*, 12(2-3):233-61 (1995).

Marks et. al., By-passing immunization: Building high affinity human antibodies by chain shuffling. *Bio/Technology*, 10:779-83 (1992).

Matthews et. al., Adenovirus protein-protein interactions: Hexon and protein VI. *J. Gen. Virol.*, 75: 3365-74 (1994).

Mayer et. al., Differentiation of osteogenetic cells: Systems and regulators, Z. Orthop., 130: 276-84 (1992)—Abstract Only.

McClung et. al., Inhibition of sclerostin with AMG 785 in postmenopausal women with low bone mineral density: Phase 2 trial results—Abstract presented at the 2012 meeting of the American Society for Bone and Mineral Reasearch (2012).

Memorandum C, Munich Diplomatic Conference, Sep. 1 to Oct. 6, 1973.

Minabe-Saegusa et. al., Genbank Sequence Database Accession No. AB011030, Jun. 23, 1998.

Minutes of the oral proceedings before the opposition division for Opposition against European Patent 1721979, dated May 10, 2013.

Miyazono et. al., Divergence and convergence of TGF-β/BMP signaling. *J. Cell. Physiol.*, 187:265-76 (2001).

Miyazono et. al., TGF-β signaling by Smad proteins. *Adv. Immunology*, 75:115-57 (2000).

Morais et. al., In vitro biomineralization by osteoblast-like cells I. Retardation of tissue mineralization by metal salts. *Biomaterials*, 19: 13-21 (1998).

Mori et. al., A novel amino acid substitution a the receptor-binding site on the hemaglutinin of H3N2 influenza A viruses isolated from 6 cases with acute encephalopathy during 1997-1998 season in Tokyo. *Arch. Virol.*, 144: 147-55 (1999).
Morrison et. al., ATP is a potent stimulator of the activiation and formation of rodent osteoclasts. *J. Physiol.*, 511.2: 495-500 (1998).
Mosekilde et. al., Assessing bone quality—Animcal models in preclinincal osteoporosis research. *Bone*, 17 (4): 343S-52S (1995).
Moult, The current state of the art in protein structure predicion. *Curr. Opin. Biotech.*, 7(4):422-7 (1996).
Mullins et. al., Perspectives series: Molecular medicine in genetically engineered animals; Transgenesis in the rat and larger mammals. *J. Clin. Invest.*, 97(7):1557-60 (1996).
Muntoni et. al., A mutation in the dystrophin gene selectively affecting dystrophin expression in the heart. *J. Clin. Invest.*, 96: 693-9 (1995).
Nagaraja et. al., X chromosome map at 75-kb STS resolution, revealing extremes of recombination and GC content. *Genome Res.*, 7: 210-22 (1997).
Nakase et. al., Transient and localized expression of bone morphogenetic protein 4 messenger RNA during fracture healing. *J. Bone Miner. Res.*, 9(5):651-9 (1994).
Nelson, Positional cloning reaches maturity. *Curr. Opin. Genet. Devel.*, 5:298-303 (1995).
Nickel et. al., The crystal structure of the BMP-2: BMPR-1A complex and the generation of BMP-2 antagonists. *J. Bone Joint Surg.*, 83-A:S1-7-S1-14 (2001).
Nicolas et. al., An age-related decrease in the concentration of insulin-like growth factor binding protein-5 in human cortical bone. *Calcif. Tissue Int.*, 57:206-12 (1995).
Nifuji et. al., Coordinated expression of noggin and bone morphogenetic proteins (BMPs) during early skeletogenesi and induction of noggin expression by BMP-7. *J. Bone Miner. Res.*, 14(12):2057-66 (1999).
Nisonoff et. al., Separation of univalent fragments from the bivalent rabbit antidody molecule by reduction of disulfide bonds. *Arch. Biochem. Biophys.*, 89:230-44 (1960).
Niu et. al., Sclerostin inhibition leads to increased periosteal and endocortical bone formation as well as decreased cortical porosity in aged ovariectomized rats. *J. Bone Min. Res.*, 22(Suppl. S1) S65 (2007).
Nordsletten et. al., The neuronal regulation of fracture healing. *Acta Orthop Scand.*, 65(3): 299-304 (1994).
Notice of Opposition against European Patent No. 1133558, Opponent: Eli Lilly and Company, dated May 31, 2007.
Notice of Opposition against European Patent No. 1721979, Opponent: Eli Lilly & Company, dated Jun. 15, 2011.
Notice of Opposition against European Patent No. 1721979, Opponent: Laudens, dated Jun. 15, 2011.
Notice of Opposition against European Patent No. 1721979, Opponent: Novartis AG, dated Jun. 15, 2011.
Notice of Opposition to European Patent No. 1 133 558, dated May 29, 2007.
Nygren et. al., Scaffolds for engineering novel binding sites in proteins. *Curr. Opin. Struct. Biol.*, 7:463-9 (1997).
Observations of Opponent: Laudens in response to summons to oral proceedings in Opposition against European Patent No. 1721979, dated Feb. 25, 2013.
Oelgeschlager et. al., The evolutionarily conserved BMP-binding protein twisted gastrulation promotes BMP signalling. *Nature*, 405:757-63 (2000).
OMIM #607625, Niemann-pick disease, type C2 (2007).
Ominsky, et. al., Sclerostin monoclonal antibody treatment increases bone strength in aged osteopenic ovariectomozed rats. *J. Bone Min. Res.*, 21(1): S44 PRES1161 (2006). Abstract.
Opposition Decision for Opposition against European Patent No. 1721979, dated Aug. 2, 2013.
Opposition Statement of May 20, 2007 filed by Opponent 2 (Eli Lilly) against European Patent No. 1133558.

(56) References Cited

OTHER PUBLICATIONS

Oreffo et. al., Human bone marrow osteoprogenitors express estrogen receptor-alpha and bone morphogenetic proteins 2 and 4 mRNA during osteoblastic differentiation. *J. Cell. Biochem.*, 75:382-92 (1999).
Orriss et al., Purinergic signaling and bone remodeling. *Curr. Opin. Pharmacol.*, 10:322-30 (2010).
Utting et al., Hypoxia stimulates osteoclast formation from human peripheral blood. *Cell Biochem. Funct.*, 28:374-80 (2010).
Oshima et. al., TGF-β receoptor type II deficiency results in defects of yolk Sac hematopoiesis and vasculogenesis. *Dev. Biol.*, 179:297-302 (1996).
Padhi et. al., Anti-sclerostin antibody increases markers of bone formation in healthy postmenopausal women. *J. Bone Min. Res.*, 22: S37 (2007).
Padhi et. al., OC35—Effects of anti-sclerostin monoclonal antibody in healthy postmenopausal women. *Osteoporosis Int.*, 19: Suppl. 1: S19 (2008).
Padlan et. al., Structure of an antibody-antigen complex; Crystal structure of the HyHEL-10 Feb-lysozyme complex. *Proc. Natl. Acad. Sci. USA*, 86:5938-42 (1989).
Palokangas et. al., Endocytic pathway from the basal plasma membrane to the ruffled border membrane in bone-resorbing osteoclasts. *J. Cell Sci.*, 110: 1767-80 (1997).
Pandey et. al., Nucleotide sequence database: A gold mine for biologists. *TIBS.*, 24: 276-80 (1999).
Papapoulos et. al., Targeting sclerostin as potential treatment of osteoporosis. *Ann. Rheum. Dis.*, 70(Suppl. 1): 1119-22 (2011).
Patel et. al., Current and potential future drug treatments for osteoporosis. *Ann. Rheumatic Dis.*, 55: 700-14 (1996).
Patten et. al., Applications of DNA shuffling to pharmaceuticals and vaccines. *Curr. Opin. Biotechnol.*, 8:724-33 (1997).
Pearson et. al., Effective protein sequence comparison. Chapter 15, pp. 227-258 (1996).
Piao et. al., The proximal promotor region of the gene encoding human 17β-hydroxysteroid dehydrogenase type 1 contains GATA, AP-2, and Sp1 response elements: Analysis of promotor function in choriocarcinoma cells. *Endrocrinol.*, 138(8): 3417-25 (1997).
Piccolo et. al., The head inducer Cerberus is a multifunctional antagonist of nodal, BMP and Wnt signals. *Nature*, 397: 707-10 (1999).
Piek et. al., Specificity, diversity, and regulation of TGF-β superfamily signaling. *FASEB J.*, 13:2105-24 (1999).
Pietromonaco et. al., Protein kinase C-Θ phosphorylation of moesin in the actin-binding sequence. *J. Biol. Chem.*, 273:7594-603 (1998).
Pignatti et. al., Tracking disease genes by reverse genetics. *J. Psychiar. Res.*, 26(4):287-98 (1992).
Pittenger et. al., Multilineage potential of adult human mesenchymal stem cells. *Science*, 284:143-7 (1999).
Pluckthun et. al., Expression of functional anitbody Fv and Fab fragments in *Escherichia coli*. *Meth. Enzymol.*, 178:497-515 (1989).
Pockwinse et. al., Expression of cell growth and bone specific genes at single cell resolution during development of bone tissue-like organization in primary osteoblast cultures. *J. Cell. Biol.*, 49:310-23 (1992).
Poole et. al., Sclerostin is a delayed secreted product of osteocytes that inhibit bone formation. *FESEB J.*, 19: 1842-4 (2005).
Porter, The hydrolysis of rabbit γ-globulin and antibodies with crystalline papain. *Biochem. J.*, 73:119-26 (1959).
Proprietor's Response to Opponent's Statement of Grounds of Appeal, European Patent No. 1133558, dated Apr. 15, 2010.
Proprietor's Response to Oppositions against European Patent No. 1721979, UCB Pharma S.A., dated Feb. 20, 2012.
Proprietor's Written submission in preparation for oral proceedings in Opposition against European Patent No. 1721979, Proprietor: UCB Pharma S.A., dated Feb. 25, 2013.
Quintanar-Guerrero et. al., Preparation techniques and mechanisms of formation of biodegradable nanoparticles from preformed polymers. *Drug Dev. Ind. Pharm.*, 24(12):1113-28 (1998).
Rachner et. al., Osteoporosis: Now and the future. *Lancet*, 377(9773): 1276-87 (2011).
Rawadi et. al., BMP-2 controls alkaline phosphatase expression and osteoblast mineralization by a Wnt autocrine loop. *J. Bone Min. Res.*, 18: 1842-53 (2003).
Reb, Antikorpergegen sclerostin, *Medical Tribune*, 39:12 (2007).
Reddi et. al., The *Escherichia coli* chaperonin 60 (groEL) is a potent stimulator of osteoclast formation. *J. Bone Miner. Res.*, 13(8): 1260-6 (1998).
Reddi, Interplay between bone morphogenetic proteins and cognate binding proteins in bone and cartilage development: Noggin, chordin and DAN. *Arthritis Res.*, 3(1):1-5 (2000).
Response to Proprietor's brief of Apr. 15, 2010, European Patent Opposition, EP-1133558 B1, dated Mar. 18, 2011.
Riggs, Overview of osteoporosis. *West J. Med.*, 154:63-77 (1991).
RnD Systems catalogue excerpt, Opposition against European Patent No. 1721979 by Opponent: Novartis AG dated Jun. 15, 2011.
Roberts et. al., Essential functional interactions of SAFA, a *Saccharomyces cerevisiae* complex of Spt, Ada, and Gcn5 proteins, with the Snf/Swi and Srb/Mediator complexes. *Genetics*, 147: 451-65 (1997).
Robinson et. al., The sclerostin antibody project. *Hum. Antibodies*, 16: 36 (2007).
Roitt et la., Roitt's Essential Immunology, 9th Edition, pp. 90-91 (1997).
Rosenzweig et. al., Cloning and characterization of a human type II receptor for bone morphogenetic proteins. *Proc. Natl. Acad. Sci. USA*, 92:7632-7636 (1995).
Rosenzweig et. al., GenBank Sequence Database Accession No. CAA88759, Oct. 7, 2008.
Rosenzweig et. al., GenBank Sequence Database Accession No. Z48923, Oct. 7, 2008.
Rudikoff, et. al., Single amino acid substitution altering antigen-binding specificity. *Proc. Natl. Acad. Sci. USA*, 79:1979-83 (1982).
Ruppert et. al., Human bone morphogenetic protein 2 contains a heparin-binding site which modifies its biological activity. *Eur. J. Biochem.*, 237: 295-302 (1996).
Sada et. al., Adsorption equilibirum in immuno-affinity chromatography with polyclonal and monoclonal antibodies. *Biotechnol. Bioengin.*, 28 (1986). Abstract.
Sali et. al., Comparative protein modeling by satisfaction of spatial restraints. *J. Mol. Biol.*, 234(3):779-815 (1993).
Sambrook et. al., Synthetic oligonucleotide probes, molecular cloning—A Laboratory Manual, Ch.11:11.1-11.19 and 11.58-11.61 (1989).
Sanger et. al., DNA sequencing with chain-terminating inhibitors. *Proc. Natl. Acad. Sci. USA*, 74:5463-7 (1997).
Sastry et. al., Cloning of the immunological repertoire in *Escherichia coli* for generation of monoclonal catalytic antibodies: Construction of a heavy chain variable region-specific cDNA library. *Proc. Natl. Acad. Sci. USA*, 86:5728-32 (1989).
Scatchard et. al., The attractions of proteins for small molecules and ions. *Ann. N.Y. Acad. Sci.*, 51:660-72 (1949).
Scheufler et. al., Crystal structure of human bone morphogenetic protein-2 at 2.7 A resolution. *J. Mol. Biol.*, 287(1):101-15 (1999).
Schlebusch et. al., Production of a single-chain fragment of the murine anti-idiotypic antibody ACA125 as phage-displayed and soluble antibody by recombinant phage antibody technique. *Hybridoma*, 16:47-52 (1997).
Schlunegger et. al., Refined crystal structure of human transforming growth factor β2 at 1.95 A Resolution. *J. Mol. Biol.*, 231(2):445-458 (1993).
Schmidt et. al., Retrovirus-induced osteopetrosis in mice: Effects of viral infection on osteogenic differentiation in skeletoblast cell cultures. *Am. J. Pathol.*, 129(3): 503-10 (1987).
Schmitt et. al., Bone morphogenetic proteins: An update on basic biology and clinical relevance. *J. Orth. Res.*, 17:269-78 (1999).
Schwappacher et. al., NCBI Sequence Database Accession No. NM_001204, Aug. 16, 2009.
Scully et. al., BRCA1 is a component of the RNA polymerase II holoenzyme. *Proc. Natl. Acad. Sci. USA*, 94: 5605-10 (1997).
Second declaration of Martyn Robinson, citation in Appeal, European Patent No. 1133558, dated Apr. 15, 2010.

(56) References Cited

OTHER PUBLICATIONS

Serra et. al., Expression of a truncated, kinase-defective TGF-β type II receoptor in mouse skeletal tissue promotes terminal chondrocyte differentiation and osteoarthritis. *J. Cell. Biol.*, 139(2):541-52 (1997).
Sigmund, Viewpoint: Are studies in genetically altered mice out of control? *Arterioscler. Thromb. Vasc. Biol.*, 20:1425-9 (2000).
Silverman et. al., Sclerostin, *J. Osteoporosis*, 2010: 1-3 (2010).
Sippl et. al., Threading thrills and threats. *Structure*, 4(1):15-19 (1996).
Siris, Clinical Review: Paget's disease of bone. *J. Bone Miner. Res.*, 13(7): 1061-5 (1998).
Sivakumar et. al., New insights into extracellular matrix assembly and reorganization from dynamic imaging of extracellular matrix proteins in living osteoblasts. *J. Cell. Sci.*, 119(7):1350-60 (2006).
Skiple Skjerpen et. al., Binding of FGF-1 variants to protein kinase CK2 correlates with mitogenicity. *EMBO J.*, 21(15): 4058-69 (2002).
Slater et. al., Involvement of platelets in stimulating osteogenic activity. *J. Orthopaedic Res.*, 13: 655-63 (1995).
Smith et. al., Glucocorticoids inhibit development stage-specific osteoblast cell cycle. *J. Biol. Chem.*, 275:19992-20001 (2000).
Smith, TGF β inhibitors, new and unexpected requirements in vertebrate development. *TIG*, 15(1):3-5 (1999).
Sohocki et. al., A range of clinical phenotypes associated with mutations in CRX, a photoreceptor transcription-factor gene. *Am. J. Hum. Genet.*, 63: 1307-15 (1998).
Spranger, International classification of osteochondrodysplasias, *Eur. J. Pediatr.*, 151: 407-15 (1992).
Staehling-Hampton et. al., A 52-kb delection in the SOST-MEOX1 intergenic region on 17q12-q21 is associated with van Buchem disease in the Dutch population. *Am. J. Med. Gen.*, 110: 144-52 (2002).
Stanley et. al., DAN is a secreted glycopeotein related to Xenopus cerberus. Mech. Dev., 77: 173-84 (1998).
Statement of Grounds of Appeal to Decision of Opposition against European Patent No. 1133558, dated Sep. 28, 2009.
Stenmark et. al., Distinct structural elements of rab5 define its functional specificity. *EMBO J.*, 13(3): 575-83 (1994).
Strachan et. al. (Eds.), Diagram from text book entitled Human Molecular Genetics, 2nd Edition (1999).
Strachan et. al. (Eds.), Human Molecular Genetics, 1st Edition, p. 420 (1996).
Strachan et. al., (Eds.), Human Molecular Genetics, 2nd Edition, Figure 15.4 (1999).
Submission in response to oral proceedings in Opposition against European Patent No. 1721979, Opponent: Eli Lilly, dated Apr. 24, 2013.
Sudo et. al., In vitro differentiation and calcification in a new clonal osteogenic cell line derived from newborn mouse calvaria. *J. Cell Biol.*, 96:191-8 (1983).
Summons to attend oral proceedings for Opposition against European Patent No. 1133558, dated Nov. 4, 2008.
Summons to attend oral proceedings in Opposition against European Patent No. 1721979, dated Nov. 12, 2012.
Sutherland et. al., Sclerostin romotes the apoptosis of human osteoblastic cells: A novel regulation of bone formation. *Bone*, 35:828-35 (2004).
Suzawa et. al., Extracellular matrix-associated bone morphogenetic proteins are essential for differentiation of murine osteoblastic cells in vitro. *Endocrinology*, 140:2125-33 (1999).
Sverdlov et. al., Perpetually mobile footprints of ancient infections in human genome. *FEBS Lett.*, 428: 1-6 (1998).
Sylatron label, Opposition against European Patent No. 1721979 by Opponent: Novartis AG, dated Jun. 15, 2011.
Takakura, Drug delivery systems in gene therapy. *Nippon Rinsho*, 56(3):691-5 (1998) (Abstract Only).
Takeda et. al., GenBank Sequence Database Accession No. AAB33865, May 27, 1995.
Takeda et. al., GenBank Sequence Database Accession No. D38082, dated Dec. 27, 2006.
Takeda et. al., GenBank Sequence Database Accession No. S75359, May 27, 1995.
Takeda et. al., NCBI Sequence Database Accession No. NM_030849, Feb. 11, 2009.
Takeda, Expression of serine/threonine kinase receptors during ectopic bone formation induced by bone morphogenetic protein (BMP). *Kokubyo Gakkai Zasshi*, 61(4):512-26 (1994).
Tam et. al., TGF-β receptor expression on human keratinocytes: A 150 kDa GPI-anchored TGF-β1 binding protein forms a heteromeric complex with type I and type II receptors. *J. Cellular Biochem.*, 70:573-56 (1998).
Taylor et. al., Human immunoglobulin transgenes undergo rearrangement, somatic mutation and class switching in mice that lack endogenous IgM. *Int. Immun.*, 6:579 (1994).
The Merck Manual-Second Home Edition, Ch. 61:1-3 (2005).
Thompson et. al., Affinity maturation of a high-affinity human monoclonal antibody against the third hypervariable loop of human immunodeficiency virus: Use of phage display to improve affinity and broaden strain reactivity. *J. Mol. Biol.*, 256:7-88 (1996).
Thornton et. al., Prediction of progress at last. *Nature*, 354:105-6 (1991).
Tjaderhane et. al., A high sucrose diet decreases the mechanical strength of bones in growing rats. *J. Nutr.*, 128: 1807-10 (1998).
Tuncay et. al., Oxygen tension regulates osteoblast function. *Am. J. Orthod. Dentofac. Orthop.*, 105: 457-63 (1994).
UCB and Amgen announce positive phase 2 results of CDP7851/AMG785 in patients with post menopausal osteoporosis (PMO), dated Apr. 21, 2011—Citation in Opposition against European Patent No. 1721979.
Uitterlinden et. al., Relation of alleles of the collagen type lα1 gene to bone density and the risk of osteoporotic fractures in postmenopausal women. *New Engl. J. Med.*, 338: 1016-21 (1998).
Valero et. al., Quaternary structure of casein kinase 2. *J. Biol. Chem.*, 27(14): 8345-52 (1995).
van Bezooijen et. al., Sclerostin is an osteocyte-expressed negative regulator of bone formation, but not a classical BMP antagonist. *J. Exp. Med.*, 199: 805-14 (2004).
van Bezooijen et. al., SOST/sclerostin, an osteocyte-derived negative regulator of bone formation, *Cytokine Growth Factor Rev.*, 16: 319-27 (2005).
van Bezooijen et. al., Wnt but not BMP signaling is involved in the inhibitory action of sclerostin on BMP-stimulated bone formation. *J. Bone. Miner. Res.*, 22:19-28 (2007).
Van Hul et. al., Van Buchem Disease (hyperostosis corticalis generalisata) maps to chromosome 17q12-a21. *Am. J. Hum. Genet.*, 2:391-9 (1998).
Vanier et. al., Recent advances in elucidating Niemann-Pick C disease. *Brain Pathol.*, 8: 163-74 (1998).
Veverka et. al., Characterization of the structural features and interactions of sclerostin. *J. Biol. Chem.*, 284(16): 10890-900 (2009).
Viter et. al., Analysis of antigenic structure of potato virus M Ukrainian strains. *Biopolimery I Kletka, Naukova Dumka, Kiev K, UK*, 16: 312-9 (2000).
Von Bubnoff et. al., Intracellular BMP signaling regulation in vertebrates: Pathway or network? *Dev. Biol.*, 239:1-14 (2001).
Wall, Transgenic livestock: Progress and prospects for the future. *Theriogenology*, 45:57-68 (1996).
Wang et. al., IFP 35 forms complexes with B-ATF, a member of the AP1 family of transcription factors. Biochem. Biophys. Res. Commun., 229: 316-22 (1996).
Wang, Bone morphogenetic proteins (BMPs): Therapeutic potential in healing bony defects. *TIBTECH*, 11:379-83 (1993).
Warmington et. al., Sclerostin antagonism in adult rodents, via monoclonal antibody mediated blockade, increases bone mineral density and implicates sclerostia as a key regulator of bone mass during adulthood. *J. Bone Min. Res.*, 19:S56-7 (2004).
Warmington et. al., Sclerostin monoclonal antibody treatment of osteoporotic rats completely reverses one year of overiectomy-induced systemic bone loss, *J. Bone Min. Res.*, 20:S22 (2005).
Winkler et. al., Noggin and sclerostin bone morphogenetic protein antagonists form a mutually inhibitory complex. *J. Biol. Chem.*, 279(35): 36296-8 (2004).

(56) References Cited

OTHER PUBLICATIONS

Winkler et. al., Osteocyte control of bone formation via sclerostin, a novel BMP antagonist. *EMBO J.* 22: 6267-76 (2003).
Winkler et. al., Sclerostin inhibition of Wnt-3a-induced C3H10T1/2 cell differentiation is indirect and mediated by bone morphogenetic proteins. *J. Biol. Chem.* 280: 2498-502 (2005).
Winter et. al., Making antibodies by phase display technology. *Annu. Rev. Immunol.*, 12:433-55 (1994).
Wolff et. al., Monoclonal antibody homodimers: Enhanced antitumor activity in nude mice. Cancer Res., 53:2560-5 (1993).
Wollenberger et. al. (Eds.), Analytische Biochemie, Chapter 3, pp. 47-49 (2003).
Written submission—Observation by a Third Party According to Art.115 EPC, Opposition to European Patent No. 1133558, dated Nov. 25, 2008.
Written submission in response to summons to oral proceedings in Opposition against European Patent No. 1721979, Opponent: Norvartis AG, dated Feb. 25, 2013.
Written submission in response to summons to oral proceedings in Opposition against European Patent No. 1721979, Opponent: Eli Lilly Company, dated Feb. 25, 2013.
Written submission of Eli Lilly & Company to European Patent Office, Opposition to European Patent No. 1133558, dated May 29, 2007.
Written Submission of Eli Lilly & Company, Opposition to European Patent No. 1133558, dated Mar. 9, 2009.
Written submission of UCB S.A., Proprietor's Preliminary Response to the Opponent's submission of Mar. 9, 2009, Opposition to European Patent No. 1133558, dated Mar. 20, 2009.
Written submission of UCB S.A., Proprietor's Response to Opposition against European Patent No. 1133558, dated Mar. 14, 2008.
Yanagita et. al., USAG-1: A bone morphogenetic protein antagonist abundantly expressed in the kidney. *Biochem. Biophys. Res. Comm.*, 316: 490-550 (2004).
Yang et. al., CDR walking mutagenesis for the affinity maturation of a potent human Anti-HIV-1 antibody into the picomolar range. *J. Mol. Biol.*, 254:392-403 (1995).
Yates et. al., Inhibition of bone resorption by inorganic phosphate in mediated by both reduced osteoclast formation and decreased activity of mature osteoclasts. *J. Bone Miner. Res.*, 6(5): 476-8 (1990).
Yerges et. al., NCBI Sequence Database Accession No. NM_001203, Jul. 12, 2009.
Yerges et. al., NCBI Sequence Database Accession No. NP_001194, Jul. 12, 2009.
Yoshida et. al., Osteoinduction capability of recombinant human bone morphogenetic protein-2 in intramuscular and subcutaneous sites: An experimental study. *J. Cranio-Maxillofac. Surg.*, 26: 112-5 (1998).
Zambaux et. al., Influence of experimental parameters on the characteristics of poly(lactic acid) nanoparticles prepared by a double emulsion method. *J. Controlled Rel.*, 50(1-3):31-40 (1998).
Zhang et. al., Humanization of an anti-human TNF-β antibody by variable region resurfacing with the aid of molecular modeling. *Molec. Immunol.*, 42(12):1445-51 (2005).
Zimmerman et. al., The spemann organizer signal noggin binds and inactives bone morphogenetic protein 4. *Cell*, 86(4):599-606 (1996).
Zlotogora et. al., Dominance and homozygosity, *Am. J. Med. Genet.*, 68: 412-6 (1997).
zur Muhlen et. al., Solid lipid nanoparticles (SLN) for controlled drug delivery—Drug release and release mechanism. *Eur. J. Pharm. Biopharm.*, 45(2):149-55 (1998).
Annex regarding the purported relevance of gene/peptides mentioned by Professor Arnett, dated Mar. 18, 2011.
Declaration of Dr. Martyn Robinson, submitted in Opposition to European Patent No. 1133558, dated Jan. 13, 2008.
Declaration of Dr. Mary E. Brunkow, submitted in Opposition to European Patent No. 1133558, dated Jan. 9, 2008.

* cited by examiner

SEQUENCE LISTING

<160> NUMBER OF SEQ ID NOS: 248

<210> SEQ ID NO 1
<211> LENGTH: 13
<212> TYPE: PRT
<213> ORGANISM: Artificial Sequence
<220> FEATURE:
<223> OTHER INFORMATION: Ab-A & Ab-1 LCDR1

<400> SEQUENCE: 1

Gln Ser Ser Gln Ser Val Tyr Asp Asn Asn Trp Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Ab-A and Ab-1 LCDR2

<400> SEQUENCE: 2

Asp Ala Ser Asp Leu Ala Ser
1               5

<210> SEQ ID NO 3
<211> LENGTH: 10
<212> TYPE: PRT
<213> ORGANISM: Artificial Sequence
<220> FEATURE:
<223> OTHER INFORMATION: Ab-A and Ab-1 LCDR3

<400> SEQUENCE: 3

Gln Gly Ala Tyr Asn Asp Val Ile Tyr Ala
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Ab-A and Ab-1 HCDR1

<400> SEQUENCE: 4

Ser Tyr Trp Met Asn
1               5

<210> SEQ ID NO 5
<211> LENGTH: 16
<212> TYPE: PRT
<213> ORGANISM: Artificial Sequence
<220> FEATURE:
<223> OTHER INFORMATION: Ab-1 and Ab-2 HCDR2

<400> SEQUENCE: 5

Thr Ile Asp Ser Gly Gly Arg Thr Asp Tyr Ala Ser Trp Ala Lys Gly
1               5                   10                  15

<210> SEQ ID NO 6
<211> LENGTH: 4
<212> TYPE: PRT
<213> ORGANISM: Artificial Sequence
<220> FEATURE:
<223> OTHER INFORMATION: Ab-A and Ab-1 HCDR3

<400> SEQUENCE: 6

Asn Trp Asn Leu
1

<210> SEQ ID NO 7
<211> LENGTH: 654
<212> TYPE: DNA
<213> ORGANISM: Artificial Sequence
<220> FEATURE:
<223> OTHER INFORMATION: Rabbit-Mouse Chimera
<220> FEATURE:
<221> NAME/KEY: misc_feature
<223> OTHER INFORMATION: Ab-A light chain (no signal)

<400> SEQUENCE: 7

```
gcgcaagtgc tgacccagac tccagcctcc gtgtctgcag ctgtgggagg cacagtcacc    60
atcaattgcc agtccagtca gagtgtttat gataacaact ggttagcctg gtttcagcag   120
aaaccagggc agcctcccaa gctcctgatt tatgatgcat ccgatctggc atctggggtc   180
ccatcgcggt tcagtggcag tggatctggg acacagttca ctctcaccat cagcggcgtg   240
cagtgtgccg atgctgccac ttactactgt caaggcgctt ataatgatgt tatttatgct   300
ttcggcggag ggaccgaggt ggtggtcaaa cgtacggatg ctgcaccaac tgtatccatc   360
ttcccaccat ccagtgagca gttaacatct ggaggtgcct cagtcgtgtg cttcttgaac   420
aacttctacc ccaaagacat caatgtcaag tggaagattg atggcagtga acgacaaaat   480
ggcgtcctga acagttggac tgatcaggac agcaaagaca gcacctacag catgagcagc   540
accctcacgt tgaccaagga cgagtatgaa cgacataaca gctatacctg tgaggccact   600
cacaagacat caacttcacc cattgtcaag agcttcaaca ggaatgagtg ttag         654
```

<210> SEQ ID NO 8
<211> LENGTH: 217
<212> TYPE: PRT
<213> ORGANISM: Artificial Sequence
<220> FEATURE:
<223> OTHER INFORMATION: Rabbit-Mouse Chimera
<220> FEATURE:
<221> NAME/KEY: MISC_FEATURE
<223> OTHER INFORMATION: Ab-A light chain (no signal)

<400> SEQUENCE: 8

Ala Gln Val Leu Thr Gln Thr Pro Ala Ser Val Ser Ala Ala Val Gly
1               5                   10                  15

Gly Thr Val Thr Ile Asn Cys Gln Ser Ser Gln Ser Val Tyr Asp Asn
                20                  25                  30

Asn Trp Leu Ala Trp Phe Gln Gln Lys Pro Gly Gln Pro Pro Lys Leu
            35                  40                  45

Leu Ile Tyr Asp Ala Ser Asp Leu Ala Ser Gly Val Pro Ser Arg Phe
        50                  55                  60

Ser Gly Ser Gly Ser Gly Thr Gln Phe Thr Leu Thr Ile Ser Gly Val
65                  70                  75                  80

Gln Cys Ala Asp Ala Ala Thr Tyr Tyr Cys Gln Gly Ala Tyr Asn Asp
                85                  90                  95

Val Ile Tyr Ala Phe Gly Gly Gly Thr Glu Val Val Val Lys Arg Thr
                100                 105                 110

Asp Ala Ala Pro Thr Val Ser Ile Phe Pro Pro Ser Ser Glu Gln Leu
            115                 120                 125

Thr Ser Gly Gly Ala Ser Val Val Cys Phe Leu Asn Asn Phe Tyr Pro
        130                 135                 140

Lys Asp Ile Asn Val Lys Trp Lys Ile Asp Gly Ser Glu Arg Gln Asn
145                 150                 155                 160

```
Gly Val Leu Asn Ser Trp Thr Asp Gln Asp Ser Lys Asp Ser Thr Tyr
            165                 170                 175
Ser Met Ser Ser Thr Leu Thr Leu Thr Lys Asp Glu Tyr Glu Arg His
        180                 185                 190
Asn Ser Tyr Thr Cys Glu Ala Thr His Lys Thr Ser Thr Ser Pro Ile
    195                 200                 205
Val Lys Ser Phe Asn Arg Asn Glu Cys
210                 215

<210> SEQ ID NO 9
<211> LENGTH: 1302
<212> TYPE: DNA
<213> ORGANISM: Artificial Sequence
<220> FEATURE:
<223> OTHER INFORMATION: Humanized Antibody
<220> FEATURE:
<221> NAME/KEY: misc_feature
<223> OTHER INFORMATION: Ab-A heavy chain (no signal)

<400> SEQUENCE: 9
cagtcgctgg aggagtccgg gggtcgcctg gtcacgcctg gacacccct gacactcacc      60
tgcacagcct ctggattctc cctcagtagt tattggatga ctgggtccg ccaggctcca    120
ggggaggggc tggaatggat cggaaccatt gattctggtg gtaggacgga ctacgcgagc   180
tgggcaaaag gccgattcac catctccaga acctcgacta cgatggatct gaaaatgacc   240
agtctgacga ccggggacac ggcccgttat ttctgtgcca gaaattggaa cttgtggggc   300
caaggcaccc tcgtcaccgt ctcgagcgct tctacaaagg gcccatctgt ctatccactg   360
gcccctggat ctgctgccca aactaactcc atggtgaccc tgggatgcct ggtcaagggc   420
tatttccctg agccagtgac agtgacctgg aactctggat ccctgtccag cggtgtgcac   480
accttcccag ctgtcctgca gtctgacctc tacactctga gcagtcagt gactgtcccc    540
tccagcacct ggcccagcga gaccgtcacc tgcaacgttg cccacccggc agcagcacc    600
aaggtggaca gaaaaattgt gcccagggat gtggttgta agccttgcat atgtacagtc    660
ccagaagtat catctgtctt catcttcccc caaagcccca aggatgtgct caccattact   720
ctgactccta aggtcacgtg tgttgtggta gacatcagca aggatgatcc cgaggtccag   780
ttcagctggt ttgtagatga tgtggaggtg cacacagctc agacgcaacc ccggaggag   840
cagttcaaca gcactttccg ctcagtcagt gaacttccca tcatgcacca ggactggctc   900
aatggcaagg agttcaaatg cagggtcaac agtgcagctt ccctgccccc atcgagaaa    960
accatctcca aaccaaaagg cagaccgaag gctccacagg tgtacaccat tccacctccc  1020
aaggagcaga tggccaagga taaagtcagt ctgacctgca tgataacaga cttcttccct  1080
gaagacatta ctgtggagtg gcagtggaat gggcagccag cggagaacta caagaacact  1140
cagcccatca tggacacaga tggctcttac ttcgtctaca gcaagctcaa tgtgcagaag  1200
agcaactggg aggcaggaaa tactttcacc tgctctgtgt acatgagggg cctgcacaac  1260
caccatactg agaagagcct ctcccactct cctggtaaat ga                     1302

<210> SEQ ID NO 10
<211> LENGTH: 433
<212> TYPE: PRT
<213> ORGANISM: Artificial Sequence
<220> FEATURE:
<223> OTHER INFORMATION: Humanized antibody
<220> FEATURE:
<221> NAME/KEY: MISC_FEATURE
<223> OTHER INFORMATION: Ab-A heavy chain (no signal)
```

<400> SEQUENCE: 10

```
Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Trp
            20                  25                  30

Met Asn Trp Val Arg Gln Ala Pro Gly Glu Gly Leu Glu Trp Ile Gly
        35                  40                  45

Thr Ile Asp Ser Gly Gly Arg Thr Asp Tyr Ala Ser Trp Ala Lys Gly
50                  55                  60

Arg Phe Thr Ile Ser Arg Thr Ser Thr Thr Met Asp Leu Lys Met Thr
65                  70                  75                  80

Ser Leu Thr Thr Gly Asp Thr Ala Arg Tyr Phe Cys Ala Arg Asn Trp
                85                  90                  95

Asn Leu Trp Gly Gln Gly Thr Leu Val Thr Val Ser Ser Ala Ser Thr
            100                 105                 110

Lys Gly Pro Ser Val Tyr Pro Leu Ala Pro Gly Ser Ala Ala Gln Thr
        115                 120                 125

Asn Ser Met Val Thr Leu Gly Cys Leu Val Lys Gly Tyr Phe Pro Glu
130                 135                 140

Pro Val Thr Val Thr Trp Asn Ser Gly Ser Leu Ser Ser Gly Val His
145                 150                 155                 160

Thr Phe Pro Ala Val Leu Gln Ser Asp Leu Tyr Thr Leu Ser Ser Ser
                165                 170                 175

Val Thr Val Pro Ser Ser Thr Trp Pro Ser Glu Thr Val Thr Cys Asn
            180                 185                 190

Val Ala His Pro Ala Ser Ser Thr Lys Val Asp Lys Lys Ile Val Pro
        195                 200                 205

Arg Asp Cys Gly Cys Lys Pro Cys Ile Cys Thr Val Pro Glu Val Ser
210                 215                 220

Ser Val Phe Ile Phe Pro Pro Lys Pro Lys Asp Val Leu Thr Ile Thr
225                 230                 235                 240

Leu Thr Pro Lys Val Thr Cys Val Val Val Asp Ile Ser Lys Asp Asp
                245                 250                 255

Pro Glu Val Gln Phe Ser Trp Phe Val Asp Asp Val Glu Val His Thr
            260                 265                 270

Ala Gln Thr Gln Pro Arg Glu Glu Gln Phe Asn Ser Thr Phe Arg Ser
        275                 280                 285

Val Ser Glu Leu Pro Ile Met His Gln Asp Trp Leu Asn Gly Lys Glu
290                 295                 300

Phe Lys Cys Arg Val Asn Ser Ala Ala Phe Pro Ala Pro Ile Glu Lys
305                 310                 315                 320

Thr Ile Ser Lys Thr Lys Gly Arg Pro Lys Ala Pro Gln Val Tyr Thr
                325                 330                 335

Ile Pro Pro Pro Lys Glu Gln Met Ala Lys Asp Lys Val Ser Leu Thr
            340                 345                 350

Cys Met Ile Thr Asp Phe Phe Pro Glu Asp Ile Thr Val Glu Trp Gln
        355                 360                 365

Trp Asn Gly Gln Pro Ala Glu Asn Tyr Lys Asn Thr Gln Pro Ile Met
370                 375                 380

Asn Thr Asn Gly Ser Tyr Phe Val Tyr Ser Lys Leu Asn Val Gln Lys
385                 390                 395                 400

Ser Asn Trp Glu Ala Gly Asn Thr Phe Thr Cys Ser Val Leu His Glu
```

405                 410                 415
Gly Leu His Asn His Thr Glu Lys Ser Leu Ser His Ser Pro Gly
            420                 425                 430

Lys

<210> SEQ ID NO 11
<211> LENGTH: 390
<212> TYPE: DNA
<213> ORGANISM: Artificial Sequence
<220> FEATURE:
<223> OTHER INFORMATION: Humanized antibody
<220> FEATURE:
<221> NAME/KEY: misc_feature
<223> OTHER INFORMATION: Ab-1 light variable (with signal)

<400> SEQUENCE: 11
atggacacga gggcccccac tcagctgctg gggctcctgc tgctctggct cccaggtgcc      60
acatttgctc aagttctgac ccagagtcca agcagtctct ccgccagcgt aggcgatcgt     120
gtgactatta cctgtcaatc tagtcagagc gtgtatgata caattggct ggcgtggtac      180 cagcaaaaac cgggcaaagc cccgaagctg ctcatctatg acgcgtccga tctggctagc     240
ggtgtgccaa gccgtttcag tggcagtggc agcggtactg actttaccct cacaatttcg     300
tctctccagc cggaagattt cgccacttac tattgtcaag gtgcttacaa cgatgtgatt     360
tatgccttcg gtcagggcac taaagtagaa                                      390

<210> SEQ ID NO 12
<211> LENGTH: 133
<212> TYPE: PRT
<213> ORGANISM: Artificial Sequence
<220> FEATURE:
<223> OTHER INFORMATION: Humanized antibody
<220> FEATURE:
<221> NAME/KEY: MISC_FEATURE
<223> OTHER INFORMATION: Ab-1 light variable (with signal)

<400> SEQUENCE: 12

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Ser Pro Ser Ser
            20                  25                  30

Leu Ser Ala Ser Val Gly Asp Arg Val Thr Ile Thr Cys Gln Ser Ser
        35                  40                  45

Gln Ser Val Tyr Asp Asn Asn Trp Leu Ala Trp Tyr Gln Gln Lys Pro
    50                  55                  60

Gly Lys Ala Pro Lys Leu Leu Ile Tyr Asp Ala Ser Asp Leu Ala Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln Gly Ala Tyr Asn Asp Val Ile Tyr Ala Phe Gly Gln Gly Thr Lys
        115                 120                 125

Val Glu Ile Lys Arg
    130

<210> SEQ ID NO 13
<211> LENGTH: 393
<212> TYPE: DNA
<213> ORGANISM: Artificial Sequence
<220> FEATURE:
<223> OTHER INFORMATION: Humanized antibody
<220> FEATURE:
<221> NAME/KEY: misc_feature
<223> OTHER INFORMATION: Ab-1 heavy variable (with signal)

<400> SEQUENCE: 13

```
atggagactg ggctgcgctg gcttctcctg gtcgctgtgc tcaaaggtgt ccactgtgag      60
gtgcagctgt tggagtctgg aggcgggctt gtccagcctg agggagcct gcgtctctct     120
tgtgcagcaa gcggcttcag cttatcctct tactggatga attgggtgcg gcaggcacct     180
gggaagggcc tggagtgggt gggcaccatt gattccggag ccgtacaga ctacgcgtct     240
tgggcaaagg gccgtttcac catttcccgc gacaactcca aaataccat gtacctccag     300
atgaactctc tccgcgcaga ggacacagca cgttattact gtgcacgcaa ctggaatctg     360
tggggtcaag gtactcttgt aacagtctcg agc                                  393
```

<210> SEQ ID NO 14
<211> LENGTH: 131
<212> TYPE: PRT
<213> ORGANISM: Artificial Sequence
<220> FEATURE:
<223> OTHER INFORMATION: Humanized antibody

<400> SEQUENCE: 14

```
Met Glu Thr Gly Leu Arg Trp Leu Leu Leu Val Ala Val Leu Lys Gly
1               5                   10                  15
Val His Cys Glu Val Gln Leu Leu Glu Ser Gly Gly Gly Leu Val Gln
            20                  25                  30
Pro Gly Gly Ser Leu Arg Leu Ser Cys Ala Ala Ser Gly Phe Ser Leu
        35                  40                  45
Ser Ser Tyr Trp Met Asn Trp Val Arg Gln Ala Pro Gly Lys Gly Leu
    50                  55                  60
Glu Trp Val Gly Thr Ile Asp Ser Gly Gly Arg Thr Asp Tyr Ala Ser
65                  70                  75                  80
Trp Ala Lys Gly Arg Phe Thr Ile Ser Arg Asp Asn Ser Lys Asn Thr
                85                  90                  95
Met Tyr Leu Gln Met Asn Ser Leu Arg Ala Glu Asp Thr Ala Arg Tyr
            100                 105                 110
Tyr Cys Ala Arg Asn Trp Asn Leu Trp Gly Gln Gly Thr Leu Val Thr
        115                 120                 125
Val Ser Ser
    130
```

<210> SEQ ID NO 15
<211> LENGTH: 10
<212> TYPE: PRT
<213> ORGANISM: Artificial Sequence
<220> FEATURE:
<223> OTHER INFORMATION: Ab-B LCDR1

<400> SEQUENCE: 15

```
Ser Ala Ser Ser Ser Val Ser Phe Val Asp
1               5                   10
```

<210> SEQ ID NO 16
<211> LENGTH: 7
<212> TYPE: PRT
<213> ORGANISM: Artificial Sequence
<220> FEATURE:
<223> OTHER INFORMATION: Ab-B LCDR2

```
<400> SEQUENCE: 16

Arg Thr Ser Asn Leu Gly Phe
1               5

<210> SEQ ID NO 17
<211> LENGTH: 9
<212> TYPE: PRT
<213> ORGANISM: Artificial Sequence
<220> FEATURE:
<223> OTHER INFORMATION: LCDR3

<400> SEQUENCE: 17

Gln Gln Arg Ser Thr Tyr Pro Pro Thr
1               5

<210> SEQ ID NO 18
<211> LENGTH: 7
<212> TYPE: PRT
<213> ORGANISM: Artificial Sequence
<220> FEATURE:
<223> OTHER INFORMATION: Ab-B HCDR1

<400> SEQUENCE: 18

Thr Ser Gly Met Gly Val Gly
1               5

<210> SEQ ID NO 19
<211> LENGTH: 16
<212> TYPE: PRT
<213> ORGANISM: Artificial Sequence
<220> FEATURE:
<223> OTHER INFORMATION: Ab-B HCDR2

<400> SEQUENCE: 19

His Ile Trp Trp Asp Asp Val Lys Arg Tyr Asn Pro Val Leu Lys Ser
1               5                   10                  15

<210> SEQ ID NO 20
<211> LENGTH: 14
<212> TYPE: PRT
<213> ORGANISM: Artificial Sequence
<220> FEATURE:
<223> OTHER INFORMATION: Ab-B HCDR3

<400> SEQUENCE: 20

Glu Asp Phe Asp Tyr Asp Glu Glu Tyr Tyr Ala Met Asp Tyr
1               5                   10

<210> SEQ ID NO 21
<211> LENGTH: 642
<212> TYPE: DNA
<213> ORGANISM: Mus musculus
<220> FEATURE:
<221> NAME/KEY: misc_feature
<223> OTHER INFORMATION: Ab-B light chain (no signal)

<400> SEQUENCE: 21
caaattgttc tcacccagtc tccaacaatc gtgtctgcat ctccagggga gaaggtcacc      60
ctaatctgca gtgccagttc aagtgtaagt ttcgtggact ggttccagca gaagccaggc     120
acttctccca aacgctggat ttacagaaca tccaacctgg ttttggagt ccctgctcgc      180 ttcagtggcg gtggatctgg gacctctcac tctctcacaa tcagccgaat ggaggctgaa     240
gatgctgcca cttattactg ccagcaaagg agtacttacc cacccacgtt cggtgctggg     300
```

```
accaagctgg aactgaaacg ggctgatgct gcaccaactg tatccatctt cccaccatcc    360
agtgagcagt taacatctgg aggtgcctca gtcgtgtgct tcttgaacaa cttctacccc    420
aaagacatca atgtcaagtg gaagattgat ggcagtgaac gacaaaatgg cgtcctgaac    480
agttggactg atcaggacag caaagacagc acctacagca tgagcagcac cctcacgttg    540
accaaggacg agtatgaacg acataacagc tatacctgtg aggccactca caagacatca    600
acttcaccca ttgtcaagag cttcaacagg aatgagtgtt ag                       642
```

```
<210> SEQ ID NO 22
<211> LENGTH: 213
<212> TYPE: PRT
<213> ORGANISM: Mus musculus
<220> FEATURE:
<221> NAME/KEY: MISC_FEATURE
<223> OTHER INFORMATION: Ab-B light chain (no signal)

<400> SEQUENCE: 22
```

```
Gln Ile Val Leu Thr Gln Ser Pro Thr Ile Val Ser Ala Ser Pro Gly
 1               5                  10                  15

Glu Lys Val Thr Leu Ile Cys Ser Ala Ser Ser Ser Val Ser Phe Val
             20                  25                  30

Asp Trp Phe Gln Gln Lys Pro Gly Thr Ser Pro Lys Arg Trp Ile Tyr
         35                  40                  45

Arg Thr Ser Asn Leu Gly Phe Gly Val Pro Ala Arg Phe Ser Gly Gly
     50                  55                  60

Gly Ser Gly Thr Ser His Ser Leu Thr Ile Ser Arg Met Glu Ala Glu
 65                  70                  75                  80

Asp Ala Ala Thr Tyr Tyr Cys Gln Gln Arg Ser Thr Tyr Pro Pro Thr
                 85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```

```
<210> SEQ ID NO 23
<211> LENGTH: 1350
<212> TYPE: DNA
<213> ORGANISM: Mus musculus
<220> FEATURE:
<221> NAME/KEY: misc_feature
<223> OTHER INFORMATION: Ab-B heavy chain (no signal)

<400> SEQUENCE: 23
caggttactc tgaaagagtc tggccctggg atattgcagc cctcccagac cctcagtctg     60
acttgttctt tctctgggtt ttcactgagc acttctggta tgggtgtagg ctggattcgt    120
```

```
cacccatcag ggaagaatct ggagtggctg gcacacattt ggtgggatga tgtcaagcgc      180
tataacccag tcctgaagag ccgactgact atctccaagg atacctccaa cagccaggta      240
ttcctcaaga tcgccaatgt ggacactgca gatactgcca catactactg tgctcgaata      300
gaggactttg attacgacga ggagtattat gctatggact actggggtca aggaacctca      360
gtcatcgtct cctcagccaa aacgacaccc ccatctgtct atccactggc ccctggatct      420
gctgcccaaa ctaactccat ggtgaccctg ggatgcctgg tcaagggcta tttccctgag      480
ccagtgacag tgacctggaa ctctggatcc ctgtccagcg gtgtgcacac cttcccagct      540
gtcctgcagt ctgacctcta cactctgagc agctcagtga ctgtcccctc cagcacctgg      600
cccagcgaga ccgtcacctg caacgttgcc cacccggcca gcagcaccaa ggtggacaag      660
aaaattgtgc caggggattg tggttgtaag ccttgcatat gtacagtccc agaagtatca      720
tctgtcttca tcttcccccc aaagcccaag gatgtgctca ccattactct gactcctaag      780
gtcacgtgtg ttgtggtaga catcagcaag gatgatcccg aggtccagtt cagctggttt      840
gtagatgatg tggaggtgca cacagctcag acgcaaccc gggaggagca gttcaacagc      900
actttccgct cagtcagtga acttcccatc atgcaccagg actggctcaa tggcaaggag      960
ttcaaatgca gggtcaacag tgcagctttc cctgcccca tcgagaaaac catctccaaa     1020
accaaaggca gaccgaaggc tccacaggtg tacaccattc cacctcccaa ggagcagatg     1080
gccaaggata agtcagtctc gacctgcatg ataacagact tcttccctga agacattact     1140
gtggagtggc agtggaatgg gcagccagcg gagaactaca agaacactca gcccatcatg     1200
gacacagatg gctcttactt cgtctacagc aagctcaatg tgcagaagag caactgggag     1260
gcaggaaata ctttcacctg ctctgtgtta catgagggcc tgcacaacca ccatactgag     1320
aagagcctct cccactctcc tggtaaatga                                     1350
```

<210> SEQ ID NO 24  
<211> LENGTH: 449  
<212> TYPE: PRT  
<213> ORGANISM: Mus musculus  
<220> FEATURE:  
<221> NAME/KEY: MISC_FEATURE  
<223> OTHER INFORMATION: Ab-B heavy chain (no signal)

<400> SEQUENCE: 24

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg His Pro Ser Gly Lys Asn Leu Glu
        35                  40                  45

Trp Leu Ala His Ile Trp Trp Asp Asp Val Lys Arg Tyr Asn Pro Val
    50                  55                  60

Leu Lys Ser Arg Leu Thr Ile Ser Lys Asp Thr Ser Asn Ser Gln Val
65                  70                  75                  80

Phe Leu Lys Ile Ala Asn Val Asp Thr Ala Asp Thr Ala Thr Tyr Tyr
                85                  90                  95

Cys Ala Arg Ile Glu Asp Phe Asp Tyr Asp Glu Glu Tyr Tyr Ala Met
            100                 105                 110

Asp Tyr Trp Gly Gln Gly Thr Ser Val Ile Val Ser Ser Ala Lys Thr
        115                 120                 125

Thr Pro Pro Ser Val Tyr Pro Leu Ala Pro Gly Ser Ala Ala Gln Thr
```

```
            130                 135                 140
Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Pro Ser Ser Thr Trp Pro Ser Glu Thr Val Thr Cys Asn
        195                 200                 205

Val Ala His Pro Ala Ser Ser Thr Lys Val Asp Lys Lys Ile Val Pro
    210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
            260                 265                 270

Pro Glu Val Gln Phe Ser Trp Phe Val Asp Asp Val Glu Val His Thr
        275                 280                 285

Ala Gln Thr Gln Pro Arg Glu Glu Gln Phe Asn Ser Thr Phe Arg Ser
    290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
            340                 345                 350

Ile Pro Pro Pro Lys Glu Gln Met Ala Lys Asp Lys Val Ser Leu Thr
        355                 360                 365

Cys Met Ile Thr Asp Phe Phe Pro Glu Asp Ile Thr Val Glu Trp Gln
    370                 375                 380

Trp Asn Gly Gln Pro Ala Glu Asn Tyr Lys Asn Thr Gln Pro Ile Met
385                 390                 395                 400

Asp Thr Asp Gly Ser Tyr Phe Val Tyr Ser Lys Leu Asn Val Gln Lys
                405                 410                 415

Ser Asn Trp Glu Ala Gly Asn Thr Phe Thr Cys Ser Val Leu His Glu
            420                 425                 430

Gly Leu His Asn His His Thr Glu Lys Ser Leu Ser His Ser Pro Gly
        435                 440                 445

Lys

<210> SEQ ID NO 25
<211> LENGTH: 15
<212> TYPE: PRT
<213> ORGANISM: Artificial Sequence
<220> FEATURE:
<223> OTHER INFORMATION: Ab-C LCDR1

<400> SEQUENCE: 25

Lys Ala Ser Gln Ser Val Asp Tyr Asp Gly Asp Ser Tyr Met Asn
1               5                   10                  15

<210> SEQ ID NO 26
<211> LENGTH: 7
<212> TYPE: PRT
<213> ORGANISM: Artificial Sequence
```

```
<220> FEATURE:
<223> OTHER INFORMATION: Ab-C LCDR2

<400> SEQUENCE: 26

Ala Ala Ser Asn Leu Glu Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Ab-C LCDR3

<400> SEQUENCE: 27

Gln Gln Ser Asn Glu Asp Pro Trp Thr
1               5

<210> SEQ ID NO 28
<211> LENGTH: 5
<212> TYPE: PRT
<213> ORGANISM: Artificial Sequence
<220> FEATURE:
<223> OTHER INFORMATION: Ab-C HCDR1

<400> SEQUENCE: 28

Asp Cys Tyr Met Asn
1               5

<210> SEQ ID NO 29
<211> LENGTH: 17
<212> TYPE: PRT
<213> ORGANISM: Artificial Sequence
<220> FEATURE:
<223> OTHER INFORMATION: Ab-C HCDR2

<400> SEQUENCE: 29

Asp Ile Asn Pro Phe Asn Gly Gly Thr Thr Tyr Asn Gln Lys Phe Lys
1               5                   10                  15
Gly

<210> SEQ ID NO 30
<211> LENGTH: 16
<212> TYPE: PRT
<213> ORGANISM: Artificial Sequence
<220> FEATURE:
<223> OTHER INFORMATION: Ab-C HCDR3

<400> SEQUENCE: 30

Ser His Tyr Tyr Phe Asp Gly Arg Val Pro Trp Asp Ala Met Asp Tyr
1               5                   10                  15

<210> SEQ ID NO 31
<211> LENGTH: 657
<212> TYPE: DNA
<213> ORGANISM: Mus musculus
<220> FEATURE:
<221> NAME/KEY: misc_feature
<223> OTHER INFORMATION: Ab-C light chain (no signal)

<400> SEQUENCE: 31
gacattgtgc tgacccaatc tccagcttct ttgactgtgt ctctaggcct gagggccacc      60
atctcctgca aggccagcca aagtgttgat tatgatggtg atagttatat gaactggtac     120
cagcagaaac caggacagcc acccaaactc ctcatctatg ctgcatccaa tctagaatct     180
```

```
gggatcccag ccaggtttag tggcaatggg tctgggacag acttcaccct caacatccat      240
cctgtggagg aggaggatgc tgtaacctat tactgtcaac aaagtaatga ggatccgtgg      300
acgttcggtg gaggcaccaa gctggaaatc aaacgggctg atgctgcacc aactgtatcc      360
atcttcccac catccagtga gcagttaaca tctggaggtg cctcagtcgt gtgcttcttg      420
aacaacttct accccaaaga catcaatgtc aagtggaaga ttgatggcag tgaacgacaa      480
aatggcgtcc tgaacagttg gactgatcag gacagcaaag acagcaccta cagcatgagc      540
agcaccctca cgttgaccaa ggacgagtat gaacgacata cagctatac ctgtgaggcc      600 actcacaaga catcaacttc acccattgtc aagagcttca caggaatga gtgttag        657
```

```
<210> SEQ ID NO 32
<211> LENGTH: 218
<212> TYPE: PRT
<213> ORGANISM: Mus musculus
<220> FEATURE:
<221> NAME/KEY: MISC_FEATURE
<223> OTHER INFORMATION: Ab-C light chain (no signal)

<400> SEQUENCE: 32
```

```
Asp Ile Val Leu Thr Gln Ser Pro Ala Ser Leu Thr Val Ser Leu Gly
1               5                   10                  15

Leu Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Asn Gly Ser Gly Thr Asp Phe Thr Leu Asn Ile His
65                  70                  75                  80

Pro Val Glu Glu Glu Asp Ala Val Thr Tyr Tyr Cys Gln Gln Ser Asn
                85                  90                  95

Glu Asp Pro Trp Thr Phe Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215
```

```
<210> SEQ ID NO 33
<211> LENGTH: 1350
<212> TYPE: DNA
<213> ORGANISM: Mus musculus
<220> FEATURE:
<221> NAME/KEY: misc_feature
<223> OTHER INFORMATION: Ab-C heavy chain (no signal)

<400> SEQUENCE: 33
```

```
gaggtccagc tgcaacaatc tggacctgag ctggtgaagc ctgggacttc agtgaagatg      60
tcctgtaagg cttctggata cacattcact gactgctaca tgaactgggt gaagcagagc     120
catgggaaga gccttgaatg gattggagat attaatcctt caacggtgg tactacctac      180
aaccagaagt tcaagggcaa ggccacattg actgtagaca atcctccag cacagcctac      240
atgcagctca cagcctgac atctgacgac tctgcagtct attactgtgc aagatcccat      300
tattacttcg atggtagagt cccttgggat gctatggact actggggtca aggaacctca      360
gtcaccgtct cctcagccaa aacgacaccc ccatctgtct atccactggc ccctggatct      420
gctgcccaaa ctaactccat ggtgaccctg ggatgcctgg tcaagggcta tttccctgag      480
ccagtgacag tgacctggaa ctctggatcc ctgtccagcg gtgtgcacac cttcccagct      540
gtcctgcagt ctgacctcta cactctgagc agctcagtga ctgtcccctc agcacctgg      600
cccagcgaga ccgtcacctg caacgttgcc cacccggcca gcagcaccaa ggtggacaag      660
aaaattgtgc cagggattg tggttgtaag ccttgcatat gtacagtccc agaagtatca      720
tctgtcttca tcttcccccc aaagcccaag gatgtgctca ccattactct gactcctaag      780
gtcacgtgtg ttgtggtaga catcagcaag gatgatcccg aggtccagtt cagctggttt      840
gtagatgatg tggaggtgca cacagctcag acgcaacccc gggaggagca gttcaacagc      900
actttccgct cagtcagtga acttcccatc atgcaccagg actggctcaa tggcaaggag      960
ttcaaatgca gggtcaacag tgcagctttc cctgccccca tcgagaaaac catctccaaa     1020
accaaaggca gaccgaaggc tccacaggtg tacaccattc cacctcccaa ggagcagatg     1080
gccaaggata aagtcagtct gacctgcatg ataacagact tcttccctga agacattact     1140
gtggagtggc agtggaatgg gcagccagcg gagaactaca agaacactca gcccatcatg     1200
gacacagatg gctcttactt catctacagc aagctcaatg tgcagaagag caactgggag     1260
gcaggaaata ctttcacctg ctctgtgtta catgagggcc tgcacaacca ccatactgag     1320
aagagcctct cccactctcc tggtaaatga                                       1350
```

<210> SEQ ID NO 34
<211> LENGTH: 449
<212> TYPE: PRT
<213> ORGANISM: Mus musculus
<220> FEATURE:
<221> NAME/KEY: MISC_FEATURE
<223> OTHER INFORMATION: Ab-C heavy chain (no signal)

<400> SEQUENCE: 34

```
Glu Val Gln Leu Gln Gln Ser Gly Pro Glu Leu Val Lys Pro Gly Thr
1               5                   10                  15

Ser Val Lys Met Ser Cys Lys Ala Ser Gly Tyr Thr Phe Thr Asp Cys
            20                  25                  30

Tyr Met Asn Trp Val Lys Gln Ser His Gly Lys Ser Leu Glu Trp Ile
        35                  40                  45

Gly Asp Ile Asn Pro Phe Asn Gly Gly Thr Thr Tyr Asn Gln Lys Phe
    50                  55                  60

Lys Gly Lys Ala Thr Leu Thr Val Asp Lys Ser Ser Thr Ala Tyr
65                  70                  75                  80

Met Gln Leu Asn Ser Leu Thr Ser Asp Asp Ser Ala Val Tyr Tyr Cys
                85                  90                  95

Ala Arg Ser His Tyr Tyr Phe Asp Gly Arg Val Pro Trp Asp Ala Met
            100                 105                 110
```

```
Asp Tyr Trp Gly Gln Gly Thr Ser Val Thr Val Ser Ser Ala Lys Thr
            115                 120                 125

Thr Pro Pro Ser Val Tyr Pro Leu Ala Pro Gly Ser Ala Ala Gln Thr
130                 135                 140

Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Pro Ser Ser Thr Trp Pro Ser Glu Thr Val Thr Cys Asn
        195                 200                 205

Val Ala His Pro Ala Ser Ser Thr Lys Val Asp Lys Lys Ile Val Pro
    210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
            260                 265                 270

Pro Glu Val Gln Phe Ser Trp Phe Val Asp Asp Val Glu Val His Thr
        275                 280                 285

Ala Gln Thr Gln Pro Arg Glu Glu Gln Phe Asn Ser Thr Phe Arg Ser
    290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
            340                 345                 350

Ile Pro Pro Pro Lys Glu Gln Met Ala Lys Asp Lys Val Ser Leu Thr
        355                 360                 365

Cys Met Ile Thr Asp Phe Phe Pro Glu Asp Ile Thr Val Glu Trp Gln
370                 375                 380

Trp Asn Gly Gln Pro Ala Glu Asn Tyr Lys Asn Thr Gln Pro Ile Met
385                 390                 395                 400

Asp Thr Asp Gly Ser Tyr Phe Ile Tyr Ser Lys Leu Asn Val Gln Lys
                405                 410                 415

Ser Asn Trp Glu Ala Gly Asn Thr Phe Thr Cys Ser Val Leu His Glu
            420                 425                 430

Gly Leu His Asn His His Thr Glu Lys Ser Leu Ser His Ser Pro Gly
        435                 440                 445

Lys

<210> SEQ ID NO 35
<211> LENGTH: 11
<212> TYPE: PRT
<213> ORGANISM: Artificial Sequence
<220> FEATURE:
<223> OTHER INFORMATION: Ab-D LCDR1

<400> SEQUENCE: 35

Gln Ala Ser Gln Gly Thr Ser Ile Asn Leu Asn
1               5                   10
```

```
<210> SEQ ID NO 36
<211> LENGTH: 7
<212> TYPE: PRT
<213> ORGANISM: Artificial Sequence
<220> FEATURE:
<223> OTHER INFORMATION: Ab-D LCDR2

<400> SEQUENCE: 36

Gly Ser Ser Asn Leu Glu Asp
1               5

<210> SEQ ID NO 37
<211> LENGTH: 9
<212> TYPE: PRT
<213> ORGANISM: Artificial Sequence
<220> FEATURE:
<223> OTHER INFORMATION: Ab-D LCDR3

<400> SEQUENCE: 37

Leu Gln His Ser Tyr Leu Pro Tyr Thr
1               5

<210> SEQ ID NO 38
<211> LENGTH: 5
<212> TYPE: PRT
<213> ORGANISM: Artificial Sequence
<220> FEATURE:
<223> OTHER INFORMATION: Ab-D HCDR1

<400> SEQUENCE: 38

Asp His Tyr Met Ser
1               5

<210> SEQ ID NO 39
<211> LENGTH: 17
<212> TYPE: PRT
<213> ORGANISM: Artificial Sequence
<220> FEATURE:
<223> OTHER INFORMATION: Ab-D HCDR2

<400> SEQUENCE: 39

Asp Ile Asn Pro Tyr Ser Gly Glu Thr Thr Tyr Asn Gln Lys Phe Lys
1               5                   10                  15

Gly

<210> SEQ ID NO 40
<211> LENGTH: 10
<212> TYPE: PRT
<213> ORGANISM: Artificial Sequence
<220> FEATURE:
<223> OTHER INFORMATION: Ab-D HCDR3

<400> SEQUENCE: 40

Asp Asp Tyr Asp Ala Ser Pro Phe Ala Tyr
1               5                   10

<210> SEQ ID NO 41
<211> LENGTH: 645
<212> TYPE: DNA
<213> ORGANISM: Mus musculus

<400> SEQUENCE: 41
gatgtccaga tgattcagtc tccatcctcc ctgtctgcat ctttgggaga catagtcacc      60
atgacttgcc aggcaagtca gggcactagc attaatttaa actggtttca gcaaaaacca     120
gggaaggctc ctaagctcct gatctatggt tcaagcaact tggaagatgg ggtcccatca     180
```

```
aggttcagtg gcagtagata tgggacagat tcactctca ccatcagcag cctggaggat    240
gaagatctgg caacttattt ctgtctacaa catagttatc tcccgtacac gttcggaggg    300
gggaccaagc tggaaataaa acgggctgat gctgcaccaa ctgtatccat cttcccacca    360
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gttag                    645
```

<210> SEQ ID NO 42
<211> LENGTH: 214
<212> TYPE: PRT
<213> ORGANISM: Mus musculus

<400> SEQUENCE: 42

```
Asp Val Gln Met Ile Gln Ser Pro Ser Ser Leu Ser Ala Ser Leu Gly
1               5                   10                  15

Asp Ile Val Thr Met Thr Cys Gln Ala Ser Gln Gly Thr Ser Ile Asn
            20                  25                  30

Leu Asn Trp Phe Gln Gln Lys Pro Gly Lys Ala Pro Lys Leu Leu Ile
        35                  40                  45

Tyr Gly Ser Ser Asn Leu Glu Asp Gly Val Pro Ser Arg Phe Ser Gly
    50                  55                  60

Ser Arg Tyr Gly Thr Asp Phe Thr Leu Thr Ile Ser Ser Leu Glu Asp
65                  70                  75                  80

Glu Asp Leu Ala Thr Tyr Phe Cys Leu Gln His Ser Tyr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 43
<211> LENGTH: 1332
<212> TYPE: DNA
<213> ORGANISM: Mus musculus

<400> SEQUENCE: 43

```
gaggtccagc tgcaacagtc tggacctgaa ctggtgacgc tggggcttc agtgaagata     60 tcttgtaagg cttctggata cacattcact gaccactaca tgagctgggt gaagcagagt    120
```

```
catgaaaaaa gccttgagtg gattggagat attaatccct attctggtga aactacctac    180
aaccagaagt tcaagggcac ggccacattg actgtagaca agtcttccag tatagcctac    240
atggagatcc gcggcctgac atctgaggac tctgcagtct attactgtgc aagagatgat    300
tacgacgcct ctccgtttgc ttactggggc caagggactc tggtcactgt ctctgcagcc    360
aaaacgacac ccccatctgt ctatccactg gcccctggat ctgctgccca aactaactcc    420
atggtgaccc tgggatgcct ggtcaagggc tatttccctg agccagtgac agtgacctgg    480
aactctggat ccctgtccag cggtgtgcac accttcccag ctgtcctgca gtctgacctc    540
tacactctga gcagctcagt gactgtcccc tccagcacct ggcccagcga gaccgtcacc    600
tgcaacgttg cccacccggc cagcagcacc aaggtggaca agaaaattgt gcccagggat    660
tgtggttgta agccttgcat atgtacagtc ccagaagtat catctgtctt catcttcccc    720
ccaaagccca aggatgtgct caccattact ctgactccta aggtcacgtg tgttgtggta    780
gacatcagca aggatgatcc cgaggtccag ttcagctggt ttgtagatga tgtggaggtg    840
cacacagctc agacgcaacc ccgggaggag cagttcaaca gcactttccg ctcagtcagt    900
gaacttccca tcatgcacca ggactggctc aatggcaagg agttcaaatg cagggtcaac    960
agtccagctt ccctgccccc catcgagaaa accatctcca aaaccaaagg cagaccgaag   1020
gctccacagg tgtacaccat tccacctccc aaggagcaga tggccaagga taaagtcagt   1080
ctgacctgca tgataacaga cttcttccct gaagacatta ctgtggagtg cagtggaat    1140 gggcagccag cggagaacta caagaacact cagcccatca tggacacaga tggctcttac   1200
ttcatctaca gcaagctcaa tgtgcagaag agcaactggg aggcaggaaa tactttcacc   1260
tgctctgtgt tacatgaggg cctgcacaac caccatactg agaagagcct ctcccactct   1320
cctggtaaat ga                                                       1332
```

<210> SEQ ID NO 44
<211> LENGTH: 443
<212> TYPE: PRT
<213> ORGANISM: Mus musculus

<400> SEQUENCE: 44

Glu Val Gln Leu Gln Gln Ser Gly Pro Glu Leu Val Thr Pro Gly Ala
1               5                   10                  15

Ser Val Lys Ile Ser Cys Lys Ala Ser Gly Tyr Thr Phe Thr Asp His
            20                  25                  30

Tyr Met Ser Trp Val Lys Gln Ser His Gly Lys Ser Leu Glu Trp Ile
        35                  40                  45

Gly Asp Ile Asn Pro Tyr Ser Gly Glu Thr Thr Tyr Asn Gln Lys Phe
    50                  55                  60

Lys Gly Thr Ala Thr Leu Thr Val Asp Lys Ser Ser Ile Ala Tyr
65                  70                  75                  80

Met Glu Ile Arg Gly Leu Thr Ser Glu Asp Ser Ala Val Tyr Tyr Cys
                85                  90                  95

Ala Arg Asp Asp Tyr Asp Ala Ser Pro Phe Ala Tyr Trp Gly Gln Gly
            100                 105                 110

Thr Leu Val Thr Val Ser Ala Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
            165                 170                 175

Gln Ser Asp Leu Tyr Thr Leu Ser Ser Val Val Thr Val Pro Ser Ser
        180                 185                 190

Thr Trp Pro Ser Glu Thr Val Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
                260                 265                 270

Trp Phe Val Asp Asp Val Glu Val His Thr Ala Gln Thr Gln Pro Arg
            275                 280                 285

Glu Glu Gln Phe Asn Ser Thr Phe Arg Ser Val Ser Glu Leu Pro Ile
            290                 295                 300

Met His Gln Asp Trp Leu Asn Gly Lys Glu Phe Lys Cys Arg Val Asn
305                 310                 315                 320

Ser Pro Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
        370                 375                 380

Glu Asn Tyr Lys Asn Thr Gln Pro Ile Met Asp Thr Asp Gly Ser Tyr
385                 390                 395                 400

Phe Ile Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 45
<211> LENGTH: 11
<212> TYPE: PRT
<213> ORGANISM: Artificial Sequence
<220> FEATURE:
<223> OTHER INFORMATION: Ab-2 LCDR1

<400> SEQUENCE: 45

Arg Ala Ser Ser Val Tyr Tyr Tyr Met His
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Ab-2 LCDR2

<400> SEQUENCE: 46

Ala Thr Ser Asn Leu Ala Ser

<210> SEQ ID NO 47
<211> LENGTH: 9
<212> TYPE: PRT
<213> ORGANISM: Artificial Sequence
<220> FEATURE:
<223> OTHER INFORMATION: Ab-3 LCDR3

<400> SEQUENCE: 47

Gln Gln Trp Ser Ser Asp Pro Leu Thr
1               5

<210> SEQ ID NO 48
<211> LENGTH: 5
<212> TYPE: PRT
<213> ORGANISM: Artificial Sequence
<220> FEATURE:
<223> OTHER INFORMATION: Ab-2 HCDR1

<400> SEQUENCE: 48

Asp Tyr Phe Ile His
1               5

<210> SEQ ID NO 49
<211> LENGTH: 17
<212> TYPE: PRT
<213> ORGANISM: Artificial Sequence
<220> FEATURE:
<223> OTHER INFORMATION: Ab-2 HCDR2

<400> SEQUENCE: 49

Arg Leu Asp Pro Glu Asp Gly Glu Ser Asp Tyr Ala Pro Lys Phe Gln
1               5                   10                  15

Asp

<210> SEQ ID NO 50
<211> LENGTH: 12
<212> TYPE: PRT
<213> ORGANISM: Artificial Sequence
<220> FEATURE:
<223> OTHER INFORMATION: Ab-2 HCDR3

<400> SEQUENCE: 50

Glu Asp Tyr Asp Gly Thr Tyr Thr Phe Phe Pro Tyr
1               5                   10

<210> SEQ ID NO 51
<211> LENGTH: 642
<212> TYPE: DNA
<213> ORGANISM: Mus musculus
<220> FEATURE:
<221> NAME/KEY: misc_feature
<223> OTHER INFORMATION: Ab-2 light chain (no signal)

<400> SEQUENCE: 51

```
caaattgttc tctcccagtc tccagcaatc ctgtctacat ctccagggga gaaggtcaca      60
atgacttgca gggccagctc aagtgtatat tacatgcact ggtaccagca gaagccagga     120
tcctccccca aaccctggat ttatgccaca tccaacctgg cttctggagt ccctgttcgc     180
ttcagtggca gtgggtctgg gacctcttac tctctcacaa tcaccagagt ggaggctgaa     240
gatgctgcca ttattactg ccagcagtgg agtagtgacc cactcacgtt cggtgctggg      300
accaagctgg agctgaaacg ggctgatgct gcaccaactg tatccatctt cccaccatcc     360
```

```
agtgagcagt taacatctgg aggtgcctca gtcgtgtgct tcttgaacaa cttctacccc      420
aaagacatca atgtcaagtg gaagattgat ggcagtgaac gacaaaatgg cgtcctgaac      480
agttggactg atcaggacag caaagacagc acctacagca tgagcagcac cctcacgttg      540
accaaggacg agtatgaacg acataacagc tatacctgtg aggccactca caagacatca      600
acttcaccca ttgtcaagag cttcaacagg aatgagtgtt ag                        642
```

<210> SEQ ID NO 52
<211> LENGTH: 213
<212> TYPE: PRT
<213> ORGANISM: Mus musculus
<220> FEATURE:
<221> NAME/KEY: MISC_FEATURE
<223> OTHER INFORMATION: Ab-2 light chain (no signal)

<400> SEQUENCE: 52

```
Gln Ile Val Leu Ser Gln Ser Pro Ala Ile Leu Ser Thr Ser Pro Gly
1               5                   10                  15

Glu Lys Val Thr Met Thr Cys Arg Ala Ser Ser Ser Val Tyr Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Thr Arg Val Glu Ala Glu
65                  70                  75                  80

Asp Ala Ala Thr Tyr Tyr Cys Gln Gln Trp Ser Ser Asp Pro Leu Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```

<210> SEQ ID NO 53
<211> LENGTH: 1338
<212> TYPE: DNA
<213> ORGANISM: Mus musculus
<220> FEATURE:
<221> NAME/KEY: misc_feature
<223> OTHER INFORMATION: Ab-2 heavy chain (no signal)

<400> SEQUENCE: 53

```
gaggttcagg tgcagcagtc tggggccagaa cttgtgaagc caggggcctc agtcaagttg      60
tcctgcacag cttctggctt caacattaaa gactacttta cactgggt gaagcagagg        120 cctgaacagg gcctggagtg gattggaagg cttgatcctg aggatggtga aagtgattat      180
```

```
gccccgaagt tccaggacaa ggccattatg acagcagaca catcatccaa cacagcctat      240
cttcagctca gaagcctgac atctgaggac actgccatct attattgtga gagagaggac      300
tacgatggta cctacacctt ttttccttac tggggccaag ggactctggt cactgtctct      360
gcagccaaaa cgacaccccc atctgtctat ccactggccc ctggatctgc tgcccaaact      420
aactccatgg tgaccctggg atgcctggtc aagggctatt tccctgagcc agtgacagtg      480
acctggaact ctggatccct gtccagcggt gtgcacacct tcccagctgt cctgcagtct      540
gacctctaca ctctgagcag ctcagtgact gtcccctcca gcacctggcc cagcgagacc      600
gtcacctgca acgttgccca cccggccagc agcaccaagg tggacaagaa aattgtgccc      660
agggattgtg gttgtaagcc ttgcatatgt acagtcccag aagtatcatc tgtcttcatc      720 ttcccccaa agcccaagga tgtgctcacc attactctga ctcctaaggt cacgtgtgtt      780
gtggtagaca tcagcaagga tgatcccgag gtccagttca gctggtttgt agatgatgtg      840
gaggtgcaca cagctcagac gcaaccccgg gaggagcagt tcaacagcac tttccgctca      900
gtcagtgaac ttcccatcat gcaccaggac tggctcaatg gcaaggagtt caaatgcagg      960
gtcaacagtg cagcttttcc ctgcccccatc gagaaaacca tctccaaaac caaaggcaga     1020
ccgaaggctc cacaggtgta caccattcca cctcccaagg agcagatggc caaggataaa     1080
gtcagtctga cctgcatgat aacagacttc ttccctgaag acattactgt ggagtggcag     1140
tggaatgggc agccagcgga gaactacaag aacactcagc ccatcatgga cacagatggc     1200
tcttacttca tctacagcaa gctcaatgtg cagaagagca actgggaggc aggaaatact     1260
ttcacctgct ctgtgttaca tgagggcctg cacaaccacc atactgagaa gagcctctcc     1320
cactctcctg gtaaatga                                                   1338

<210> SEQ ID NO 54
<211> LENGTH: 445
<212> TYPE: PRT
<213> ORGANISM: Mus musculus
<220> FEATURE:
<221> NAME/KEY: MISC_FEATURE
<223> OTHER INFORMATION: Ab-2 heavy chain (no signal)

<400> SEQUENCE: 54

Glu Val Gln Val Gln Gln Ser Gly Pro Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Phe Ile His Trp Val Lys Gln Arg Pro Glu Gln Gly Leu Glu Trp Ile
        35                  40                  45

Gly Arg Leu Asp Pro Glu Asp Gly Glu Ser Asp Tyr Ala Pro Lys Phe
    50                  55                  60

Gln Asp Lys Ala Ile Met Thr Ala Asp Thr Ser Ser Asn Thr Ala Tyr
65                  70                  75                  80

Leu Gln Leu Arg Ser Leu Thr Ser Glu Asp Thr Ala Ile Tyr Tyr Cys
                85                  90                  95

Glu Arg Glu Asp Tyr Asp Gly Thr Tyr Thr Phe Phe Pro Tyr Trp Gly
            100                 105                 110

Gln Gly Thr Leu Val Thr Val Ser Ala Ala Lys Thr Thr Pro Pro Ser
        115                 120                 125

Val Tyr Pro Leu Ala Pro Gly Ser Ala Ala Gln Thr Asn Ser Met Val
    130                 135                 140
```

```
Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
            165                 170                 175

Val Leu Gln Ser Asp Leu Tyr Thr Leu Ser Ser Val Thr Val Pro
        180                 185                 190

Ser Ser Thr Trp Pro Ser Glu Thr Val Thr Cys Asn Val Ala His Pro
            195                 200                 205

Ala Ser Ser Thr Lys Val Asp Lys Lys Ile Val Pro Arg Asp Cys Gly
        210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
            245                 250                 255

Val Thr Cys Val Val Val Asp Ile Ser Lys Asp Asp Pro Glu Val Gln
        260                 265                 270

Phe Ser Trp Phe Val Asp Asp Val Glu Val His Thr Ala Gln Thr Gln
            275                 280                 285

Pro Arg Glu Glu Gln Phe Asn Ser Thr Phe Arg Ser Val Ser Glu Leu
290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
            355                 360                 365

Asp Phe Phe Pro Glu Asp Ile Thr Val Glu Trp Gln Trp Asn Gly Gln
370                 375                 380

Pro Ala Glu Asn Tyr Lys Asn Thr Gln Pro Ile Met Asp Thr Asp Gly
385                 390                 395                 400

Ser Tyr Phe Ile Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
            435                 440                 445

<210> SEQ ID NO 55
<211> LENGTH: 12
<212> TYPE: PRT
<213> ORGANISM: Artificial Sequence
<220> FEATURE:
<223> OTHER INFORMATION: Ab-3 and Ab-15 LCDR1

<400> SEQUENCE: 55

Ser Val Ser Ser Thr Ile Ser Ser Asn His Leu His
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Ab-3 and Ab-15 LCDR2

<400> SEQUENCE: 56
```

Gly Thr Ser Asn Leu Ala Ser
1               5

<210> SEQ ID NO 57
<211> LENGTH: 9
<212> TYPE: PRT
<213> ORGANISM: Artificial Sequence
<220> FEATURE:
<223> OTHER INFORMATION: Ab-3 and Ab-15 LCDR3

<400> SEQUENCE: 57

Gln Gln Trp Ser Ser Tyr Pro Leu Thr
1               5

<210> SEQ ID NO 58
<211> LENGTH: 5
<212> TYPE: PRT
<213> ORGANISM: Artificial Sequence
<220> FEATURE:
<223> OTHER INFORMATION: Ab-3 and Ab-15 HCDR1

<400> SEQUENCE: 58

Asp Phe Tyr Leu His
1               5

<210> SEQ ID NO 59
<211> LENGTH: 17
<212> TYPE: PRT
<213> ORGANISM: Artificial Sequence
<220> FEATURE:
<223> OTHER INFORMATION: Ab-3 and Ab-15 HCDR2

<400> SEQUENCE: 59

Arg Ile Asp Pro Glu Asn Gly Asp Thr Leu Tyr Asp Pro Lys Phe Gln
1               5                   10                  15

Asp

<210> SEQ ID NO 60
<211> LENGTH: 16
<212> TYPE: PRT
<213> ORGANISM: Artificial Sequence
<220> FEATURE:
<223> OTHER INFORMATION: Ab-3 and Ab-15 HCDR3

<400> SEQUENCE: 60

Glu Ala Asp Tyr Phe His Asp Gly Thr Ser Tyr Trp Tyr Phe Asp Val
1               5                   10                  15

<210> SEQ ID NO 61
<211> LENGTH: 648
<212> TYPE: DNA
<213> ORGANISM: Mus musculus
<220> FEATURE:
<221> NAME/KEY: misc_feature
<223> OTHER INFORMATION: Ab-3 light chain

<400> SEQUENCE: 61
gaaattgtgc tcacccagtc tccagcactc atggctgcat ctccggggga gaaggtcacc      60
atcacctgca gtgtcagttc aactataagt tccaaccact tgcactggtt ccagcagaag     120
tcagacacct cccccaaacc ctggatttat ggcacatcca acctggcttc tggagtccct     180
gttcgcttca gtggcagtgg atctgggacc tcttattctc tcacaatcag cagcatggag     240
gctgaggatg ctgccactta ttactgtcaa cagtggagta gttaccccact cacgttcggc    300

-continued

```
gctgggacca agctggagct gagacgggct gatgctgcac caactgtatc catcttccca    360
ccatccagtg agcagttaac atctggaggt gcctcagtcg tgtgcttctt gaacaacttc    420
taccccaaag acatcaatgt caagtggaag attgatggca gtgaacgaca aaatggcgtc    480
ctgaacagtt ggactgatca ggacagcaaa gacagcacct acagcatgag cagcaccctc    540
acgttgacca aggacgagta tgaacgacat aacagctata cctgtgaggc cactcacaag    600
acatcaactt cacccattgt caagagcttc aacaggaatg agtgttag                 648
```

<210> SEQ ID NO 62
<211> LENGTH: 215
<212> TYPE: PRT
<213> ORGANISM: Mus musculus
<220> FEATURE:
<221> NAME/KEY: MISC_FEATURE
<223> OTHER INFORMATION: Ab-3 light chain (no signal)

<400> SEQUENCE: 62

```
Glu Ile Val Leu Thr Gln Ser Pro Ala Leu Met Ala Ala Ser Pro Gly
1               5                   10                  15

Glu Lys Val Thr Ile Thr Cys Ser Val Ser Ser Thr Ile Ser Ser Asn
            20                  25                  30

His Leu His Trp Phe Gln Gln Lys Ser Asp Thr Ser Pro Lys Pro Trp
        35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Leu Thr Phe Gly Ala Gly Thr Lys Leu Glu Leu Arg Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215
```

<210> SEQ ID NO 63
<211> LENGTH: 1350
<212> TYPE: DNA
<213> ORGANISM: Mus musculus
<220> FEATURE:
<221> NAME/KEY: misc_feature
<223> OTHER INFORMATION: Ab-3 heavy chain

<400> SEQUENCE: 63

```
gaggttcagc tgcagcagtc tggggctgaa cttgtgaggc caggggcctt agtcaagttg    60
tcctgcacag cttctgactt caacattaaa gacttctatc tacactggat gaggcagcgg   120
```

```
cctgaacagg gcctggactg gattggaagg attgatcctg agaatggtga tactttatat    180
gacccgaagt tccaggacaa ggccactctt acaacagaca catcctccaa cacagcctac    240
ctgcagctca gcggcctgac atctgagacc actgccgtct attactgttc tagagaggcg    300
gattatttcc acgatggtac ctcctactgg tacttcgatg tctggggcgc agggaccaca    360
atcaccgtct cctcagccaa aacgacaccc ccatctgtct atccactggc ccctggatct    420
gctgcccaaa ctaactccat ggtgaccctg ggatgcctgg tcaagggcta tttccctgag    480
ccagtgacag tgacctggaa ctctggatcc ctgtccagcg gtgtgcacac cttcccagct    540
gtcctgcagt ctgacctcta cactctgagc agctcagtga ctgtcccctc agcacctgg    600 cccagcgaga ccgtcacctg caacgttgcc cacccggcca gcagcaccaa ggtggacaag    660
aaaattgtgc cagggattg tggttgtaag ccttgcatat gtacagtccc agaagtatca    720
tctgtcttca tcttcccccc aaagcccaag gatgtgctca ccattactct gactcctaag    780
gtcacgtgtg ttgtggtaga catcagcaag gatgatcccg aggtccagtt cagctggttt    840
gtagatgatg tggaggtgca cacagctcag acgcaaccccc gggaggagca gttcaacagc    900
actttccgct cagtcagtga acttcccatc atgcaccagg actggctcaa tggcaaggag    960
ttcaaatgca gggtcaacag tgcagctttc cctgcccca tcgagaaaac catctccaaa   1020
accaaaggca gaccgaaggc tccacaggtg tacaccattc cacctcccaa ggagcagatg   1080
gccaaggata aagtcagtct gacctgcatg ataacagact tcttccctga agacattact   1140
gtggagtggc agtggaatgg gcagccagcg agaactaca agaacactca gcccatcatg   1200
gacacagatg gctcttactt catctacagc aagctcaatg tgcagaagag caactgggag   1260
gcaggaaata ctttcacctg ctctgtgtta catgagggcc tgcacaacca ccatactgag   1320
aagagcctct cccactctcc tggtaaatga                                     1350
```

<210> SEQ ID NO 64
<211> LENGTH: 449
<212> TYPE: PRT
<213> ORGANISM: Mus musculus
<220> FEATURE:
<221> NAME/KEY: MISC_FEATURE
<223> OTHER INFORMATION: Ab-3 heavy chain (no signal)

<400> SEQUENCE: 64

Glu Val Gln Leu Gln Gln Ser Gly Ala Glu Leu Val Arg Pro Gly Ala
1               5                   10                  15

Leu Val Lys Leu Ser Cys Thr Ala Ser Asp Phe Asn Ile Lys Asp Phe
            20                  25                  30

Tyr Leu His Trp Met Arg Gln Arg Pro Glu Gln Gly Leu Asp Trp Ile
        35                  40                  45

Gly Arg Ile Asp Pro Glu Asn Gly Asp Thr Leu Tyr Asp Pro Lys Phe
    50                  55                  60

Gln Asp Lys Ala Thr Leu Thr Thr Asp Thr Ser Ser Asn Thr Ala Tyr
65                  70                  75                  80

Leu Gln Leu Ser Gly Leu Thr Ser Glu Thr Thr Ala Val Tyr Tyr Cys
                85                  90                  95

Ser Arg Glu Ala Asp Tyr Phe His Asp Gly Thr Ser Tyr Trp Tyr Phe
            100                 105                 110

Asp Val Trp Gly Ala Gly Thr Thr Ile Thr Val Ser Ser Ala Lys Thr
        115                 120                 125

Thr Pro Pro Ser Val Tyr Pro Leu Ala Pro Gly Ser Ala Ala Gln Thr

```
                130                 135                 140
Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
                180                 185                 190

Val Thr Val Pro Ser Ser Thr Trp Pro Ser Glu Thr Val Thr Cys Asn
                195                 200                 205

Val Ala His Pro Ala Ser Ser Thr Lys Val Asp Lys Lys Ile Val Pro
                210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
                260                 265                 270

Pro Glu Val Gln Phe Ser Trp Phe Val Asp Asp Val Glu Val His Thr
                275                 280                 285

Ala Gln Thr Gln Pro Arg Glu Glu Gln Phe Asn Ser Thr Phe Arg Ser
                290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
                340                 345                 350

Ile Pro Pro Pro Lys Glu Gln Met Ala Lys Asp Lys Val Ser Leu Thr
                355                 360                 365

Cys Met Ile Thr Asp Phe Phe Pro Glu Asp Ile Thr Val Glu Trp Gln
                370                 375                 380

Trp Asn Gly Gln Pro Ala Glu Asn Tyr Lys Asn Thr Gln Pro Ile Met
385                 390                 395                 400

Asp Thr Asp Gly Ser Tyr Phe Ile Tyr Ser Lys Leu Asn Val Gln Lys
                405                 410                 415

Ser Asn Trp Glu Ala Gly Asn Thr Phe Thr Cys Ser Val Leu His Glu
                420                 425                 430

Gly Leu His Asn His His Thr Glu Lys Ser Leu Ser His Ser Pro Gly
                435                 440                 445

Lys

<210> SEQ ID NO 65
<211> LENGTH: 324
<212> TYPE: DNA
<213> ORGANISM: Mus musculus
<220> FEATURE:
<221> NAME/KEY: misc_feature
<223> OTHER INFORMATION: Ab-15 light variable

<400> SEQUENCE: 65
gacatccaga tgacccagtc tccatcctcc ctctcagcat ccgtaggcga tagagttaca      60
ataacatgca gcgtatcatc aactatatca tcaaatcatc ttcattggtt ccaacagaaa     120
cccggcaaag cacctaaatc acttatatac ggcacatcaa atctcgcatc aggcgttcct     180
tcaagatttt caggctctgg ctcaggcacc gactttactc ttacaatatc ctccctccaa     240
```

```
cccgaagact tcgcaaccta ttactgtcaa caatggtcct catatccact cacatttggc    300
ggcggcacaa aagtagaaat taaa                                           324
```

<210> SEQ ID NO 66
<211> LENGTH: 108
<212> TYPE: PRT
<213> ORGANISM: Mus musculus
<220> FEATURE:
<221> NAME/KEY: MISC_FEATURE
<223> OTHER INFORMATION: Ab-15 light variable

<400> SEQUENCE: 66

```
Asp Ile Gln Met Thr Gln Ser Pro Ser Ser Leu Ser Ala Ser Val Gly
1               5                   10                  15

Asp Arg Val Thr Ile Thr Cys Ser Val Ser Ser Thr Ile Ser Ser Asn
                20                  25                  30

His Leu His Trp Phe Gln Gln Lys Pro Gly Lys Ala Pro Lys Ser Leu
            35                  40                  45

Ile Tyr Gly Thr Ser Asn Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Trp Ser Ser Tyr Pro
                85                  90                  95

Leu Thr Phe Gly Gly Gly Thr Lys Val Glu Ile Lys
            100                 105
```

<210> SEQ ID NO 67
<211> LENGTH: 375
<212> TYPE: DNA
<213> ORGANISM: Mus musculus
<220> FEATURE:
<221> NAME/KEY: misc_feature
<223> OTHER INFORMATION: Ab-15 heavy variable

<400> SEQUENCE: 67

```
gaggtgcagc tggtgcagtc tggggctgag gtgaagaagc ctggggcctc agtgaaggtc    60
tcctgcaagg cttctgactt caacattaaa gacttctatc tacactgggt gcgacaggcc   120
cctggacaag gcttgagtg gattggaagg attgatcctg agaatggtga tactttatat     180
gacccgaagt tccaggacaa ggtcaccatg accacagaca cgtccaccag cacagcctac   240
atggagctga ggagcctgag atctgacgac acggccgtgt attactgtgc gagagaggcg   300
gattatttcc acgatggtac ctcctactgg tacttcgatg tctggggccg tggcaccctg   360
gtcaccgtct ctagt                                                    375
```

<210> SEQ ID NO 68
<211> LENGTH: 125
<212> TYPE: PRT
<213> ORGANISM: Mus musculus
<220> FEATURE:
<221> NAME/KEY: MISC_FEATURE
<223> OTHER INFORMATION: Ab-15 heavy variable

<400> SEQUENCE: 68

```
Glu Val Gln Leu Val Gln Ser Gly Ala Glu Val Lys Lys Pro Gly Ala
1               5                   10                  15

Ser Val Lys Val Ser Cys Lys Ala Ser Asp Phe Asn Ile Lys Asp Phe
                20                  25                  30
```

Tyr Leu His Trp Val Arg Gln Ala Pro Gly Gln Gly Leu Glu Trp Ile
        35                  40                  45

Gly Arg Ile Asp Pro Glu Asn Gly Asp Thr Leu Tyr Asp Pro Lys Phe
 50                  55                  60

Gln Asp Lys Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Glu Ala Asp Tyr Phe His Asp Gly Thr Ser Tyr Trp Tyr Phe
            100                 105                 110

Asp Val Trp Gly Arg Gly Thr Leu Val Thr Val Ser Ser
        115                 120                 125

<210> SEQ ID NO 69
<211> LENGTH: 645
<212> TYPE: DNA
<213> ORGANISM: Artificial Sequence
<220> FEATURE:
<223> OTHER INFORMATION: Humanized antibody
<220> FEATURE:
<221> NAME/KEY: misc_feature
<223> OTHER INFORMATION: Ab-15 light chain

<400> SEQUENCE: 69
gacatccaga tgacccagtc tccatcctcc ctctcagcat ccgtaggcga tagagttaca      60
ataacatgca gcgtatcatc aactatatca tcaaatcatc ttcattggtt ccaacagaaa     120
cccggcaaag cacctaaatc acttatatac ggcacatcaa atctcgcatc aggcgttcct     180
tcaagatttt caggctctgg ctcaggcacc gactttactc ttacaatatc ctccctccaa     240
cccgaagact tcgcaaccta ttactgtcaa caatggtcct catatccact cacatttggc     300
ggcggcacaa agtagaaat aaacgtacg gtggctgcac catctgtctt catcttcccg       360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactca cgagaaacac aaagtctacg cctgcgaagt cacccatcag     600
ggcctgagct cgcccgtcac aaagagcttc aacaggggag agtgt                    645

<210> SEQ ID NO 70
<211> LENGTH: 215
<212> TYPE: PRT
<213> ORGANISM: Artificial Sequence
<220> FEATURE:
<223> OTHER INFORMATION: Humanized antibody sequence
<220> FEATURE:
<221> NAME/KEY: MISC_FEATURE
<223> OTHER INFORMATION: Ab-15 light chain

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Ser Val Ser Thr Ile Ser Ser Asn
            20                  25                  30

His Leu His Trp Phe Gln Gln Lys Pro Gly Lys Ala Pro Lys Ser Leu
        35                  40                  45

Ile Tyr Gly Thr Ser Asn Leu Ala Ser Gly Val Pro Ser Arg Phe Ser
 50                  55                  60

Gly Ser Gly Ser Gly Thr Asp Phe Thr Leu Thr Ile Ser Ser Leu Gln

```
                65                  70                  75                  80
Pro Glu Asp Phe Ala Thr Tyr Tyr Cys Gln Gln Trp Ser Ser Tyr Pro
                    85                  90                  95

Leu Thr Phe Gly Gly Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 71
<211> LENGTH: 1353
<212> TYPE: DNA
<213> ORGANISM: Artificial Sequence
<220> FEATURE:
<223> OTHER INFORMATION: Humanized antibody
<220> FEATURE:
<221> NAME/KEY: misc_feature
<223> OTHER INFORMATION: Ab-15 heavy chain

<400> SEQUENCE: 71
gaggtgcagc tggtgcagtc tggggctgag gtgaagaagc ctggggcctc agtgaaggtc      60
tcctgcaagg cttctgactt caacattaaa gacttctatc tacactgggt gcgacaggcc     120
cctggacaag gcttgagtg gattggaagg attgatcctg agaatggtga tactttatat     180
gacccgaagt ccaggacaa ggtcaccatg accacagaca cgtccaccag cacagcctac     240
atggagctga ggagcctgag atctgacgac acggccgtgt attactgtgc gagagaggcg     300
gattatttcc acgatggtac ctcctactgg tacttcgatg tctggggccg tggcaccctg     360
gtcaccgtct ctagtgcctc caccaagggc ccatcggtct tccccctggc gccctgctcc     420
aggagcacct ccgagagcac agcggccctg ggctgcctgg tcaaggacta cttccccgaa     480
ccggtgacgg tgtcgtggaa ctcaggcgct ctgaccagcg gcgtgcacac cttcccagct     540
gtcctacagt cctcaggact ctactccctc agcagcgtgg tgaccgtgcc ctccagcaac     600
ttcggcaccc agacctacac ctgcaacgta gatcacaagc ccagcaacac caaggtggac     660
aagacagttg agcgcaaatg ttgtgtcgag tgcccaccgt gcccagcacc acctgtggca     720
ggaccgtcag tcttcctctt ccccccaaaa cccaaggaca cctcatgat ctcccggacc     780
cctgaggtca cgtgcgtggt ggtggacgtg agccacgaag accccgaggt ccagttcaac     840
tggtacgtgg acggcgtgga ggtgcataat gccaagacaa agccacggga ggagcagttc     900
aacagcacgt tccgtgtggt cagcgtcctc accgttgtgc accaggactg gctgaacggc     960
aaggagtaca agtgcaaggt ctccaacaaa ggcctcccag cccccatcga gaaaaccatc    1020
tccaaaacca aagggcagcc ccgagaacca caggtgtaca ccctgccccc atcccgggag    1080
gagatgacca agaaccaggt cagcctgacc tgcctggtca aaggcttcta ccccagcgac    1140
```

```
atcgccgtgg agtgggagag caatgggcag ccggagaaca actacaagac cacacctccc    1200
atgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctcccct gtctccgggt aaa                                1353
```

```
<210> SEQ ID NO 72
<211> LENGTH: 451
<212> TYPE: PRT
<213> ORGANISM: Artificial Sequence
<220> FEATURE:
<223> OTHER INFORMATION: Humanized antibody sequence
<220> FEATURE:
<221> NAME/KEY: MISC_FEATURE
<223> OTHER INFORMATION: Ab-15 heavy chain

<400> SEQUENCE: 72

Glu Val Gln Leu Val Gln Ser Gly Ala Glu Val Lys Lys Pro Gly Ala
1               5                   10                  15

Ser Val Lys Val Ser Cys Lys Ala Ser Asp Phe Asn Ile Lys Asp Phe
            20                  25                  30

Tyr Leu His Trp Val Arg Gln Ala Pro Gly Gln Gly Leu Glu Trp Ile
        35                  40                  45

Gly Arg Ile Asp Pro Glu Asn Gly Asp Thr Leu Tyr Asp Pro Lys Phe
    50                  55                  60

Gln Asp Lys Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Asp Tyr Phe His Asp Gly Thr Ser Tyr Trp Tyr Phe
            100                 105                 110

Asp Val Trp Gly Arg Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300
```

```
Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 73
<211> LENGTH: 11
<212> TYPE: PRT
<213> ORGANISM: Artificial Sequence
<220> FEATURE:
<223> OTHER INFORMATION: Ab-4 and Ab-5 LCDR1

<400> SEQUENCE: 73

Arg Ala Ser Gln Asp Ile Ser Asn Tyr Leu Asn
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Ab-4 and Ab-5 LCDR2

<400> SEQUENCE: 74

Tyr Thr Ser Arg Leu Leu Ser
1               5

<210> SEQ ID NO 75
<211> LENGTH: 9
<212> TYPE: PRT
<213> ORGANISM: Artificial Sequence
<220> FEATURE:
<223> OTHER INFORMATION: Ab-4 and Ab-5 LCDR3

<400> SEQUENCE: 75

Gln Gln Gly Asp Thr Leu Pro Tyr Thr
1               5

<210> SEQ ID NO 76
<211> LENGTH: 5
<212> TYPE: PRT
<213> ORGANISM: Artificial Sequence
<220> FEATURE:
<223> OTHER INFORMATION: Ab-4 and Ab-5 HCDR1

<400> SEQUENCE: 76
```

Asp Tyr Asn Met His
1               5

<210> SEQ ID NO 77
<211> LENGTH: 17
<212> TYPE: PRT
<213> ORGANISM: Artificial Sequence
<220> FEATURE:
<223> OTHER INFORMATION: Ab-4 and Ab-5 HCDR2

<400> SEQUENCE: 77

Glu Ile Asn Pro Asn Ser Gly Gly Ala Gly Tyr Asn Gln Lys Phe Lys
1               5                   10                  15

Gly

<210> SEQ ID NO 78
<211> LENGTH: 14
<212> TYPE: PRT
<213> ORGANISM: Artificial Sequence
<220> FEATURE:
<223> OTHER INFORMATION: HCDR3

<400> SEQUENCE: 78

Leu Gly Tyr Asp Asp Ile Tyr Asp Asp Trp Tyr Phe Asp Val
1               5                   10

<210> SEQ ID NO 79
<211> LENGTH: 645
<212> TYPE: DNA
<213> ORGANISM: Mus musculus
<220> FEATURE:
<221> NAME/KEY: misc_feature
<223> OTHER INFORMATION: Ab-4 light chain

<400> SEQUENCE: 79
gatatccaga tgacacagat tacatcctcc ctgtctgcct ctctgggaga cagggtctcc      60
atcagttgca gggcaagtca agacattagc aattatttaa actggtatca gcagaaacca     120
gatggaactt ttaaactcct tatcttctac acatcaagat tactctcagg agtcccatca     180
aggttcagtg gcagtgggtc tggaacagat tattctctca ccatttacaa cctggagcaa     240
gaagattttg ccacttactt ttgccaacag ggagatacgc ttccgtacac tttcggaggg     300
gggaccaagc tggaaataaa acgggctgat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag caccctcacg     540
ttgaccaagg acgagtatga acgacataac agctatacct gtgaggccac tcacaagaca     600
tcaacttcac ccattgtcaa gagcttcaac aggaatgagt gttag                     645

<210> SEQ ID NO 80
<211> LENGTH: 214
<212> TYPE: PRT
<213> ORGANISM: Mus musculus
<220> FEATURE:
<221> NAME/KEY: MISC_FEATURE
<223> OTHER INFORMATION: Ab-4 light chain

<400> SEQUENCE: 80

Asp Ile Gln Met Thr Gln Ile Thr Ser Ser Leu Ser Ala Ser Leu Gly
1               5                   10                  15

Asp Arg Val Ser Ile Ser Cys Arg Ala Ser Gln Asp Ile Ser Asn Tyr

```
            20                  25                  30
Leu Asn Trp Tyr Gln Gln Lys Pro Asp Gly Thr Phe Lys Leu Leu Ile
        35                  40                  45

Phe Tyr Thr Ser Arg Leu Leu Ser Gly Val Pro Ser Arg Phe Ser Gly
    50                  55                  60

Ser Gly Ser Gly Thr Asp Tyr Ser Leu Thr Ile Tyr Asn Leu Glu Gln
65                  70                  75                  80

Glu Asp Phe Ala Thr Tyr Phe Cys Gln Gln Gly Asp Thr Leu Pro Tyr
                85                  90                  95

Thr Phe Gly Gly Gly Thr Lys Leu Glu Ile Lys Arg Ala Asp Ala Ala
                100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 81
<211> LENGTH: 1344
<212> TYPE: DNA
<213> ORGANISM: Mus musculus
<220> FEATURE:
<221> NAME/KEY: misc_feature
<223> OTHER INFORMATION: Ab-4 heavy chain

<400> SEQUENCE: 81
gaggtccaac tgcaacagtc tggacctgaa ctaatgaagc tggggcttca gtgaagatg         60 tcctgcaagg cttctggata cattcact  gactacaaca tgcactgggt gaagcagaac        120
caaggaaaga cctagagtg  dataggagaa attaatccta cagtggtgg  tgctggctac        180 aaccagaagt tcaagggcaa ggccacattg actgtagaca gtcctccac  cacagcctac        240 atggagctcc gcagcctgac atctgaggac tctgcagtct attactgtgc aagattgggc        300
tacgatgata tctacgacga ctggtacttc gatgtctggg gcgcaggga  cacggtcacc        360 gtctcctcag ccaaaacgac accccatct  gtctatccac tggcccctgg atctgctgcc        420
caaactaact ccatggtgac cctgggatgc ctggtcaagg gctatttccc tgagccagtg        480
acagtgacct ggaactctgg atccctgtcc agcggtgtgc acaccttccc agctgtcctg        540
cagtctgacc tctacactct gagcagctca gtgactgtcc cctccagcac ctggcccagc        600
gagaccgtca cctgcaacgt tgcccacccg gccagcagca ccaaggtgga caagaaaatt        660
gtgcccaggg attgtggttg taagccttgc atatgtacag tcccagaagt atcatctgtc        720
ttcatcttcc ccccaaagcc caaggatgtg ctcaccatta ctctgactcc taaggtcacg        780
tgtgttgtgg tagacatcag caaggatgat cccgaggtcc agttcagctg gtttgtagat        840
gatgtggagg tgcacacagc tcagacgcaa ccccggggagg agcagttcaa cagcactttc        900
```

-continued

```
cgctcagtca gtgaacttcc catcatgcac caggactggc tcaatggcaa ggagttcaaa      960
tgcagggtca acagtgcagc tttccctgcc cccatcgaga aaaccatctc caaaaccaaa     1020
ggcagaccga aggctccaca ggtgtacacc attccacctc ccaaggagca gatggccaag     1080
gataaagtca gtctgacctg catgataaca gacttcttcc ctgaagacat tactgtggag     1140
tggcagtgga atgggcagcc agcggagaac tacaagaaca ctcagcccat catggacaca     1200
gatggctctt acttcatcta cagcaagctc aatgtgcaga gagcaactg ggaggcagga      1260 aatactttca cctgctctgt gttacatgag ggcctgcaca accaccatac tgagaagagc     1320
ctctcccact ctcctggtaa atga                                            1344
```

<210> SEQ ID NO 82
<211> LENGTH: 447
<212> TYPE: PRT
<213> ORGANISM: Mus musculus
<220> FEATURE:
<221> NAME/KEY: MISC_FEATURE
<223> OTHER INFORMATION: Ab-4 heavy chain

<400> SEQUENCE: 82

```
Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Asn Gln Gly Lys Thr Leu Glu Trp Ile
        35                  40                  45

Gly Glu Ile Asn Pro Asn Ser Gly Gly Ala Gly Tyr Asn Gln Lys Phe
    50                  55                  60

Lys Gly Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Leu Gly Tyr Asp Asp Ile Tyr Asp Asp Trp Tyr Phe Asp Val
            100                 105                 110

Trp Gly Ala Gly Thr Thr Val Thr Val Ser Ser Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
    210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
```

```
                275                 280                 285
Thr Gln Pro Arg Glu Glu Gln Phe Asn Ser Thr Phe Arg Ser Val Ser
        290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
        435                 440                 445

<210> SEQ ID NO 83
<211> LENGTH: 321
<212> TYPE: DNA
<213> ORGANISM: Mus musculus
<220> FEATURE:
<221> NAME/KEY: misc_feature
<223> OTHER INFORMATION: Ab-5 light variable

<400> SEQUENCE: 83
gacatccaga tgacccagtc tccatcctcc ctctccgcat ccgtaggcga ccgcgtaacc      60
ataacatgta gagcatctca agatatttcc aactatttga attggtacca acaaaaaccc     120
ggcaaagcac ctaaactcct catttactat acatcaagac tcctctccgg cgttccatca     180
cgattctcag gctccggctc cggcacagat ttcacactca ctatttcctc cctccaacca     240
gaagattttg caacctatta ctgtcaacaa ggcgatacac tcccatacac attcggcggc     300
ggcacaaaag ttgaaattaa a                                               321

<210> SEQ ID NO 84
<211> LENGTH: 107
<212> TYPE: PRT
<213> ORGANISM: Mus musculus
<220> FEATURE:
<221> NAME/KEY: MISC_FEATURE
<223> OTHER INFORMATION: Ab-5 light variable

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80
            Glu Asp Phe Ala Thr Tyr Tyr Cys Gln Gln Gly Asp Thr Leu Pro Tyr
                                85                  90                  95

Thr Phe Gly Gly Gly Thr Lys Val Glu Ile Lys
                        100                 105
```

<210> SEQ ID NO 85
<211> LENGTH: 369
<212> TYPE: DNA
<213> ORGANISM: Mus musculus
<220> FEATURE:
<221> NAME/KEY: misc_feature
<223> OTHER INFORMATION: Ab-5 heavy variable

<400> SEQUENCE: 85

```
gaggtgcagc tggtgcagag cggcgccgag gtaaaaaaac caggagcaag cgttaaagtt    60
tcttgtaaag caagcggata cacatttaca gattacaaca tgcattgggt aagacaagcg   120
ccaggacaag gattgaatg gatgggcgaa attaacccta atagtggagg agcaggctac    180
aatcaaaaat tcaaaggag agttacaatg acaacagaca caagcacttc aacagcatat    240
atggaactgc gatcacttag aagcgacgat acagctgtat actattgcgc acgacttggg   300
tatgatgata tatgatga ctggtattc gatgtttggg gccagggaac aacagttacc     360
gtctctagt                                                            369
```

<210> SEQ ID NO 86
<211> LENGTH: 123
<212> TYPE: PRT
<213> ORGANISM: Mus musculus
<220> FEATURE:
<221> NAME/KEY: MISC_FEATURE
<223> OTHER INFORMATION: Ab-5 heavy variable

<400> SEQUENCE: 86

```
            Glu Val Gln Leu Val Gln Ser Gly Ala Glu Val Lys Lys Pro Gly Ala
            1               5                   10                  15

Ser Val Lys Val Ser Cys Lys Ala Ser Gly Tyr Thr Phe Thr Asp Tyr
                        20                  25                  30

Asn Met His Trp Val Arg Gln Ala Pro Gly Gln Gly Leu Glu Trp Met
                        35                  40                  45

Gly Glu Ile Asn Pro Asn Ser Gly Gly Ala Gly Tyr Asn Gln Lys Phe
                    50                  55                  60

Lys Gly Arg Val Thr Met Thr Thr Asp Thr Ser Thr Ser Thr Ala Tyr
            65                  70                  75                  80

Met Glu Leu Arg Ser Leu Arg Ser Asp Asp Thr Ala Val Tyr Tyr Cys
                                85                  90                  95

Ala Arg Leu Gly Tyr Asp Asp Ile Tyr Asp Asp Trp Tyr Phe Asp Val
                        100                 105                 110

Trp Gly Gln Gly Thr Thr Val Thr Val Ser Ser
                        115                 120
```

<210> SEQ ID NO 87
<211> LENGTH: 642
<212> TYPE: DNA
<213> ORGANISM: Artificial Sequence
<220> FEATURE:
<223> OTHER INFORMATION: Humanized antibody
<220> FEATURE:
<221> NAME/KEY: misc_feature
<223> OTHER INFORMATION: Ab-5 light chain -continued

```
<400> SEQUENCE: 87
gacatccaga tgacccagtc tccatcctcc ctctccgcat ccgtaggcga ccgcgtaacc    60
ataacatgta gagcatctca agatatttcc aactatttga attggtacca acaaaaaccc   120
ggcaaagcac ctaaactcct catttactat acatcaagac tcctctccgg cgttccatca   180
cgattctcag gctccggctc cggcacagat ttcacactca ctatttcctc cctccaacca   240
gaagattttg caacctatta ctgtcaacaa ggcgatacac tcccatacac attcggcggc   300
ggcacaaaag ttgaaattaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642

<210> SEQ ID NO 88
<211> LENGTH: 214
<212> TYPE: PRT
<213> ORGANISM: Artificial Sequence
<220> FEATURE:
<223> OTHER INFORMATION: Humanized antibody
<220> FEATURE:
<221> NAME/KEY: MISC_FEATURE
<223> OTHER INFORMATION: Ab-5 light chain

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Thr Leu Pro Tyr
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 89
<211> LENGTH: 1347
<212> TYPE: DNA
<213> ORGANISM: Artificial Sequence
<220> FEATURE:
<223> OTHER INFORMATION: Humanized antibody
<220> FEATURE:
<221> NAME/KEY: misc_feature
<223> OTHER INFORMATION: Ab-5 heavy chain

<400> SEQUENCE: 89

```
gaggtgcagc tggtgcagag cggcgccgag gtaaaaaaac caggagcaag cgttaaagtt     60
tcttgtaaag caagcggata tacatttaca gattacaaca tgcattgggt aagacaagcg    120
ccaggacaag gattggaatg gatgggcgaa attaacccta atagtggagg agcaggctac    180
aatcaaaaat tcaaagggag agttacaatg acaacagaca caagcacttc aacagcatat    240
atggaactgc gatcacttag aagcgacgat acagctgtat actattgcgc acgacttggg    300
tatgatgata tatatgatga ctggtatttc gatgtttggg gccagggaac aacagttacc    360
gtctctagtg cctccaccaa gggcccatcg gtcttccccc tggcgccctg ctccaggagc    420
acctccgaga gcacagcggc cctgggctgc ctggtcaagg actacttccc cgaaccggtg    480
acggtgtcgt ggaactcagg cgctctgacc agcggcgtgc acaccttccc agctgtccta    540
cagtcctcag gactctactc cctcagcagc gtggtgaccg tgccctccag caacttcggc    600
acccagacct acacctgcaa cgtagatcac aagcccagca caccaaggt ggacaagaca    660
gttgagcgca aatgttgtgt cgagtgccca ccgtgcccag caccacctgt ggcaggaccg    720
tcagtcttcc tcttcccccc aaaacccaag gacaccctca tgatctcccg gacccctgag    780
gtcacgtgcg tggtggtgga cgtgagccac gaagacccCg aggtccagtt caactggtac    840
gtggacggcg tggaggtgca taatgccaag acaaagccac gggaggagca gttcaacagc    900
acgttccgtg tggtcagcgt cctcaccgtt gtgcaccagg actggctgaa cggcaaggag    960
tacaagtgca aggtctccaa caaaggcctc ccagccccca tcgagaaaac catctccaaa   1020
accaaagggc agccccgaga accacaggtg tacaccctgc ccccatcccg ggaggagatg   1080
accaagaacc aggtcagcct gacctgcctg gtcaaaggct tctacccag cgacatcgcc   1140
gtggagtggg agagcaatgg gcagccggag aacaactaca agaccacacc tcccatgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaa                                       1347
```

<210> SEQ ID NO 90
<211> LENGTH: 449
<212> TYPE: PRT
<213> ORGANISM: Artificial Sequence
<220> FEATURE:
<223> OTHER INFORMATION: Humanized antibody
<220> FEATURE:
<221> NAME/KEY: MISC_FEATURE
<223> OTHER INFORMATION: Ab-5 heavy chain

<400> SEQUENCE: 90

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
```

-continued

```
                35                  40                  45
Gly Glu Ile Asn Pro Asn Ser Gly Gly Ala Gly Tyr Asn Gln Lys Phe
 50                  55                  60

Lys Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Leu Gly Tyr Asp Asp Ile Tyr Asp Asp Trp Tyr Phe Asp Val
                100                 105                 110

Trp Gly Gln Gly Thr Thr Val Thr Val Ser Ser Ala Ser Thr Lys Gly
                115                 120                 125

Pro Ser Val Phe Pro Leu Ala Pro Cys Ser Arg Ser Thr Ser Glu Ser
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Asn Phe Gly Thr Gln Thr Tyr Thr Cys Asn Val
                195                 200                 205

Asp His Lys Pro Ser Asn Thr Lys Val Asp Lys Thr Val Glu Arg Lys
                210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Phe Asn Ser Thr Phe Arg Val
                290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys
```

```
<210> SEQ ID NO 91
<211> LENGTH: 11
<212> TYPE: PRT
<213> ORGANISM: Artificial Sequence
<220> FEATURE:
<223> OTHER INFORMATION: Ab-6 LCDR1

<400> SEQUENCE: 91

Arg Ala Ser Gln Asp Ile Ser Asn Tyr Leu Asn
1               5                   10

<210> SEQ ID NO 92
<211> LENGTH: 7
<212> TYPE: PRT
<213> ORGANISM: Artificial Sequence
<220> FEATURE:
<223> OTHER INFORMATION: Ab-6 LCDR2

<400> SEQUENCE: 92

Tyr Thr Ser Arg Leu His Ser
1               5

<210> SEQ ID NO 93
<211> LENGTH: 9
<212> TYPE: PRT
<213> ORGANISM: Artificial Sequence
<220> FEATURE:
<223> OTHER INFORMATION: Ab-6 LCDR3

<400> SEQUENCE: 93

Gln Gln Gly Asp Thr Leu Pro Tyr Thr
1               5

<210> SEQ ID NO 94
<211> LENGTH: 5
<212> TYPE: PRT
<213> ORGANISM: Artificial Sequence
<220> FEATURE:
<223> OTHER INFORMATION: Ab-6 HCDR1

<400> SEQUENCE: 94

Asp Tyr Asn Met His
1               5

<210> SEQ ID NO 95
<211> LENGTH: 17
<212> TYPE: PRT
<213> ORGANISM: Artificial Sequence
<220> FEATURE:
<223> OTHER INFORMATION: Ab-6 HCDR2

<400> SEQUENCE: 95

Glu Ile Asn Pro Asn Ser Gly Gly Ser Gly Tyr Asn Gln Lys Phe Lys
1               5                   10                  15

Gly

<210> SEQ ID NO 96
<211> LENGTH: 14
<212> TYPE: PRT
<213> ORGANISM: Artificial Sequence
<220> FEATURE:
<223> OTHER INFORMATION: Ab-6 HCDR3

<400> SEQUENCE: 96

Leu Val Tyr Asp Gly Ser Tyr Glu Asp Trp Tyr Phe Asp Val
1               5                   10
```

<210> SEQ ID NO 97
<211> LENGTH: 645
<212> TYPE: DNA
<213> ORGANISM: Mus musculus
<220> FEATURE:
<221> NAME/KEY: misc_feature
<223> OTHER INFORMATION: Ab-6 light chain

<400> SEQUENCE: 97

```
gatatccaga tgacacagac tacatcctcc ctgtctgcct ctctgggaga cagagtcacc      60
atcagttgca gggcaagtca ggacattagc aattatttaa actggtttca gcagaaacca     120
gatggaactc ttaaactcct gatcttctac acatcaagat tacactcagg agttccatca     180
aggttcagtg gcagtgggtc tggaacagat tattctctca ccattagcaa cctggagcaa     240
gaagatattg ccacttactt ttgccaacag ggtgatacgc ttccgtacac gttcgggggg     300
gggaccaagc tggaaataag acgggctgat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag cacccctcacg    540
ttgaccaagg acgagtatga acgacataac agctatacct gtgaggccac tcacaagaca     600
tcaacttcac ccattgtcaa gagcttcaac aggaatgagt gttag                     645
```

<210> SEQ ID NO 98
<211> LENGTH: 214
<212> TYPE: PRT
<213> ORGANISM: Mus musculus
<220> FEATURE:
<221> NAME/KEY: MISC_FEATURE
<223> OTHER INFORMATION: Ab-6 light chain

<400> SEQUENCE: 98

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Phe Gln Gln Lys Pro Asp Gly Thr Leu Lys Leu Leu Ile
        35                  40                  45

Phe Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asp Thr Leu Pro Tyr
                85                  90                  95

Thr Phe Gly Gly Gly Thr Lys Leu Glu Ile Arg Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
```

```
             180                 185                 190
Thr Cys Glu Ala Thr His Lys Thr Ser Thr Ser Pro Ile Val Lys Ser
                     195                 200                 205
Phe Asn Arg Asn Glu Cys
                 210
```

<210> SEQ ID NO 99
<211> LENGTH: 1344
<212> TYPE: DNA
<213> ORGANISM: Mus musculus
<220> FEATURE:
<221> NAME/KEY: misc_feature
<223> OTHER INFORMATION: Ab-6 heavy chain

<400> SEQUENCE: 99

| | | | | | |
|---|---|---|---|---|---|
| gaggtccagc | tgcaacagtc | tggacctgaa | ctaatgaagc | ctggggcttc | agtgaagatg | 60 |
| tcctgcaagg | cttctggata | cacattcact | gactacaaca | tgcactgggt | gaaacagaac | 120 |
| caaggaaaga | gcctagagtg | gataggagaa | attaatccta | acagtggtgg | tagtggctac | 180 |
| aaccaaaagt | tcaaaggcaa | ggccacattg | actgtagaca | agtcttccag | cacagcctac | 240 |
| atggagctcc | gcagcctgac | atctgaggac | tctgcagtct | attactgtgc | aagattggtc | 300 |
| tacgatggca | gctacgagga | ctggtacttc | gatgtctggg | gcgcagggac | cacggtcacc | 360 |
| gtctcctcag | ccaaaacgac | accccatct | gtctatccac | tggcccctgg | atctgctgcc | 420 |
| caaactaact | ccatggtgac | cctgggatgc | ctggtcaagg | gctatttccc | tgagccagtg | 480 |
| acagtgacct | ggaactctgg | atccctgtcc | agcggtgtgc | acaccttccc | agctgtcctg | 540 |
| cagtctgacc | tctacactct | gagcagctca | gtgactgtcc | cctccagcac | ctggcccagc | 600 |
| gagaccgtca | cctgcaacgt | tgcccacccg | gccagcagca | ccaaggtgga | caagaaaatt | 660 |
| gtgcccaggg | attgtggttg | taagccttgc | atatgtacag | tcccagaagt | atcatctgtc | 720 |
| ttcatcttcc | ccccaaagcc | caaggatgtg | ctcaccatta | ctctgactcc | taaggtcacg | 780 |
| tgtgttgtgg | tagacatcag | caaggatgat | cccgaggtcc | agttcagctg | gtttgtagat | 840 |
| gatgtggagg | tgcacacagc | tcagacgcaa | ccccgggagg | agcagttcaa | cagcactttc | 900 |
| cgctcagtca | gtgaacttcc | catcatgcac | caggactggc | tcaatggcaa | ggagttcaaa | 960 |
| tgcagggtca | acagtgcagc | tttccctgcc | cccatcgaga | aaaccatctc | caaaaccaaa | 1020 |
| ggcagaccga | aggctccaca | ggtgtacacc | attccacctc | ccaaggagca | gatggccaag | 1080 |
| gataaagtca | gtctgacctg | catgataaca | gacttcttcc | ctgaagacat | tactgtggag | 1140 |
| tggcagtgga | atgggcagcc | agcggagaac | tacaagaaca | ctcagcccat | catggacaca | 1200 |
| gatggctctt | acttcatcta | cagcaagctc | aatgtgcaga | agagcaactg | ggaggcagga | 1260 |
| aatactttca | cctgctctgt | gttacatgag | ggcctgcaca | accaccatac | tgagaagagc | 1320 |
| ctctcccact | ctcctggtaa | atga | | | | 1344 |

<210> SEQ ID NO 100
<211> LENGTH: 447
<212> TYPE: PRT
<213> ORGANISM: Mus musculus
<220> FEATURE:
<221> NAME/KEY: MISC_FEATURE
<223> OTHER INFORMATION: Ab-6 heavy chain

<400> SEQUENCE: 100

```
Glu Val Gln Leu Gln Gln Ser Gly Pro Glu Leu Met Lys Pro Gly Ala
1               5                  10                  15
```

-continued

```
Ser Val Lys Met Ser Cys Lys Ala Ser Gly Tyr Thr Phe Thr Asp Tyr
            20                  25                  30

Asn Met His Trp Val Lys Gln Asn Gly Lys Ser Leu Glu Trp Ile
            35                  40                  45

Gly Glu Ile Asn Pro Asn Ser Gly Gly Ser Gly Tyr Asn Gln Lys Phe
            50                  55                  60

Lys Gly Lys Ala Thr Leu Thr Val Asp Lys Ser Ser Ser Thr Ala Tyr
 65                  70                  75                  80

Met Glu Leu Arg Ser Leu Thr Ser Glu Asp Ser Ala Val Tyr Tyr Cys
                85                  90                  95

Ala Arg Leu Val Tyr Asp Gly Ser Tyr Glu Asp Trp Tyr Phe Asp Val
                100                 105                 110

Trp Gly Ala Gly Thr Thr Val Thr Val Ser Ser Ala Lys Thr Thr Pro
            115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
                180                 185                 190

Val Pro Ser Ser Thr Trp Pro Ser Glu Thr Val Thr Cys Asn Val Ala
            195                 200                 205

His Pro Ala Ser Ser Thr Lys Val Asp Lys Lys Ile Val Pro Arg Asp
210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
```

```
<210> SEQ ID NO 101
<211> LENGTH: 11
<212> TYPE: PRT
<213> ORGANISM: Artificial Sequence
<220> FEATURE:
<223> OTHER INFORMATION: Ab-7 LCDR1

<400> SEQUENCE: 101

Arg Ala Ser Gln Val Ile Thr Asn Tyr Leu Tyr
1               5                   10

<210> SEQ ID NO 102
<211> LENGTH: 7
<212> TYPE: PRT
<213> ORGANISM: Artificial Sequence
<220> FEATURE:
<223> OTHER INFORMATION: Ab-7 LCDR2

<400> SEQUENCE: 102

Tyr Thr Ser Arg Leu His Ser
1               5

<210> SEQ ID NO 103
<211> LENGTH: 9
<212> TYPE: PRT
<213> ORGANISM: Artificial Sequence
<220> FEATURE:
<223> OTHER INFORMATION: Ab-7 LCDR3

<400> SEQUENCE: 103

Gln Gln Gly Asp Thr Leu Pro Tyr Thr
1               5

<210> SEQ ID NO 104
<211> LENGTH: 5
<212> TYPE: PRT
<213> ORGANISM: Artificial Sequence
<220> FEATURE:
<223> OTHER INFORMATION: Ab-7 HCDR1

<400> SEQUENCE: 104

Asp Tyr Asn Met His
1               5

<210> SEQ ID NO 105
<211> LENGTH: 17
<212> TYPE: PRT
<213> ORGANISM: Artificial Sequence
<220> FEATURE:
<223> OTHER INFORMATION: Ab-7 HCDR2

<400> SEQUENCE: 105

Glu Ile Asn Pro Asn Ser Gly Gly Ala Gly Tyr Asn Gln Gln Phe Lys
1               5                   10                  15

Gly

<210> SEQ ID NO 106
<211> LENGTH: 14
<212> TYPE: PRT
<213> ORGANISM: Artificial Sequence
<220> FEATURE:
<223> OTHER INFORMATION: Ab-7 HCDR3

<400> SEQUENCE: 106
```

```
Leu Gly Tyr Val Gly Asn Tyr Glu Asp Trp Tyr Phe Asp Val
 1               5                  10
```

<210> SEQ ID NO 107
<211> LENGTH: 642
<212> TYPE: DNA
<213> ORGANISM: Mus musculus
<220> FEATURE:
<221> NAME/KEY: misc_feature
<223> OTHER INFORMATION: Ab-7 light chain

<400> SEQUENCE: 107

```
gatatccaga tgacacagac tacatcctcc ctgtctgcct ctctgggaga cagagtcacc      60
atctgttgca gggcaagtca ggtcattacc aattatttat actggtatca gcagaaacca     120
gatggaactt ttaaactcct gatctactac acatcaagat acactcagg agtcccatca      180
aggttcagtg gcagtgggtc tggaacagat tattctctca ccattagcaa cctgaacag      240
gaagatattg ccacttactt ttgccaacag ggtgatacgc ttccgtacac gttcggaggg     300
gggaccaagc tggaaataaa acgggctgat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag caccctcacg     540
ttgaccaagg acgagtatga cgacataac agctatacct gtgaggccac tcacaagaca     600
tcaacttcac ccattgtcaa gagcttcaac aggaatgagt gt                       642
```

<210> SEQ ID NO 108
<211> LENGTH: 214
<212> TYPE: PRT
<213> ORGANISM: Mus musculus
<220> FEATURE:
<221> NAME/KEY: MISC_FEATURE
<223> OTHER INFORMATION: Ab-7 light chain

<400> SEQUENCE: 108

```
Asp Ile Gln Met Thr Gln Thr Thr Ser Ser Leu Ser Ala Ser Leu Gly
 1               5                  10                  15

Asp Arg Val Thr Ile Cys Cys Arg Ala Ser Gln Val Ile Thr Asn Tyr
             20                  25                  30

Leu Tyr Trp Tyr Gln Gln Lys Pro Asp Gly Thr Phe Lys Leu Leu Ile
         35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asp Thr Leu Pro Tyr
                 85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175
```

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 109
<211> LENGTH: 1341
<212> TYPE: DNA
<213> ORGANISM: Mus musculus
<220> FEATURE:
<221> NAME/KEY: misc_feature
<223> OTHER INFORMATION: Ab-7 heavy chain

<400> SEQUENCE: 109

```
gaggtccagc tgcaacagtc tggacctgaa ctaatgaagc ctggggcttc agtgaagatg      60
tcctgcaagg cttctggata cacattcact gactacaaca tgcactggat gaagcagaac     120
caaggaaaga gcctagaatg gataggagaa attaatccta cagtggtgg tgctggctac      180
aaccagcagt tcaaaggcaa ggccacattg actgtagaca gtcctccag acagcctac      240
atggagctcc gcagcctgac atctgaggac tctgcagtct attactgtgc aagattgggc    300
tacgttggta attacgagga ctggtacttc gatgtctggg gcgcagggac cacggtcacc    360
gtctcctcag ccaaaacgac accccatct gtctatccac tggcccctgg atctgctgcc     420
caaactaact ccatggtgac cctgggatgc ctggtcaagg ctatttccc tgagccagtg     480
acagtgacct ggaactctgg atccctgtcc agcggtgtgc acaccttccc agctgtcctg    540
cagtctgacc tctacactct gagcagctca gtgactgtcc cctccagcac ctggcccagc    600
gagaccgtca cctgcaacgt tgcccacccg gccagcagca ccaaggtgga agaaaatt     660
gtgcccaggg attgtggttg taagccttgc atatgtacag tcccagaagt atcatctgtc   720
ttcatcttcc ccccaaagcc caaggatgtg ctcaccatta ctctgactcc taaggtcacg    780
tgtgttgtgg tagacatcag caaggatgat cccgaggtcc agttcagctg gtttgtagat    840
gatgtggagg tgcacacagc tcagacgcaa ccccgggagg agcagttcaa cagcactttc    900
cgctcagtca gtgaacttcc catcatgcac caggactggc tcaatggcaa ggagttcaaa    960
tgcagggtca acagtgcagc tttccctgcc cccatcgaga aaaccatctc caaaaccaaa   1020
ggcagaccga aggctccaca ggtgtacacc attccacctc ccaaggagca gatggccaag   1080
gataaagtca gtctgacctg catgataaca gacttcttcc ctgaagacat tactgtggag   1140
tggcagtgga atgggcagcc agcggagaac tacaagaaca ctcagcccat catggacaca   1200
gatggctctt acttcatcta cagcaagctc aatgtgcaga gagcaactg ggaggcagga   1260
aatactttca cctgctctgt gttacatgag ggcctgcaca accaccatac tgagaagagc   1320
ctctcccact ctcctggtaa a                                              1341
```

<210> SEQ ID NO 110
<211> LENGTH: 447
<212> TYPE: PRT
<213> ORGANISM: Mus musculus
<220> FEATURE:
<221> NAME/KEY: MISC_FEATURE
<223> OTHER INFORMATION: Ab-7 heavy chain

<400> SEQUENCE: 110

Glu Val Gln Leu Gln Gln Ser Gly Pro Glu Leu Met Lys Pro Gly Ala

-continued

```
  1               5                  10                 15
Ser Val Lys Met Ser Cys Lys Ala Ser Gly Tyr Thr Phe Thr Asp Tyr
                 20                 25                 30
Asn Met His Trp Met Lys Gln Asn Gln Gly Lys Ser Leu Glu Trp Ile
                 35                 40                 45
Gly Glu Ile Asn Pro Asn Ser Gly Gly Ala Gly Tyr Asn Gln Gln Phe
                 50                 55                 60
Lys Gly Lys Ala Thr Leu Thr Val Asp Lys Ser Ser Arg Thr Ala Tyr
 65                 70                 75                 80
Met Glu Leu Arg Ser Leu Thr Ser Glu Asp Ser Ala Val Tyr Tyr Cys
                 85                 90                 95
Ala Arg Leu Gly Tyr Val Gly Asn Tyr Glu Asp Trp Tyr Phe Asp Val
                100                105                110
Trp Gly Ala Gly Thr Thr Val Thr Val Ser Ser Ala Lys Thr Thr Pro
                115                120                125
Pro Ser Val Tyr Pro Leu Ala Pro Gly Ser Ala Ala Gln Thr Asn Ser
                130                135                140
Met Val Thr Leu Gly Cys Leu Val Lys Gly Tyr Phe Pro Glu Pro Val
145                150                155                160
Thr Val Thr Trp Asn Ser Gly Ser Leu Ser Ser Gly Val His Thr Phe
                165                170                175
Pro Ala Val Leu Gln Ser Asp Leu Tyr Thr Leu Ser Ser Ser Val Thr
                180                185                190
Val Pro Ser Ser Thr Trp Pro Ser Glu Thr Val Thr Cys Asn Val Ala
                195                200                205
His Pro Ala Ser Ser Thr Lys Val Asp Lys Lys Ile Val Pro Arg Asp
210                215                220
Cys Gly Cys Lys Pro Cys Ile Cys Thr Val Pro Glu Val Ser Ser Val
225                230                235                240
Phe Ile Phe Pro Pro Lys Pro Lys Asp Val Leu Thr Ile Thr Leu Thr
                245                250                255
Pro Lys Val Thr Cys Val Val Val Asp Ile Ser Lys Asp Asp Pro Glu
                260                265                270
Val Gln Phe Ser Trp Phe Val Asp Asp Val Glu Val His Thr Ala Gln
                275                280                285
Thr Gln Pro Arg Glu Glu Gln Phe Asn Ser Thr Phe Arg Ser Val Ser
                290                295                300
Glu Leu Pro Ile Met His Gln Asp Trp Leu Asn Gly Lys Glu Phe Lys
305                310                315                320
Cys Arg Val Asn Ser Ala Ala Phe Pro Ala Pro Ile Glu Lys Thr Ile
                325                330                335
Ser Lys Thr Lys Gly Arg Pro Lys Ala Pro Gln Val Tyr Thr Ile Pro
                340                345                350
Pro Pro Lys Glu Gln Met Ala Lys Asp Lys Val Ser Leu Thr Cys Met
                355                360                365
Ile Thr Asp Phe Phe Pro Glu Asp Ile Thr Val Glu Trp Gln Trp Asn
                370                375                380
Gly Gln Pro Ala Glu Asn Tyr Lys Asn Thr Gln Pro Ile Met Asp Thr
385                390                395                400
Asp Gly Ser Tyr Phe Ile Tyr Ser Lys Leu Asn Val Gln Lys Ser Asn
                405                410                415
Trp Glu Ala Gly Asn Thr Phe Thr Cys Ser Val Leu His Glu Gly Leu
                420                425                430
```

His Asn His His Thr Glu Lys Ser Leu Ser His Ser Pro Gly Lys
        435                 440                 445

<210> SEQ ID NO 111
<211> LENGTH: 11
<212> TYPE: PRT
<213> ORGANISM: Artificial Sequence
<220> FEATURE:
<223> OTHER INFORMATION: Ab-8 LCDR1

<400> SEQUENCE: 111

Arg Ala Ser Gln Asp Ile Ser Asn Tyr Leu Asn
1               5                   10

<210> SEQ ID NO 112
<211> LENGTH: 7
<212> TYPE: PRT
<213> ORGANISM: Artificial Sequence
<220> FEATURE:
<223> OTHER INFORMATION: Ab-8 LCDR2

<400> SEQUENCE: 112

Tyr Thr Ser Arg Leu Leu Ser
1               5

<210> SEQ ID NO 113
<211> LENGTH: 9
<212> TYPE: PRT
<213> ORGANISM: Artificial Sequence
<220> FEATURE:
<223> OTHER INFORMATION: Ab-8 LCDR3

<400> SEQUENCE: 113

Gln Gln Gly Asp Thr Leu Pro Tyr Thr
1               5

<210> SEQ ID NO 114
<211> LENGTH: 5
<212> TYPE: PRT
<213> ORGANISM: Artificial Sequence
<220> FEATURE:
<223> OTHER INFORMATION: Ab-8 HCDR1

<400> SEQUENCE: 114

Asp Tyr Asn Met His
1               5

<210> SEQ ID NO 115
<211> LENGTH: 17
<212> TYPE: PRT
<213> ORGANISM: Artificial Sequence
<220> FEATURE:
<223> OTHER INFORMATION: Ab-8 HCDR2

<400> SEQUENCE: 115

Glu Ile Asn Pro Asn Ser Gly Gly Ala Gly Tyr Asn Gln Lys Phe Lys
1               5                   10                  15

Gly

<210> SEQ ID NO 116
<211> LENGTH: 14
<212> TYPE: PRT
<213> ORGANISM: Artificial Sequence
<220> FEATURE:
<223> OTHER INFORMATION: Ab-8 HCDR3

<400> SEQUENCE: 116

Leu Gly Tyr Asp Asp Ile Tyr Asp Asp Trp Tyr Phe Asp Val
1               5                   10

<210> SEQ ID NO 117
<211> LENGTH: 645
<212> TYPE: DNA
<213> ORGANISM: Mus musculus
<220> FEATURE:
<221> NAME/KEY: misc_feature
<223> OTHER INFORMATION: Ab-8 light chain

<400> SEQUENCE: 117

```
gatatccaga tgacacagac tacatcctcc ctgtctgcct ctctgggaga cagggtctcc    60
atcagttgca gggcaagtca agacattagc aattatttaa actggtatca gcagaaacca   120
gatggaactt ttaaactcct tatcttctac acatcaagat tactctcagg agtcccatca   180
aggttcagtg gcagtgggtc tggaacagat tattctctca ccatttacaa cctggagcaa   240
gaagattttg ccacttactt ttgccaacag ggagatacgc ttccgtacac tttcggaggg   300
gggaccaaac tggaaataaa acgggctgat gctgcaccaa ctgtatccat cttcccacca   360
tccagtgagc agttaacatc tggaggtgcc tcagtcgtgt gcttcttgaa caacttctac   420
cccaaagaca tcaatgtcaa gtggaagatt gatggcagtg aacgacaaaa tggcgtcctg   480
aacagttgga ctgatcagga cagcaaagac agcacctaca gcatgagcag caccctcacg   540
ttgaccaagg acgagtatga acgacataac agctatacct gtgaggccac tcacaagaca   600
tcaacttcac ccattgtcaa gagcttcaac aggaatgagt gttag                   645
```

<210> SEQ ID NO 118
<211> LENGTH: 214
<212> TYPE: PRT
<213> ORGANISM: Mus musculus
<220> FEATURE:
<221> NAME/KEY: MISC_FEATURE
<223> OTHER INFORMATION: Ab-8 light chain

<400> SEQUENCE: 118

Asp Ile Gln Met Thr Gln Thr Thr Ser Ser Leu Ser Ala Ser Leu Gly
1               5                   10                  15

Asp Arg Val Ser Ile Ser Cys Arg Ala Ser Gln Asp Ile Ser Asn Tyr
            20                  25                  30

Leu Asn Trp Tyr Gln Gln Lys Pro Asp Gly Thr Phe Lys Leu Leu Ile
        35                  40                  45

Phe Tyr Thr Ser Arg Leu Leu Ser Gly Val Pro Ser Arg Phe Ser Gly
    50                  55                  60

Ser Gly Ser Gly Thr Asp Tyr Ser Leu Thr Ile Tyr Asn Leu Glu Gln
65                  70                  75                  80

Glu Asp Phe Ala Thr Tyr Phe Cys Gln Gln Gly Asp Thr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
    210

<210> SEQ ID NO 119
<211> LENGTH: 1344
<212> TYPE: DNA
<213> ORGANISM: Mus musculus
<220> FEATURE:
<221> NAME/KEY: misc_feature
<223> OTHER INFORMATION: Ab-8 heavy chain

<400> SEQUENCE: 119

| gaggtccaac tgcaacagtc tggacctgaa ctaatgaagc ctggggcttc agtgaagatg | 60 |
| tcctgcaagg cttctggata cattcact gactacaaca tgcactgggt gaagcagaac | 120 |
| caaggaaaga ccctagactg ataggagaaa attaatccta acagtggtgg tgctggctac | 180 |
| aaccagaagt tcaagggcaa ggccacattg actgtagaca agtcctccac cacagcctac | 240 |
| atggagctcc gcagcctgac atctgaggac tctgcagtct attactgtgc aagattgggc | 300 |
| tacgatgata tctacgacga ctggtacttc gatgtctggg gcgcaggga cacggtcacc | 360 |
| gtctcctcag ccaaaacgac cccccatct gtctatccac tggcccctgg atctgctgcc | 420 |
| caaactaact ccatggtgac cctgggatgc ctggtcaagg gctatttccc tgagccagtg | 480 |
| acagtgacct ggaactctgg atccctgtcc agcggtgtgc acaccttccc agctgtcctg | 540 |
| cagtctgacc tctacactct gagcagctca gtgactgtcc cctccagcac ctggcccagc | 600 |
| gagaccgtca cctgcaacgt tgcccacccg gccagcagca ccaaggtgga caagaaaatt | 660 |
| gtgcccaggg attgtggttg taagccttgc atatgtacag tcccagaagt atcatctgtc | 720 |
| ttcatcttcc ccccaaagcc caaggatgtg ctcaccatta ctctgactcc taaggtcacg | 780 |
| tgtgttgtgg tagacatcag caaggatgat cccgaggtcc agttcagctg gtttgtagat | 840 |
| gatgtggagg tgcacacagc tcagacgcaa ccccgggagg agcagttcaa cagcactttc | 900 |
| cgctcagtca gtgaacttcc catcatgcac caggactggc tcaatggcaa ggagttcaaa | 960 |
| tgcagggtca acagtgcagc tttccctgcc cccatcgaga aaaccatctc caaaaccaaa | 1020 |
| ggcagaccga aggctccaca ggtgtacacc attccacctc ccaaggagca gatggccaag | 1080 |
| gataaagtca gtctgacctg catgataaca gacttcttcc ctgaagacat tactgtggag | 1140 |
| tggcagtgga atgggcagcc agcggagaac tacaagaaca ctcagcccat catggacaca | 1200 |
| gatggctctt acttcatcta cagcaagctc aatgtgcaga gagcaactg ggaggcagga | 1260 |
| aatactttca cctgctctgt gttacatgag ggcctgcaca accaccatac tgagaagagc | 1320 |
| ctctcccact ctcctggtaa atga | 1344 |

<210> SEQ ID NO 120
<211> LENGTH: 447
<212> TYPE: PRT
<213> ORGANISM: Mus musculus
<220> FEATURE:
<221> NAME/KEY: MISC_FEATURE
<223> OTHER INFORMATION: Ab-8 heavy chain

<400> SEQUENCE: 120

-continued

```
Glu Val Gln Leu Gln Gln Ser Gly Pro Glu Leu Met Lys Pro Gly Ala
1               5                   10                  15
Ser Val Lys Met Ser Cys Lys Ala Ser Gly Tyr Thr Phe Thr Asp Tyr
            20                  25                  30
Asn Met His Trp Val Lys Gln Asn Gly Lys Thr Leu Asp Trp Ile
        35                  40                  45
Gly Glu Ile Asn Pro Asn Ser Gly Ala Gly Tyr Asn Gln Lys Phe
50                  55                  60
Lys Gly Lys Ala Thr Leu Thr Val Asp Lys Ser Ser Thr Thr Ala Tyr
65                  70                  75                  80
Met Glu Leu Arg Ser Leu Thr Ser Glu Asp Ser Ala Val Tyr Tyr Cys
                85                  90                  95
Ala Arg Leu Gly Tyr Asp Asp Ile Tyr Asp Asp Trp Tyr Phe Asp Val
                100                 105                 110
Trp Gly Ala Gly Thr Thr Val Thr Val Ser Ser Ala Lys Thr Thr Pro
            115                 120                 125
Pro Ser Val Tyr Pro Leu Ala Pro Gly Ser Ala Ala Gln Thr Asn Ser
    130                 135                 140
Met Val Thr Leu Gly Cys Leu Val Lys Gly Tyr Phe Pro Glu Pro Val
145                 150                 155                 160
Thr Val Thr Trp Asn Ser Gly Ser Leu Ser Ser Gly Val His Thr Phe
                165                 170                 175
Pro Ala Val Leu Gln Ser Asp Leu Tyr Thr Leu Ser Ser Ser Val Thr
                180                 185                 190
Val Pro Ser Ser Thr Trp Pro Ser Glu Thr Val Thr Cys Asn Val Ala
            195                 200                 205
His Pro Ala Ser Ser Thr Lys Val Asp Lys Lys Ile Val Pro Arg Asp
210                 215                 220
Cys Gly Cys Lys Pro Cys Ile Cys Thr Val Pro Glu Val Ser Ser Val
225                 230                 235                 240
Phe Ile Phe Pro Pro Lys Pro Lys Asp Val Leu Thr Ile Thr Leu Thr
                245                 250                 255
Pro Lys Val Thr Cys Val Val Val Asp Ile Ser Lys Asp Asp Pro Glu
            260                 265                 270
Val Gln Phe Ser Trp Phe Val Asp Asp Val Glu Val His Thr Ala Gln
        275                 280                 285
Thr Gln Pro Arg Glu Glu Gln Phe Asn Ser Thr Phe Arg Ser Val Ser
    290                 295                 300
Glu Leu Pro Ile Met His Gln Asp Trp Leu Asn Gly Lys Glu Phe Lys
305                 310                 315                 320
Cys Arg Val Asn Ser Ala Ala Phe Pro Ala Pro Ile Glu Lys Thr Ile
                325                 330                 335
Ser Lys Thr Lys Gly Arg Pro Lys Ala Pro Gln Val Tyr Thr Ile Pro
            340                 345                 350
Pro Pro Lys Glu Gln Met Ala Lys Asp Lys Val Ser Leu Thr Cys Met
        355                 360                 365
Ile Thr Asp Phe Phe Pro Glu Asp Ile Thr Val Glu Trp Gln Trp Asn
    370                 375                 380
Gly Gln Pro Ala Glu Asn Tyr Lys Asn Thr Gln Pro Ile Met Asp Thr
385                 390                 395                 400
Asp Gly Ser Tyr Phe Ile Tyr Ser Lys Leu Asn Val Gln Lys Ser Asn
                405                 410                 415
```

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
            435                 440                 445

<210> SEQ ID NO 121
<211> LENGTH: 11
<212> TYPE: PRT
<213> ORGANISM: Artificial Sequence
<220> FEATURE:
<223> OTHER INFORMATION: Ab-9 LCDR1

<400> SEQUENCE: 121

Arg Ala Ser Gln Asp Ile Ser Asn Tyr Leu Asn
1               5                   10

<210> SEQ ID NO 122
<211> LENGTH: 7
<212> TYPE: PRT
<213> ORGANISM: Artificial Sequence
<220> FEATURE:
<223> OTHER INFORMATION: Ab-9 LCDR2

<400> SEQUENCE: 122

Tyr Thr Ser Arg Leu Phe Ser
1               5

<210> SEQ ID NO 123
<211> LENGTH: 9
<212> TYPE: PRT
<213> ORGANISM: Artificial Sequence
<220> FEATURE:
<223> OTHER INFORMATION: Ab-9 LCDR3

<400> SEQUENCE: 123

Gln Gln Gly Asp Thr Leu Pro Tyr Thr
1               5

<210> SEQ ID NO 124
<211> LENGTH: 5
<212> TYPE: PRT
<213> ORGANISM: Artificial Sequence
<220> FEATURE:
<223> OTHER INFORMATION: Ab-9 HCDR1

<400> SEQUENCE: 124

Asp Tyr Asn Met His
1               5

<210> SEQ ID NO 125
<211> LENGTH: 17
<212> TYPE: PRT
<213> ORGANISM: Artificial Sequence
<220> FEATURE:
<223> OTHER INFORMATION: Ab-9 HCDR2

<400> SEQUENCE: 125

Glu Ile Asn Pro Asn Ser Gly Gly Ala Gly Tyr Asn Gln Lys Phe Lys
1               5                   10                  15

Gly

<210> SEQ ID NO 126
<211> LENGTH: 14
<212> TYPE: PRT
<213> ORGANISM: Artificial Sequence
<220> FEATURE:

<223> OTHER INFORMATION: Ab-9 HCDR3

<400> SEQUENCE: 126

Leu Gly Tyr Asp Asp Ile Tyr Asp Asp Trp Tyr Phe Asp Val
1               5                   10

<210> SEQ ID NO 127
<211> LENGTH: 642
<212> TYPE: DNA
<213> ORGANISM: Mus musculus

<400> SEQUENCE: 127

```
gatatccaga tgacacagat tacatcctcc ctgtctgcct ctctgggaga cagggtctcc    60
atcagttgca gggcaagtca agacattagc aattatttaa attggtatca gcagaaacca   120
gatggaactt ttaaactcct tatcttctac acatcaagat tatttcagg agtcccatca    180
aggttcagtg gcagtgggtc tggaacagat tattctctca ccatttacaa cctggagcaa   240
gaagattttg ccacttactt ttgccaacag ggagatacgc ttccgtacac tttcggaggg   300
gggaccaagg tggaaataaa acgggctgat gctgcaccaa ctgtatccat cttcccacca   360
tccagtgagc agttaacatc tggaggtgcc tcagtcgtgt gcttcttgaa caacttctac   420
cccaaagaca tcaatgtcaa gtggaagatt gatggcagtg aacgacaaaa tggcgtcctg   480
aacagttgga ctgatcagga cagcaaagac agcacctaca gcatgagcag caccctcacg   540
ttgaccaagg acgagtatga acgacataac agctatacct gtgaggccac tcacaagaca   600
tcaacttcac ccattgtcaa gagcttcaac aggaatgagt gt                      642
```

<210> SEQ ID NO 128
<211> LENGTH: 214
<212> TYPE: PRT
<213> ORGANISM: Mus musculus

<400> SEQUENCE: 128

Asp Ile Gln Met Thr Gln Ile Thr Ser Ser Leu Ser Ala Ser Leu Gly
1               5                   10                  15

Asp Arg Val Ser Ile Ser Cys Arg Ala Ser Gln Asp Ile Ser Asn Tyr
            20                  25                  30

Leu Asn Trp Tyr Gln Gln Lys Pro Asp Gly Thr Phe Lys Leu Leu Ile
        35                  40                  45

Phe Tyr Thr Ser Arg Leu Phe Ser Gly Val Pro Ser Arg Phe Ser Gly
    50                  55                  60

Ser Gly Ser Gly Thr Asp Tyr Ser Leu Thr Ile Tyr Asn Leu Glu Gln
65                  70                  75                  80

Glu Asp Phe Ala Thr Tyr Phe Cys Gln Gln Gly Asp Thr Leu Pro Tyr
                85                  90                  95

Thr Phe Gly Gly Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr 180                 185                 190
Thr Cys Glu Ala Thr His Lys Thr Ser Thr Ser Pro Ile Val Lys Ser
        195                 200                 205

Phe Asn Arg Asn Glu Cys
    210

<210> SEQ ID NO 129
<211> LENGTH: 1350
<212> TYPE: DNA
<213> ORGANISM: Mus musculus

<400> SEQUENCE: 129
gaggtccaac tgcaacagtc tggacctgaa ctaatgaagc ctgggacttc agtgaagatg      60
tcctgcaagg cttctggata tacattcact gactacaaca tgcactgggt gaagcagacc     120
caaggaaaga ccctagagtg gataggagaa attaatccta cagtggtggt gctggctac      180
aaccagaagt tcaagggcaa ggccacattg actgtagaca gtcctccac cacagcctac      240
atggagctcc gcagcctgac atctgaggac tctgcagtct attactgtgc aaaattgggc     300
tacgatgata tctacgacga ctggtatttc gatgtctggg gcgcagggac cacggtcacc     360
gtctcctcag ccaaaacaac agccccatcg gtctatccac tggcccctgt gtgtggagat     420
acaactggct cctcggtgac tctaggatgc ctggtcaagg gttatttccc tgagccagtg     480
accttgacct ggaactctgg atccctgtcc agtgatgtgc acaccttccc agctctcctg     540
cagtctggcc tctacaccct cagcagctca gtgactgtaa ccacctggcc agccagacc      600
atcacctgca atgtggccca cccggcaagc agcaccaaag tggacaagaa aattgagccc     660
agagggtccc caacacataa accctgtcct ccatgcccag ctcctaacct cttgggtgga     720
ccatccgtct tcatcttccc tccaaagatc aaggatgtac tcatgatctc cctgagcccc     780
atggtcacgt gtgtggtggt ggatgtgagc gaggatgacc cagatgtcca tgtcagctgg     840
ttcgtgaaca acgtggaagt acacacagct cagacacaaa cccatagaga ggattacaac     900
agtactatcc gggtggtcag tgccctcccc atccagcacc aggactggat gagtggcaag     960
gagttcaaat gcaaggtcaa caacaaagcc ctcccagcgc ccatcgagag aaccatctca    1020
aaacccaaag ggcagtaag agctccacag gtatatgtct tgcctccacc agaagaagag    1080
atgactaaga aacaggtcac tctgacctgc atgatcacag acttcatgcc tgaagacatt    1140
tacgtggagt ggaccaacaa cgggcaaaca gagctaaact acaagaacac tgaaccagtc    1200
ctggactctg atggttctta cttcatgtac agcaagctga gagtgaaaaa gaagaactgg    1260
gtggaaagaa atagctactc ctgttcagtg gtccacgagg gtctgcacaa tcaccacacg    1320
actaagagct ctcccggac tccgggtaaa                                      1350

<210> SEQ ID NO 130
<211> LENGTH: 450
<212> TYPE: PRT
<213> ORGANISM: Mus musculus

<400> SEQUENCE: 130

Glu Val Gln Leu Gln Gln Ser Gly Pro Glu Leu Met Lys Pro Gly Thr
1               5                   10                  15

Ser Val Lys Met Ser Cys Lys Ala Ser Gly Tyr Thr Phe Thr Asp Tyr
            20                  25                  30

Asn Met His Trp Val Lys Gln Thr Gln Gly Lys Thr Leu Glu Trp Ile
        35                  40                  45

```
Gly Glu Ile Asn Pro Asn Ser Gly Gly Ala Gly Tyr Asn Gln Lys Phe
 50                  55                  60

Lys Gly Lys Ala Thr Leu Thr Val Asp Lys Ser Ser Thr Thr Ala Tyr
 65                  70                  75                  80

Met Glu Leu Arg Ser Leu Thr Ser Glu Asp Ser Ala Val Tyr Tyr Cys
                 85                  90                  95

Ala Lys Leu Gly Tyr Asp Asp Ile Tyr Asp Asp Trp Tyr Phe Asp Val
            100                 105                 110

Trp Gly Ala Gly Thr Thr Val Thr Val Ser Ser Ala Lys Thr Thr Ala
            115                 120                 125

Pro Ser Val Tyr Pro Leu Ala Pro Val Cys Gly Asp Thr Thr Gly Ser
130                 135                 140

Ser Val Thr Leu Gly Cys Leu Val Lys Gly Tyr Phe Pro Glu Pro Val
145                 150                 155                 160

Thr Leu Thr Trp Asn Ser Gly Ser Leu Ser Ser Asp Val His Thr Phe
                165                 170                 175

Pro Ala Leu Leu Gln Ser Gly Leu Tyr Thr Leu Ser Ser Ser Val Thr
            180                 185                 190

Val Thr Thr Trp Pro Ser Gln Thr Ile Thr Cys Asn Val Ala His Pro
            195                 200                 205

Ala Ser Ser Thr Lys Val Asp Lys Lys Ile Glu Pro Arg Gly Ser Pro
210                 215                 220

Thr His Lys Pro Cys Pro Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Met Val Thr Cys Val Val Val Asp Val Ser Glu Asp
            260                 265                 270

Asp Pro Asp Val His Val Ser Trp Phe Val Asn Asn Val Glu Val His
            275                 280                 285

Thr Ala Gln Thr Gln Thr His Arg Glu Asp Tyr Asn Ser Thr Ile Arg
290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Ala Leu Pro Ala Pro Ile Glu
                325                 330                 335

Arg Thr Ile Ser Lys Pro Lys Gly Pro Val Arg Ala Pro Gln Val Tyr
            340                 345                 350

Val Leu Pro Pro Pro Glu Glu Glu Met Thr Lys Lys Gln Val Thr Leu
            355                 360                 365

Thr Cys Met Ile Thr Asp Phe Met Pro Glu Asp Ile Tyr Val Glu Trp
370                 375                 380

Thr Asn Asn Gly Gln Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
            435                 440                 445

Gly Lys
450
```

-continued

<210> SEQ ID NO 131
<211> LENGTH: 11
<212> TYPE: PRT
<213> ORGANISM: Artificial Sequence
<220> FEATURE:
<223> OTHER INFORMATION: Ab-10 LCDR1

<400> SEQUENCE: 131

Arg Ala Ser Gln Asp Ile Ser Asn Tyr Leu Asn
1               5                   10

<210> SEQ ID NO 132
<211> LENGTH: 7
<212> TYPE: PRT
<213> ORGANISM: Artificial Sequence
<220> FEATURE:
<223> OTHER INFORMATION: Ab-10 LCDR2

<400> SEQUENCE: 132

Tyr Thr Ser Arg Leu Leu Ser
1               5

<210> SEQ ID NO 133
<211> LENGTH: 9
<212> TYPE: PRT
<213> ORGANISM: Artificial Sequence
<220> FEATURE:
<223> OTHER INFORMATION: Ab-10 LCDR3

<400> SEQUENCE: 133

Gln Gln Gly Asp Thr Leu Pro Tyr Thr
1               5

<210> SEQ ID NO 134
<211> LENGTH: 5
<212> TYPE: PRT
<213> ORGANISM: Artificial Sequence
<220> FEATURE:
<223> OTHER INFORMATION: Ab-10 HCDR1

<400> SEQUENCE: 134

Asp Tyr Asn Met His
1               5

<210> SEQ ID NO 135
<211> LENGTH: 17
<212> TYPE: PRT
<213> ORGANISM: Artificial Sequence
<220> FEATURE:
<223> OTHER INFORMATION: Ab-10 HCDR2

<400> SEQUENCE: 135

Glu Ile Asn Pro Asn Ser Gly Gly Ala Gly Tyr Asn Gln Lys Phe Lys
1               5                   10                  15

Gly

<210> SEQ ID NO 136
<211> LENGTH: 14
<212> TYPE: PRT
<213> ORGANISM: Artificial Sequence
<220> FEATURE:
<223> OTHER INFORMATION: Ab-10 HCDR3

<400> SEQUENCE: 136

Leu Gly Tyr Asp Asp Ile Tyr Asp Asp Trp Tyr Phe Asp Val
1               5                   10

<210> SEQ ID NO 137
<211> LENGTH: 645
<212> TYPE: DNA
<213> ORGANISM: Mus musculus

<400> SEQUENCE: 137

```
gatatccaga tgacacagac tacatcctcc ctgtctgcct ctctgggaga cagggtctcc     60
atcagttgca gggcaagtca agacattagc aattatttaa actggtatca gcagaaacca    120
gatggaactt ttaaactcct tatcttctac acatcaagat tactctcagg agtcccatca    180
aggttcagtg gcagtgggtc tggaacagat tattctctca ccatttacaa cctggagcaa    240
gaagattttg ccacttactt ttgccaacag ggagatacgc ttccgtacac tttcggaggg    300
gggaccaaac tggaaataaa acgggctgat gctgcaccaa ctgtatccat cttcccacta    360
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctatacct gtgaggccac tcacaagaca    600
tcaacttcac ccattgtcaa gagcttcaac aggaatgagt gttag                    645
```

<210> SEQ ID NO 138
<211> LENGTH: 214
<212> TYPE: PRT
<213> ORGANISM: Mus musculus

<400> SEQUENCE: 138

```
Asp Ile Gln Met Thr Gln Thr Thr Ser Ser Leu Ser Ala Ser Leu Gly
1               5                   10                  15

Asp Arg Val Ser Ile Ser Cys Arg Ala Ser Gln Asp Ile Ser Asn Tyr
            20                  25                  30

Leu Asn Trp Tyr Gln Gln Lys Pro Asp Gly Thr Phe Lys Leu Leu Ile
        35                  40                  45

Phe Tyr Thr Ser Arg Leu Leu Ser Gly Val Pro Ser Arg Phe Ser Gly
    50                  55                  60

Ser Gly Ser Gly Thr Asp Tyr Ser Leu Thr Ile Tyr Asn Leu Glu Gln
65                  70                  75                  80

Glu Asp Phe Ala Thr Tyr Phe Cys Gln Gln Gly Asp Thr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Leu Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 139
<211> LENGTH: 1344
<212> TYPE: DNA
<213> ORGANISM: Mus musculus

<400> SEQUENCE: 139

```
gaggtccaac tgcaacagtc tggacctgaa ctaatgaagc ctggggcttc agtgaagatg      60
tcctgcaagg cttctggata tacattcact gactacaaca tgcactgggt gaagcagaac     120
caaggaaaga ccctagaatg gataggagaa attaatccta acagtggtgg tgctggctac     180
aaccagaagt tcaagggcaa ggccacattg actgtagaca gtcctccac acagcctac      240
atggagctcc gcagcctgac atctgaggac tctgcagtct attactgtgc aagattgggc     300
tacgatgata tctacgacga ctggtacttc gatgtctggg gcgcagggac cacggtcacc     360
gtctcctcag ccaaaacgac accccatct gtctatccac tggcccctgg atctgctgcc      420
caaactaact ccatggtgac cctgggatgc ctggtcaagg ctatttccc tgagccagtg      480
acagtgacct ggaactctgg atccctgtcc agcggtgtgc acaccttccc agctgtcctg     540
cagtctgacc tctacactct gagcagctca gtgactgtcc cctccagcac ctggcccagc     600
gagaccgtca cctgcaacgt tgcccacccg gccagcagca ccaaggtgga caagaaaatt     660
gtgcccaggg attgtggttg taagccttgc atatgtacag tcccagaagt atcatctgtc     720
ttcatcttcc ccccaaagcc caaggatgtg ctcaccatta ctctgactcc taaggtcacg     780
tgtgttgtgg tagacatcag caaggatgat cccgaggtcc agttcagctg gtttgtagat     840
gatgtggagg tgcacacagc tcagacgcaa ccccgggagg agcagttcaa cagcactttc     900
cgctcagtca gtgaacttcc catcatgcac caggactggc tcaatggcaa ggagttcaaa     960
tgcagggtca acagtgcagc tttccctgcc cccatcgaga aaaccatctc caaaaccaaa    1020
ggcagaccga aggctccaca ggtgtacacc attccacctc caaggagca gatggccaag    1080
gataaagtca gtctgacctg catgataaca gacttcttcc ctgaagacat tactgtggag    1140
tggcagtgga atgggcagcc agcggagaac tacaagaaca ctcagcccat catggacaca    1200
gatggctctt acttcatcta cagcaagctc aatgtgcaga gagcaactg ggaggcagga    1260
aatactttca cctgctctgt gttacatgag ggcctgcaca accaccatac tgagaagagc    1320
ctctcccact ctcctggtaa atga                                           1344
```

<210> SEQ ID NO 140
<211> LENGTH: 447
<212> TYPE: PRT
<213> ORGANISM: Mus musculus

<400> SEQUENCE: 140

```
Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Val Lys Gln Asn Gly Lys Thr Leu Glu Trp Ile
        35                  40                  45

Gly Glu Ile Asn Pro Asn Ser Gly Gly Ala Gly Tyr Asn Gln Lys Phe
    50                  55                  60

Lys Gly Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
```

```
                    85                  90                  95
Ala Arg Leu Gly Tyr Asp Asp Ile Tyr Asp Asp Trp Tyr Phe Asp Val
                100                 105                 110

Trp Gly Ala Gly Thr Thr Val Thr Val Ser Ser Ala Lys Thr Thr Pro
            115                 120                 125

Pro Ser Val Tyr Pro Leu Ala Pro Gly Ser Ala Ala Gln Thr Asn Ser
        130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
        435                 440                 445

<210> SEQ ID NO 141
<211> LENGTH: 10
<212> TYPE: PRT
<213> ORGANISM: Artificial Sequence
<220> FEATURE:
<223> OTHER INFORMATION: Ab-11 and Ab-16 LCDR1

<400> SEQUENCE: 141

Arg Ala Ser Ser Ser Ile Ser Tyr Ile His
```

<210> SEQ ID NO 142
<211> LENGTH: 7
<212> TYPE: PRT
<213> ORGANISM: Artificial Sequence
<220> FEATURE:
<223> OTHER INFORMATION: Ab-11 and Ab-16 LCDR2

<400> SEQUENCE: 142

Ala Thr Ser Asn Leu Ala Ser
1               5

<210> SEQ ID NO 143
<211> LENGTH: 9
<212> TYPE: PRT
<213> ORGANISM: Artificial Sequence
<220> FEATURE:
<223> OTHER INFORMATION: Ab-11 and Ab-16 LCDR3

<400> SEQUENCE: 143

Gln Gln Trp Ser Ser Asp Pro Leu Thr
1               5

<210> SEQ ID NO 144
<211> LENGTH: 5
<212> TYPE: PRT
<213> ORGANISM: Artificial Sequence
<220> FEATURE:
<223> OTHER INFORMATION: Ab-11 and Ab-16 HCDR1

<400> SEQUENCE: 144

Asp Tyr Tyr Ile His
1               5

<210> SEQ ID NO 145
<211> LENGTH: 17
<212> TYPE: PRT
<213> ORGANISM: Artificial Sequence
<220> FEATURE:
<223> OTHER INFORMATION: Ab-11 and Ab-16 HCDR2

<400> SEQUENCE: 145

Arg Val Asp Pro Asp Asn Gly Glu Thr Glu Phe Ala Pro Lys Phe Pro
1               5                   10                  15

Gly

<210> SEQ ID NO 146
<211> LENGTH: 12
<212> TYPE: PRT
<213> ORGANISM: Artificial Sequence
<220> FEATURE:
<223> OTHER INFORMATION: Ab-11 and Ab-16 HCDR3

<400> SEQUENCE: 146

Glu Asp Tyr Asp Gly Thr Tyr Thr Trp Phe Pro Tyr
1               5                   10

<210> SEQ ID NO 147
<211> LENGTH: 642
<212> TYPE: DNA
<213> ORGANISM: Mus musculus

<400> SEQUENCE: 147
caaattgttc tctcccagtc tccagcattc ctgtctgtat ctccagggga taaggtcaca    60

```
atgacttgca gggccagctc aagtataagt tacatacact ggtttcagca gaagccagga    120
tcctccccca gatcctggat ttatgccaca tccaacctgg cttctggagt ccctggtcgc    180
ttcagtggca gtgggtctgg gacctcttac tctctcacaa tcagcagagt ggaggctgag    240
gatgctgcca cttattactg ccagcagtgg agtagtgacc cactcacgtt cggtgctggg    300
accaagctgg agctgaaacg gctgatgct gcaccaactg tatccatctt cccaccatcc    360
agtgagcagt taacatctgg aggtgcctca gtcgtgtgct tcttgaacaa cttctacccc    420
aaagacatca atgtcaagtg gaagattgat ggcagtgaac gacaaaatgg cgtcctgaac    480
agttggactg atcaggacag caaagacagc acctacagca tgagcagcac cctcacgttg    540
accaaggacg agtatgaacg acataacagc tatacctgtg aggccactca caagacatca    600
acttcaccca ttgtcaagag cttcaacagg aatgagtgtt ag                        642
```

```
<210> SEQ ID NO 148
<211> LENGTH: 213
<212> TYPE: PRT
<213> ORGANISM: Mus musculus

<400> SEQUENCE: 148
```

```
Gln Ile Val Leu Ser Gln Ser Pro Ala Phe Leu Ser Val Ser Pro Gly
1               5                   10                  15

Asp Lys Val Thr Met Thr Cys Arg Ala Ser Ser Ser Ile Ser Tyr Ile
            20                  25                  30

His Trp Phe Gln Gln Lys Pro Gly Ser Ser Pro Arg Ser Trp Ile Tyr
        35                  40                  45

Ala Thr Ser Asn Leu Ala Ser Gly Val Pro Gly Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asp Pro Leu Thr
                85                  90                  95

Phe Gly Ala Gly Thr Lys Leu Glu Leu Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210
```

```
<210> SEQ ID NO 149
<211> LENGTH: 1338
<212> TYPE: DNA
<213> ORGANISM: Mus musculus

<400> SEQUENCE: 149
gaagttcagc tgcaacagtc tggggcagac cttgtgcagc caggggcctc agtcaaggtg    60
```

```
tcctgcacag cttctggctt cgacattaag gactactata tacactggat gaaacagagg    120
cctgaccagg gcctggagtg gattggaagg gttgatcctg acaatggtga gactgaattt    180
gccccgaagt tcccgggcaa ggccactttt acaacagaca catcctccaa cacagcctac    240
ctacaactca gaggcctgac atctgaggac actgccatct attactgtgg gagagaagac    300
tacgatggta cctacacctg gtttccttat tggggccaag ggactctggt cactgtctct    360
gcagccaaaa cgacaccccc atctgtctat ccactggccc ctggatctgc tgcccaaact    420
aactccatgg tgaccctggg atgcctggtc aagggctatt tccctgagcc agtgacagtg    480
acctggaact ctggatccct gtccagcggt gtgcacacct tcccagctgt cctgcagtct    540
gacctctaca ctctgagcag ctcagtgact gtcccctcca gcacctggcc cagcgagacc    600
gtcacctgca acgttgccca cccggccagc agcaccaagg tggacaagaa aattgtgccc    660
agggattgtg gttgtaagcc ttgcatatgt acagtcccag aagtatcatc tgtcttcatc    720
ttccccccaa agcccaagga tgtgctcacc attactctga ctcctaaggt cacgtgtgtt    780
gtggtagaca tcagcaagga tgatcccgag gtccagttca gctggtttgt agatgatgtg    840
gaggtgcaca cagctcagac gcaaccccgg gaggagcagt tcaacagcac tttccgctca    900
gtcagtgaac ttcccatcat gcaccaggac tggctcaatg caaggagtt caaatgcagg    960 gtcaacagtg cagctttccc tgcccccatc gagaaaacca tctccaaaac caaaggcaga   1020
ccgaaggctc cacaggtgta caccattcca cctcccaagg agcagatggc caaggataaa   1080
gtcagtctga cctgcatgat aacagacttc ttccctgaag acattactgt ggagtggcag   1140
tggaatgggc agccagcgga gaactacaag aacactcagc ccatcatgga cacagatggc   1200
tcttacttca tctacagcaa gctcaatgtg cagaagagca ctgggaggc aggaaatact   1260 ttcacctgct ctgtgttaca tgagggcctg cacaaccacc atactgagaa gagcctctcc   1320
cactctcctg gtaaatga                                                 1338
```

<210> SEQ ID NO 150
<211> LENGTH: 445
<212> TYPE: PRT
<213> ORGANISM: Mus musculus

<400> SEQUENCE: 150

Glu Val Gln Leu Gln Gln Ser Gly Ala Asp Leu Val Gln Pro Gly Ala
1               5                   10                  15

Ser Val Lys Val Ser Cys Thr Ala Ser Gly Phe Asp Ile Lys Asp Tyr
            20                  25                  30

Tyr Ile His Trp Met Lys Gln Arg Pro Asp Gln Gly Leu Glu Trp Ile
        35                  40                  45

Gly Arg Val Asp Pro Asp Asn Gly Glu Thr Glu Phe Ala Pro Lys Phe
    50                  55                  60

Pro Gly Lys Ala Thr Phe Thr Thr Asp Thr Ser Ser Asn Thr Ala Tyr
65                  70                  75                  80

Leu Gln Leu Arg Gly Leu Thr Ser Glu Asp Thr Ala Ile Tyr Tyr Cys
                85                  90                  95

Gly Arg Glu Asp Tyr Asp Gly Thr Tyr Thr Trp Phe Pro Tyr Trp Gly
            100                 105                 110

Gln Gly Thr Leu Val Thr Val Ser Ala Ala Lys Thr Thr Pro Pro Ser
        115                 120                 125

Val Tyr Pro Leu Ala Pro Gly Ser Ala Ala Gln Thr Asn Ser Met Val
    130                 135                 140

```
Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
            165                 170                 175

Val Leu Gln Ser Asp Leu Tyr Thr Leu Ser Ser Val Thr Val Pro
        180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
370                 375                 380

Pro Ala Glu Asn Tyr Lys Asn Thr Gln Pro Ile Met Asp Thr Asp Gly
385                 390                 395                 400

Ser Tyr Phe Ile Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445

<210> SEQ ID NO 151
<211> LENGTH: 318
<212> TYPE: DNA
<213> ORGANISM: Mus musculus

<400> SEQUENCE: 151
gacatccagt tgacccagtc tccatccttc ctgtctgcat ctgtaggaga cagagtcacc      60
atcacttgca gggccagctc aagtataagt tacatacact ggtatcagca aaaaccaggg    120
aaagccccta agctcctgat ctatgccaca tccaacctgg cttctgggtc ccatcaagg      180 ttcagcggca gtggatctgg gacagaattc actctcacaa tcagcagcct gcagcctgaa    240
gattttgcaa cttattactg tcagcagtgg agtagtgacc cactcacgtt cggcggaggg    300
accaaggtgg agatcaaa                                                  318
```

<210> SEQ ID NO 152
<211> LENGTH: 106
<212> TYPE: PRT
<213> ORGANISM: Mus musculus

<400> SEQUENCE: 152

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ile Ser Tyr Ile
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asp Pro Leu Thr
                85                  90                  95

Phe Gly Gly Gly Thr Lys Val Glu Ile Lys
            100                 105

<210> SEQ ID NO 153
<211> LENGTH: 363
<212> TYPE: DNA
<213> ORGANISM: Mus musculus

<400> SEQUENCE: 153
gaggtgcagc tggtgcagtc tggggctgag gtgaagaagc ctggggcctc agtgaaggtc      60
tcctgcaagg cttctggatt cgacattaag gactactata tacactgggt gcgacaggcc    120
cctggacaag gcttgagtg gatcggaagg gttgatcctg acaatggtga gactgaattt     180
gccccgaagt tcccgggcaa ggtcaccatg accacagaca cgtccatcag cacagcctac    240
atggagctga gcaggctgag atctgacgac acggccgtgt attactgtgc gagagaagac    300
tacgatggta cctacaccct gttttcctta tgggggccaag ggactctggt caccgtctct    360
agt                                                                   363

<210> SEQ ID NO 154
<211> LENGTH: 121
<212> TYPE: PRT
<213> ORGANISM: Mus musculus

<400> SEQUENCE: 154

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Lys Asp Tyr
            20                  25                  30

Tyr Ile His Trp Val Arg Gln Ala Pro Gly Gln Gly Leu Glu Trp Ile
        35                  40                  45

Gly Arg Val Asp Pro Asp Asn Gly Glu Thr Glu Phe Ala Pro Lys Phe
    50                  55                  60

Pro Gly Lys Val Thr Met Thr Thr Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Asp Tyr Asp Gly Thr Tyr Thr Trp Phe Pro Tyr Trp Gly
            100                 105                 110

Gln Gly Thr Leu Val Thr Val Ser Ser
        115                 120

<210> SEQ ID NO 155
<211> LENGTH: 639
<212> TYPE: DNA
<213> ORGANISM: Artificial Sequence
<220> FEATURE:
<223> OTHER INFORMATION: Humanized antibody sequence

<400> SEQUENCE: 155

```
gacatccagt tgacccagtc tccatccttc ctgtctgcat ctgtaggaga cagagtcacc    60
atcacttgca gggccagctc aagtataagt tacatacact ggtatcagca aaaaccaggg   120
aaagccccta agctcctgat ctatgccaca tccaacctgg cttctggggt cccatcaagg   180
ttcagcggca gtggatctgg gacagaattc actctcacaa tcagcagcct gcagcctgaa   240
gattttgcaa cttattactg tcagcagtgg agtagtgacc cactcacgtt cggcggaggg   300
accaaggtgg agatcaaacg tacggtggct gcaccatctg tcttcatctt cccgccatct   360
gatgagcagt tgaaatctgg aactgcctct gttgtgtgcc tgctgaataa cttctatccc   420
agagaggcca agtacagtg gaaggtggat aacgccctcc aatcgggtaa ctcccaggag   480
agtgtcacag agcaggacag caaggacagc acctacagcc tcagcagcac cctgacgctg   540
agcaaagcag actacgagaa acacaaagtc tacgcctgcg aagtcaccca tcagggcctg   600
agctcgcccg tcacaaagag cttcaacagg ggagagtgt                         639
```

<210> SEQ ID NO 156
<211> LENGTH: 213
<212> TYPE: PRT
<213> ORGANISM: Artificial Sequence
<220> FEATURE:
<223> OTHER INFORMATION: Humanized antibody sequence

<400> SEQUENCE: 156

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Ile Ser Tyr Ile
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asp Pro Leu Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala 180                 185                 190
Cys Glu Val Thr His Gln Gly Leu Ser Ser Pro Val Thr Lys Ser Phe
        195                 200                 205

Asn Arg Gly Glu Cys
    210

<210> SEQ ID NO 157
<211> LENGTH: 1341
<212> TYPE: DNA
<213> ORGANISM: Artificial Sequence
<220> FEATURE:
<223> OTHER INFORMATION: Humanized antibody sequence

<400> SEQUENCE: 157

| | | | | | |
|---|---|---|---|---|---|
| gaggtgcagc | tggtgcagtc | tggggctgag | gtgaagaagc | ctggggcctc | agtgaaggtc | 60 |
| tcctgcaagg | cttctggatt | cgacattaag | gactactata | tacactgggt | gcgacaggcc | 120 |
| cctggacaag | gcttgagtg | gatcggaagg | gttgatcctg | acaatggtga | gactgaattt | 180 |
| gccccgaagt | tcccgggcaa | ggtcaccatg | accacagaca | cgtccatcag | cacagcctac | 240 |
| atggagctga | gcaggctgag | atctgacgac | acggccgtgt | attactgtgc | gagagaagac | 300 |
| tacgatggta | cctacacctg | gtttccttat | tggggccaag | ggactctggt | caccgtctct | 360 |
| agtgcctcca | ccaagggccc | atcggtcttc | cccctggcgc | cctgctccag | gagcacctcc | 420 |
| gagagcacag | cggccctggg | ctgcctggtc | aaggactact | tccccgaacc | ggtgacggtg | 480 |
| tcgtggaact | caggcgctct | gaccagcggc | gtgcacacct | tcccagctgt | cctacagtcc | 540 |
| tcaggactct | actccctcag | cagcgtggtg | accgtgccct | ccagcaactt | cggcacccag | 600 |
| acctacacct | gcaacgtaga | tcacaagccc | agcaacacca | aggtggacaa | gacagttgag | 660 |
| cgcaaatgtt | gtgtcgagtg | cccaccgtgc | ccagcaccac | ctgtggcagg | accgtcagtc | 720 |
| ttcctcttcc | ccccaaaacc | caaggacacc | ctcatgatct | cccggacccc | tgaggtcacg | 780 |
| tgcgtggtgg | tggacgtgag | ccacgaagac | cccgaggtcc | agttcaactg | gtacgtggac | 840 |
| ggcgtggagg | tgcataatgc | caagacaaag | ccacgggagg | agcagttcaa | cagcacgttc | 900 |
| cgtgtggtca | gcgtcctcac | cgttgtgcac | caggactggc | tgaacggcaa | ggagtacaag | 960 |
| tgcaaggtct | ccaacaaagg | cctcccagcc | cccatcgaga | aaaccatctc | caaaaccaaa | 1020 |
| gggcagcccc | gagaaccaca | ggtgtacacc | ctgcccccat | cccgggagga | gatgaccaag | 1080 |
| aaccaggtca | gcctgacctg | cctggtcaaa | ggcttctacc | ccagcgacat | cgccgtggag | 1140 |
| tgggagagca | atgggcagcc | ggagaacaac | tacaagacca | cacctcccat | gctggactcc | 1200 |
| gacggctcct | tcttcctcta | cagcaagctc | accgtggaca | agagcaggtg | gcagcagggg | 1260 |
| aacgtcttct | catgctccgt | gatgcatgag | gctctgcaca | accactacac | gcagaagagc | 1320 |
| ctctccctgt | ctccgggtaa | a | | | | 1341 |

<210> SEQ ID NO 158
<211> LENGTH: 447
<212> TYPE: PRT
<213> ORGANISM: Artificial Sequence
<220> FEATURE:
<223> OTHER INFORMATION: Humanized antibody sequence

<400> SEQUENCE: 158

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Lys Asp Tyr
            20                  25                  30

```
Tyr Ile His Trp Val Arg Gln Ala Pro Gly Gln Gly Leu Glu Trp Ile
        35                  40                  45
Gly Arg Val Asp Pro Asp Asn Gly Glu Thr Glu Phe Ala Pro Lys Phe
    50                  55                  60
Pro Gly Lys Val Thr Met Thr Thr Asp Thr Ser Ile Ser Thr Ala Tyr
65                  70                  75                  80
Met Glu Leu Ser Arg Leu Arg Ser Asp Thr Ala Val Tyr Tyr Cys
                85                  90                  95
Ala Arg Glu Asp Tyr Asp Gly Thr Tyr Thr Trp Phe Pro Tyr Trp Gly
            100                 105                 110
Gln Gly Thr Leu Val Thr Val Ser Ser Ala Ser Thr Lys Gly Pro Ser
            115                 120                 125
Val Phe Pro Leu Ala Pro Cys Ser Arg Ser Thr Ser Glu Ser Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Asn Phe Gly Thr Gln Thr Tyr Thr Cys Asn Val Asp His
            195                 200                 205
Lys Pro Ser Asn Thr Lys Val Asp Lys Thr Val Glu Arg Lys Cys Cys
        210                 215                 220
Val Glu Cys Pro Pro Cys Pro Ala Pro Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Phe Arg Val Val Ser
        290                 295                 300
Val Leu Thr Val Val His Gln Asp Trp Leu Asn Gly Lys Glu Tyr Lys
305                 310                 315                 320
Cys Lys Val Ser Asn Lys Gly Leu Pro Ala Pro Ile Glu Lys Thr Ile
                325                 330                 335
Ser Lys Thr Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
            355                 360                 365
Val Lys Gly Phe Tyr Pro Ser Asp Ile Ala Val Glu Trp Glu Ser Asn
        370                 375                 380
Gly Gln Pro Glu Asn Asn Tyr Lys Thr Thr Pro Met Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
            435                 440                 445
```

<210> SEQ ID NO 159
<211> LENGTH: 11
<212> TYPE: PRT
<213> ORGANISM: Artificial Sequence
<220> FEATURE:
<223> OTHER INFORMATION: Ab-12 LCDR1

<400> SEQUENCE: 159

Arg Ala Ser Gln Asp Ile Ser Asn Tyr Leu Asn
1               5                   10

<210> SEQ ID NO 160
<211> LENGTH: 7
<212> TYPE: PRT
<213> ORGANISM: Artificial Sequence
<220> FEATURE:
<223> OTHER INFORMATION: Ab-12 LCDR2

<400> SEQUENCE: 160

Tyr Thr Ser Thr Leu Gln Ser
1               5

<210> SEQ ID NO 161
<211> LENGTH: 9
<212> TYPE: PRT
<213> ORGANISM: Artificial Sequence
<220> FEATURE:
<223> OTHER INFORMATION: Ab-12 LCDR3

<400> SEQUENCE: 161

Gln Gln Gly Asp Thr Leu Pro Tyr Thr
1               5

<210> SEQ ID NO 162
<211> LENGTH: 5
<212> TYPE: PRT
<213> ORGANISM: Artificial Sequence
<220> FEATURE:
<223> OTHER INFORMATION: Ab-12 HCDR1

<400> SEQUENCE: 162

Asp Tyr Asn Met His
1               5

<210> SEQ ID NO 163
<211> LENGTH: 17
<212> TYPE: PRT
<213> ORGANISM: Artificial Sequence
<220> FEATURE:
<223> OTHER INFORMATION: Ab-12 HCDR2

<400> SEQUENCE: 163

Glu Ile Asn Pro Asn Ser Gly Gly Ser Gly Tyr Asn Gln Lys Phe Lys
1               5                   10                  15

Gly

<210> SEQ ID NO 164
<211> LENGTH: 14
<212> TYPE: PRT
<213> ORGANISM: Artificial Sequence
<220> FEATURE:
<223> OTHER INFORMATION: Ab-12 HCDR3

<400> SEQUENCE: 164

Leu Gly Tyr Tyr Gly Asn Tyr Glu Asp Trp Tyr Phe Asp Val
1               5                   10

<210> SEQ ID NO 165
<211> LENGTH: 645
<212> TYPE: DNA
<213> ORGANISM: Mus musculus

<400> SEQUENCE: 165

```
gatctccaga tgacacagac tacttcctcc ctgtctgcct ctctgggaga cagagtcacc      60
atcagttgca gggcaagtca ggacattagc aattatttaa actggtatca gcagaaacca     120
gatggaactg ttaagctcct gatcttctac acatcaacat tacagtcagg agtcccatcg     180
aggttcagtg gcagtgggtc tggaacaaat tattctctca ccattaccaa cctggagcaa     240
gatgatgctg ccacttactt ttgccaacag ggtgatacgc ttccgtacac gttcggaggg     300
gggaccaagc tggaaataaa acgggctgat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag caccctcacg     540
ttgaccaagg acgagtatga acgacataac agctatacct gtgaggccac tcacaagaca     600
tcaacttcac ccattgtcaa gagcttcaac aggaatgagt gttag                      645
```

<210> SEQ ID NO 166
<211> LENGTH: 214
<212> TYPE: PRT
<213> ORGANISM: Mus musculus

<400> SEQUENCE: 166

Asp Leu Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Phe Tyr Thr Ser Thr Leu Gln Ser Gly Val Pro Ser Arg Phe Ser Gly
    50                  55                  60

Ser Gly Ser Gly Thr Asn Tyr Ser Leu Thr Ile Thr Asn Leu Glu Gln
65                  70                  75                  80

Asp Asp Ala Ala Thr Tyr Phe Cys Gln Gln Gly Asp Thr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 167
<211> LENGTH: 1344
<212> TYPE: DNA
<213> ORGANISM: Mus musculus

<400> SEQUENCE: 167

```
gaggtccagt tgcaacagtc tggacctgaa ctaatgaagc ctggggcttc agtgaagatg        60
tcctgcaagg cttctggata cacattcact gactacaaca tgcactggat gaagcagaac       120
caaggaaaga gcctagagtg gataggagag attaatccta acagtggtgg ttctggttac       180
aaccagaagt tcaaaggcaa ggccacattg actgtagaca agtcctccag cacagcctac       240
atggagctcc gcagcctgac atctgaggac tctgcagtct attactgtgc aagattgggc       300
tactatggta actacgagga ctggtatttc gatgtctggg gcgcagggac cacggtcacc       360
gtctcctctg ccaaaacgac ccccccatct gtctatccac tggcccctgg atctgctgcc       420
caaactaact ccatggtgac cctgggatgc ctggtcaagg ctatttccc tgagccagtg        480 acagtgacct ggaactctgg atccctgtcc agcggtgtgc acaccttccc agctgtcctg       540
cagtctgacc tctacactct gagcagctca gtgactgtcc cctccagcac ctggcccagc       600
gagaccgtca cctgcaacgt tgcccacccg ccagcagca ccaaggtgga caagaaaatt       660
gtgcccaggg attgtggttg taagccttgc atatgtacag tcccagaagt atcatctgtc       720
ttcatcttcc ccccaaagcc caaggatgtg ctcaccatta ctctgactcc taaggtcacg       780
tgtgttgtgg tagacatcag caaggatgat cccgaggtcc agttcagctg gtttgtagat       840
gatgtggagg tgcacacagc tcagacgcaa ccccgggagg agcagttcaa cagcactttc       900
cgctcagtca gtgaacttcc catcatgcac caggactggc tcaatggcaa ggagttcaaa       960
tgcagggtca acagtgcagc tttccctgcc cccatcgaga aaaccatctc caaaaccaaa      1020
ggcagaccga aggctccaca ggtgtacacc attccacctc caaggagca gatggccaag      1080 gataaagtca gtctgacctg catgataaca gacttcttcc ctgaagacat tactgtggag      1140
tggcagtgga atgggcagcc agcggagaac tacaagaaca ctcagcccat catggacaca      1200
gatggctctt acttcatcta cagcaagctc aatgtgcaga agagcaactg ggaggcagga      1260
aatactttca cctgctctgt gttacatgag ggcctgcaca accaccatac tgagaagagc      1320
ctctcccact ctcctggtaa atga                                             1344
```

<210> SEQ ID NO 168
<211> LENGTH: 447
<212> TYPE: PRT
<213> ORGANISM: Mus musculus

<400> SEQUENCE: 168

```
Glu Val Gln Leu Gln Gln Ser Gly Pro Glu Leu Met Lys Pro Gly Ala
1               5                   10                  15

Ser Val Lys Met Ser Cys Lys Ala Ser Gly Tyr Thr Phe Thr Asp Tyr
            20                  25                  30

Asn Met His Trp Met Lys Gln Asn Gln Gly Lys Ser Leu Glu Trp Ile
        35                  40                  45

Gly Glu Ile Asn Pro Asn Ser Gly Gly Ser Gly Tyr Asn Gln Lys Phe
    50                  55                  60

Lys Gly Lys Ala Thr Leu Thr Val Asp Lys Ser Ser Ser Thr Ala Tyr
65                  70                  75                  80
```

```
Met Glu Leu Arg Ser Leu Thr Ser Glu Asp Ser Ala Val Tyr Tyr Cys
                85                  90                  95

Ala Arg Leu Gly Tyr Tyr Gly Asn Tyr Glu Asp Trp Tyr Phe Asp Val
            100                 105                 110

Trp Gly Ala Gly Thr Thr Val Thr Val Ser Ser Ala Lys Thr Thr Pro
        115                 120                 125

Pro Ser Val Tyr Pro Leu Ala Pro Gly Ser Ala Ala Gln Thr Asn Ser
    130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Pro Ser Ser Thr Trp Pro Ser Glu Thr Val Thr Cys Asn Val Ala
        195                 200                 205

His Pro Ala Ser Ser Thr Lys Val Asp Lys Lys Ile Val Pro Arg Asp
    210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Ile Tyr Ser Lys Leu Asn Val Gln Lys Ser Asn
                405                 410                 415

Trp Glu Ala Gly Asn Thr Phe Thr Cys Ser Val Leu His Glu Gly Leu
            420                 425                 430

His Asn His His Thr Glu Lys Ser Leu Ser His Ser Pro Gly Lys
    435                 440                 445

<210> SEQ ID NO 169
<211> LENGTH: 12
<212> TYPE: PRT
<213> ORGANISM: Artificial Sequence
<220> FEATURE:
<223> OTHER INFORMATION: Ab-13 and Ab-14 LCDR1

<400> SEQUENCE: 169
```

```
Arg Ala Ser Ser Ser Val Thr Ser Ser Tyr Leu Asn
1               5                   10
```

<210> SEQ ID NO 170
<211> LENGTH: 7
<212> TYPE: PRT
<213> ORGANISM: Artificial Sequence
<220> FEATURE:
<223> OTHER INFORMATION: Ab-13 and Ab-14 LCDR2

<400> SEQUENCE: 170

```
Ser Thr Ser Asn Leu Ala Ser
1               5
```

<210> SEQ ID NO 171
<211> LENGTH: 9
<212> TYPE: PRT
<213> ORGANISM: Artificial Sequence
<220> FEATURE:
<223> OTHER INFORMATION: Ab-13 and Ab-14 LCDR3

<400> SEQUENCE: 171

```
Gln Gln Tyr Asp Phe Phe Pro Ser Thr
1               5
```

<210> SEQ ID NO 172
<211> LENGTH: 5
<212> TYPE: PRT
<213> ORGANISM: Artificial Sequence
<220> FEATURE:
<223> OTHER INFORMATION: Ab-13 and Ab-14 HCDR1

<400> SEQUENCE: 172

```
Asp Tyr Tyr Met Asn
1               5
```

<210> SEQ ID NO 173
<211> LENGTH: 17
<212> TYPE: PRT
<213> ORGANISM: Artificial Sequence
<220> FEATURE:
<223> OTHER INFORMATION: Ab-13 and Ab-14 HCDR2

<400> SEQUENCE: 173

```
Asp Ile Asn Pro Tyr Asn Asp Asp Thr Thr Tyr Asn His Lys Phe Lys
1               5                   10                  15

Gly
```

<210> SEQ ID NO 174
<211> LENGTH: 11
<212> TYPE: PRT
<213> ORGANISM: Artificial Sequence
<220> FEATURE:
<223> OTHER INFORMATION: Ab-13 and Ab-14 HCDR3

<400> SEQUENCE: 174

```
Glu Thr Ala Val Ile Thr Thr Asn Ala Met Asp
1               5                   10
```

<210> SEQ ID NO 175
<211> LENGTH: 645
<212> TYPE: DNA
<213> ORGANISM: Mus musculus

<400> SEQUENCE: 175

```
cagattgttc tcacccagtc tccagcaatc atgtctgcat ctccagggga gaaggtcacc    60
```

```
atgacctgca gggccagctc aagtgtaact tccagttact tgaactggta ccagcagaag    120
ccaggatctt cccccaaact ctggatttat agcacatcca acctggcttc aggagtccca    180
gctcgcttca gtggcagtgg gtctgggacc tcttactctc tcacaatcag cagtgtggag    240
gctgaggatg ctgccactta ttactgccag cagtatgatt ttttcccatc gacgttcggt    300
ggaggcacca agctggaaat caagcgggct gatgctgcac caactgtatc catcttccca    360
ccatccagtg agcagttaac atctggaggt gcctcagtcg tgtgcttctt gaacaacttc    420 tacccccaaag acatcaatgt caagtggaag attgatggca gtgaacgaca aaatggcgtc    480
ctgaacagtt ggactgatca ggacagcaaa gacagcacct acagcatgag cagcaccctc    540
acgttgacca aggacgagta tgaacgacat aacagctata cctgtgaggc cactcacaag    600
acatcaactt cacccatcgt caagagcttc aacaggaatg agtgt                    645
```

<210> SEQ ID NO 176
<211> LENGTH: 215
<212> TYPE: PRT
<213> ORGANISM: Mus musculus
<400> SEQUENCE: 176

```
Gln Ile Val Leu Thr Gln Ser Pro Ala Ile Met Ser Ala Ser Pro Gly
  1               5                  10                  15

Glu Lys Val Thr Met Thr Cys Arg Ala Ser Ser Val Thr Ser Ser
             20                  25                  30

Tyr Leu Asn Trp Tyr Gln Gln Lys Pro Gly Ser Ser Pro Lys Leu Trp
         35                  40                  45

Ile Tyr Ser Thr Ser Asn Leu Ala Ser Gly Val Pro Ala Arg Phe Ser
     50                  55                  60

Gly Ser Gly Ser Gly Thr Ser Tyr Ser Leu Thr Ile Ser Ser Val Glu
 65                  70                  75                  80

Ala Glu Asp Ala Ala Thr Tyr Tyr Cys Gln Gln Tyr Asp Phe Phe Pro
                 85                  90                  95

Ser Thr Phe Gly Gly Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Ser Glu Arg Gln Asn Gly Val
145                 150                 155                 160

Leu Asn Ser Trp Thr Asp Gln Asp Ser Lys Asp Ser Thr Tyr Ser Met
                165                 170                 175

Ser Ser Thr Leu Thr Leu Thr Lys Asp Glu Tyr Glu Arg His Asn Ser
            180                 185                 190

Tyr Thr Cys Glu Ala Thr His Lys Thr Ser Thr Ser Pro Ile Val Lys
        195                 200                 205

Ser Phe Asn Arg Asn Glu Cys
    210                 215
```

<210> SEQ ID NO 177
<211> LENGTH: 1335
<212> TYPE: DNA
<213> ORGANISM: Mus musculus
<400> SEQUENCE: 177

```
gaggtccagc tgcaacaatc tggacctgag ctggtgaagc ctggggcttc agtgaagatg     60
tcctgtaagg cttctggata cacattcact gactactaca tgaactgggt gaagcagagc    120
catggagaga gccttgagtg gattggagat attaatcctt acaacgatga ctacctac     180
aaccacaagt tcaagggcaa ggccacattg actgtagaca atcctccaa cacagcctac     240
atgcagctca acagcctgac atctgaggac tctgcagtct attactgtgc aagagagacg    300
gccgttatta ctacgaatgc tatggactac tggggtcaag aacctcagt caccgtctcc     360
tcagccaaaa cgacaccccc atctgtctat ccactggccc ctggatctgc tgcccaaact    420
aactccatgg tgaccctggg atgcctggtc aagggctatt ccctgagcc agtgacagtg     480
acctggaact ctggatccct gtccagcggt gtgcacacct cccagctgt cctgcagtct     540
gacctctaca ctctgagcag ctcagtgact gtccccctcca gcacctggcc cagcgagacc    600
gtcacctgca acgttgccca cccggccagc agcaccaagg tggacaagaa aattgtgccc    660
agggattgtg gttgtaagcc ttgcatatgt acagtcccag aagtatcatc tgtcttcatc    720
ttccccccaa agcccaagga tgtgctcacc attactctga ctcctaaggt cacgtgtgtt    780
gtggtagaca tcagcaagga tgatcccgag gtccagttca gctggtttgt agatgatgtg    840
gaggtgcaca cagctcagac gcaaccccgg gaggagcagt tcaacagcac tttccgctca    900
gtcagtgaac ttcccatcat gcaccaggac tggctcaatg gcaaggagtt caaatgcagg    960
gtcaacagtg cagcttttcc tgcccccatc gagaaaacca tctccaaaac caaaggcaga   1020
ccgaaggctc cacaggtgta caccattcca cctcccaagg agcagatggc aaggataaa    1080
gtcagtctga cctgcatgat aacagacttc ttccctgaag acattactgt ggagtggcag   1140
tggaatgggc agccagcgga gaactacaag aacactcagc ccatcatgga cacagatggc   1200
tcttacttca tctacagcaa gctcaatgtg cagaagagca ctgggaggc aggaaatact   1260
ttcacctgct ctgtgttaca tgagggcctg cacaaccacc atactgagaa gagcctctcc   1320
cactctcctg gtaaa                                                    1335
```

<210> SEQ ID NO 178
<211> LENGTH: 445
<212> TYPE: PRT
<213> ORGANISM: Mus musculus

<400> SEQUENCE: 178

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Glu Ser Leu Glu Trp Ile
        35                  40                  45

Gly Asp Ile Asn Pro Tyr Asn Asp Asp Thr Thr Tyr Asn His Lys Phe
    50                  55                  60

Lys Gly Lys Ala Thr Leu Thr Val Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Glu Thr Ala Val Ile Thr Thr Asn Ala Met Asp Tyr Trp Gly
            100                 105                 110

Gln Gly Thr Ser Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
```

```
                  130                 135                 140
Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Cys Gly
210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
370                 375                 380

Pro Ala Glu Asn Tyr Lys Asn Thr Gln Pro Ile Met Asp Thr Asp Gly
385                 390                 395                 400

Ser Tyr Phe Ile Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
        435                 440                 445

<210> SEQ ID NO 179
<211> LENGTH: 324
<212> TYPE: DNA
<213> ORGANISM: Mus musculus

<400> SEQUENCE: 179
gacatccagc tgacccagag ccccagcttc ctttccgcat ccgttggtga ccgagtaaca      60
atcacatgcc gcgcctcatc ttcagttaca tcttcttatc ttaattggta tcaacaaaaa     120
ccaggaaaag cacctaaaact tcttatatac tctacatcta atctcgcatc aggagttccc    180
tctcgatttt caggatctgg atcaggcaca gaatttacac ttactatatc atcactccaa     240
ccagaagact cgccacttta ttactgccaa caatacgatt ttttttccaag cacattcgga   300 ggaggtacaa aagtagaaat caag                                            324
```

<210> SEQ ID NO 180
<211> LENGTH: 108
<212> TYPE: PRT
<213> ORGANISM: Mus musculus

<400> SEQUENCE: 180

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Val Thr Ser Ser
            20                  25                  30

Tyr Leu Asn Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Gln Gln Tyr Asp Phe Pro
                85                  90                  95

Ser Thr Phe Gly Gly Gly Thr Lys Val Glu Ile Lys
            100                 105

<210> SEQ ID NO 181
<211> LENGTH: 363
<212> TYPE: DNA
<213> ORGANISM: Mus musculus

<400> SEQUENCE: 181
gaggtgcagc tggtgcagag cggcgccgag gtcaagaaac ctggagcaag cgtaaaggtt      60
agttgcaaag catctggata cacatttacc gactactaca tgaattgggt acgacaagcc    120
cctggacaaa gacttgaatg gatgggagac attaaccctt ataacgacga cactacatac    180
aatcataaat ttaaaggaag agttacaatt acaagagata catccgcatc aaccgcctat    240
atggaacttt cctcattgag atctgaagac actgctgttt attactgtgc aagagaaact    300
gccgttatta ctactaacgc tatggattac tggggtcaag gaaccactgt taccgtctct    360
agt                                                                  363

<210> SEQ ID NO 182
<211> LENGTH: 121
<212> TYPE: PRT
<213> ORGANISM: Mus musculus

<400> SEQUENCE: 182

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Arg Leu Glu Trp Met
        35                  40                  45

Gly Asp Ile Asn Pro Tyr Asn Asp Asp Thr Thr Tyr Asn His Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Thr Ala Val Ile Thr Thr Asn Ala Met Asp Tyr Trp Gly
            100                 105                 110

Gln Gly Thr Thr Val Thr Val Ser Ser
        115                 120

<210> SEQ ID NO 183
<211> LENGTH: 363
<212> TYPE: DNA
<213> ORGANISM: Artificial Sequence
<220> FEATURE:
<223> OTHER INFORMATION: Humanized antibody sequence

<400> SEQUENCE: 183

```
gaggtgcagc tggtgcagag cggcgccgag gtcaagaaac ctggagcaag cgtaaaggtt      60
agttgcaaag catctggata cacatttacc gactactaca tgaattgggt acgacaagcc     120
cctggacaaa gacttgaatg gatgggagac attaaccctt ataacgacga cactacatac     180
aatcataaat ttaaaggaag agttacaatt acaagagata catccgcatc aaccgcctat     240
atggaacttt cctcattgag atctgaagac actgctgttt attactgtgc aagagaaact     300
gccgttatta ctactaacgc tatggattac tggggtcaag gaaccactgt taccgtctct     360
agt                                                                   363
```

<210> SEQ ID NO 184
<211> LENGTH: 215
<212> TYPE: PRT
<213> ORGANISM: Artificial Sequence
<220> FEATURE:
<223> OTHER INFORMATION: Humanized antibody sequence

<400> SEQUENCE: 184

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Thr Ser Ser
            20                  25                  30

Tyr Leu Asn Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Gln Gln Tyr Asp Phe Phe Pro
                85                  90                  95

Ser Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 185
<211> LENGTH: 1341
<212> TYPE: DNA
<213> ORGANISM: Artificial Sequence
<220> FEATURE:
<223> OTHER INFORMATION: Humanized antibody sequence

<400> SEQUENCE: 185

```
gaggtgcagc tggtgcagag cggcgccgag gtcaagaaac ctggagcaag cgtaaaggtt      60
agttgcaaag catctggata cacatttacc gactactaca tgaattgggt acgacaagcc     120
cctggacaaa gacttgaatg gatgggagac attaacccct ataacgacga cactacatac     180
aatcataaat ttaaaggaag agttacaatt acaagagata catccgcatc aaccgcctat     240
atggaacttt cctcattgag atctgaagac actgctgttt attactgtgc aagagaaact     300
gccgttatta ctactaacgc tatggattac tggggtcaag gaaccactgt taccgtctct     360
agtgcctcca ccaagggccc atcggtcttc cccctggcgc cctgctccag gagcacctcc     420
gagagcacag cggccctggg ctgcctggtc aaggactact ccccgaaccc ggtgacggtg     480
tcgtggaact caggcgctct gaccagcggc gtgcacacct tcccagctgt cctacagtcc     540
tcaggactct actccctcag cagcgtggtg accgtgccct ccagcaactt cggcacccag     600
acctacacct gcaacgtaga tcacaagccc agcaacacca aggtggacaa gacagttgag     660
cgcaaatgtt gtgtcgagtg cccaccgtgc ccagcaccac ctgtggcagg accgtcagtc     720
ttcctcttcc ccccaaaacc caaggacacc ctcatgatct cccggacccc tgaggtcacg     780
tgcgtggtgg tggacgtgag ccacgaagac cccgaggtcc agttcaactg gtacgtggac     840
ggcgtggagg tgcataatgc caagacaaag ccacgggagg agcagttcaa cagcacgttc     900
cgtgtggtca gcgtcctcac cgttgtgcac caggactggc tgaacggcaa ggagtacaag     960
tgcaaggtct ccaacaaagg cctcccagcc cccatcgaga aaccatctc caaaaccaaa    1020
gggcagcccc gagaaccaca ggtgtacacc ctgccccccat cccgggagga gatgaccaag    1080
aaccaggtca gcctgacctg cctggtcaaa ggcttctacc ccagcgacat cgccgtggag    1140
tgggagagca atgggcagcc ggagaacaac tacaagacca cacctcccat gctggactcc    1200
gacggctcct tcttcctcta cagcaagctc accgtggaca gagcaggtg gcagcagggg    1260
aacgtcttct catgctccgt gatgcatgag gctctgcaca accactacac gcagaagagc    1320
ctctccctgt ctccgggtaa a                                              1341
```

<210> SEQ ID NO 186
<211> LENGTH: 447
<212> TYPE: PRT
<213> ORGANISM: Artificial Sequence
<220> FEATURE:
<223> OTHER INFORMATION: Humanized antibody sequence

<400> SEQUENCE: 186

```
Glu Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Arg Leu Glu Trp Met
        35                  40                  45

Gly Asp Ile Asn Pro Tyr Asn Asp Asp Thr Thr Tyr Asn His Lys Phe
    50                  55                  60
```

```
Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Thr Ala Val Ile Thr Thr Asn Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 187
<211> LENGTH: 12
<212> TYPE: PRT
<213> ORGANISM: Artificial Sequence
<220> FEATURE:
<223> OTHER INFORMATION: Ab-17 and Ab-18 LCDR1
```

<400> SEQUENCE: 187

Ser Val Ser Ser Ser Ile Ser Ser Ser Asn Leu His
1               5                   10

<210> SEQ ID NO 188
<211> LENGTH: 7
<212> TYPE: PRT
<213> ORGANISM: Artificial Sequence
<220> FEATURE:
<223> OTHER INFORMATION: Ab-17 and Ab-18 LCDR2

<400> SEQUENCE: 188

Gly Thr Ser Asn Leu Ala Ser
1               5

<210> SEQ ID NO 189
<211> LENGTH: 8
<212> TYPE: PRT
<213> ORGANISM: Artificial Sequence
<220> FEATURE:
<223> OTHER INFORMATION: LCDR3

<400> SEQUENCE: 189

Gln Gln Trp Thr Thr Thr Tyr Thr
1               5

<210> SEQ ID NO 190
<211> LENGTH: 5
<212> TYPE: PRT
<213> ORGANISM: Artificial Sequence
<220> FEATURE:
<223> OTHER INFORMATION: Ab-17 and Ab-18 HCDR1

<400> SEQUENCE: 190

Asp Tyr Tyr Ile His
1               5

<210> SEQ ID NO 191
<211> LENGTH: 17
<212> TYPE: PRT
<213> ORGANISM: Artificial Sequence
<220> FEATURE:
<223> OTHER INFORMATION: Ab-17 and Ab-18 HCDR2

<400> SEQUENCE: 191

Arg Ile Asp Pro Asp Asn Gly Glu Ser Thr Tyr Val Pro Lys Phe Gln
1               5                   10                  15

Gly

<210> SEQ ID NO 192
<211> LENGTH: 13
<212> TYPE: PRT
<213> ORGANISM: Artificial Sequence
<220> FEATURE:
<223> OTHER INFORMATION: Synthetic peptide

<400> SEQUENCE: 192

Glu Gly Leu Asp Tyr Gly Asp Tyr Tyr Ala Val Asp Tyr
1               5                   10

<210> SEQ ID NO 193
<211> LENGTH: 390
<212> TYPE: DNA
<213> ORGANISM: Mus musculus -continued

<400> SEQUENCE: 193

```
atggattttc aggtgcagat tttcagcttc atgctaatca gtgtcacagt catattgtcc      60
agtggagaaa ttgtgctcac ccagtctcca gcactcatgg ctgcatctcc aggggagaag    120
gtcaccatca cctgcagtgt cagctcgagt ataagttcca gcaacttaca ctggtcccag    180
cagaagtcag gaacctcccc caaactctgg atttatggca catccaacct tgcttctgga    240
gtccctgttc gcttcagtgg cagtggatct gggacctctt attctctcac aatcagcagc    300
atggaggctg aagatgctgc cacttattac tgtcaacagt ggactactac gtatacgttc    360
ggatcgggga ccaagctgga gctgaaacgt                                      390
```

<210> SEQ ID NO 194
<211> LENGTH: 130
<212> TYPE: PRT
<213> ORGANISM: Mus musculus

<400> SEQUENCE: 194

```
Met Asp Phe Gln Val Gln Ile Phe Ser Phe Met Leu Ile Ser Val Thr
  1               5                  10                  15
Val Ile Leu Ser Ser Gly Glu Ile Val Leu Thr Gln Ser Pro Ala Leu
             20                  25                  30
Met Ala Ala Ser Pro Gly Glu Lys Val Thr Ile Thr Cys Ser Val Ser
         35                  40                  45
Ser Ser Ile Ser Ser Ser Asn Leu His Trp Ser Gln Gln Lys Ser Gly
     50                  55                  60
Thr Ser Pro Lys Leu Trp Ile Tyr Gly Thr Ser Asn Leu Ala Ser Gly
 65                  70                  75                  80
Val Pro Val Arg Phe Ser Gly Ser Gly Ser Gly Thr Ser Tyr Ser Leu
                 85                  90                  95
Thr Ile Ser Ser Met Glu Ala Glu Asp Ala Ala Thr Tyr Tyr Cys Gln
            100                 105                 110
Gln Trp Thr Thr Thr Tyr Thr Phe Gly Ser Gly Thr Lys Leu Glu Leu
        115                 120                 125
Lys Arg
    130
```

<210> SEQ ID NO 195
<211> LENGTH: 423
<212> TYPE: DNA
<213> ORGANISM: Mus musculus

<400> SEQUENCE: 195

```
atgggatgga actggatcat cttcttcctg atggcagtgg ttacagggt caattcagag       60
gtgcagttgc ggcagtctgg ggcagacctt gtgaagccag ggcctcagt caagttgtcc     120
tgcacagctt ctggcttcaa cattaaagac tactatatac actgggtgaa gcagaggcct    180
gaacagggcc tggagtggat tggaaggatt gatcctgata tggtgaaag tacatatgtc     240
ccgaagttcc agggcaaggc cactataaca gcagacacat catccaacac agcctaccta    300
caactcagaa gcctgacatc tgaggacact gccatctatt attgtgggag agaggggctc    360
gactatggtg actactatgc tgtggactac tggggtcaag gaacctcggt cacagtctcg    420
agc                                                                   423
```

<210> SEQ ID NO 196
<211> LENGTH: 141
<212> TYPE: PRT

<213> ORGANISM: Mus musculus

<400> SEQUENCE: 196

Met Gly Trp Asn Trp Ile Ile Phe Phe Leu Met Ala Val Val Thr Gly
1               5                   10                  15

Val Asn Ser Glu Val Gln Leu Arg Gln Ser Gly Ala Asp Leu Val Lys
            20                  25                  30

Pro Gly Ala Ser Val Lys Leu Ser Cys Thr Ala Ser Gly Phe Asn Ile
        35                  40                  45

Lys Asp Tyr Tyr Ile His Trp Val Lys Gln Arg Pro Glu Gln Gly Leu
    50                  55                  60

Glu Trp Ile Gly Arg Ile Asp Pro Asp Asn Gly Glu Ser Thr Tyr Val
65                  70                  75                  80

Pro Lys Phe Gln Gly Lys Ala Thr Ile Thr Ala Asp Thr Ser Ser Asn
                85                  90                  95

Thr Ala Tyr Leu Gln Leu Arg Ser Leu Thr Ser Glu Asp Thr Ala Ile
            100                 105                 110

Tyr Tyr Cys Gly Arg Glu Gly Leu Asp Tyr Gly Asp Tyr Tyr Ala Val
        115                 120                 125

Asp Tyr Trp Gly Gln Gly Thr Ser Val Thr Val Ser Ser
    130                 135                 140

<210> SEQ ID NO 197
<211> LENGTH: 390
<212> TYPE: DNA
<213> ORGANISM: Artificial Sequence
<220> FEATURE:
<223> OTHER INFORMATION: Humanized antibody sequence

<400> SEQUENCE: 197
atggatatgc gcgtgccggc gcagctgctg ggcctgctgc tgctgtggct gccgggcgcg      60
cgctgcgata ttcagctgac ccagagcccg agctttctga gcgcgagcgt gggcgatcgc     120
gtgaccatta cctgcagcgt gagcagcagc attagcagca gcaacctgca ttggtatcag     180
cagaaaccgg gcaaagcgcc gaaactgctg atttatggca ccagcaacct ggcgagcggc     240
gtgccgagcc gctttagcgg cagcggcagc ggcaccgaat ttaccctgac cattagcagc     300
ctgcagccgg aagattttgc gacctattat tgccagcagt ggaccaccac ctatacctttt    360
ggccagggca ccaaactgga aattaaacgt                                       390

<210> SEQ ID NO 198
<211> LENGTH: 130
<212> TYPE: PRT
<213> ORGANISM: Artificial Sequence
<220> FEATURE:
<223> OTHER INFORMATION: Humanized antibody sequence

<400> SEQUENCE: 198

Met Asp Met Arg Val Pro Ala Gln Leu Leu Gly Leu Leu Leu Leu Trp
1               5                   10                  15

Leu Pro Gly Ala Arg Cys Asp Ile Gln Leu Thr Gln Ser Pro Ser Phe
            20                  25                  30

Leu Ser Ala Ser Val Gly Asp Arg Val Thr Ile Thr Cys Ser Val Ser
        35                  40                  45

Ser Ser Ile Ser Ser Ser Asn Leu His Trp Tyr Gln Gln Lys Pro Gly
    50                  55                  60

Lys Ala Pro Lys Leu Leu Ile Tyr Gly Thr Ser Asn Leu Ala Ser Gly
65                  70                  75                  80

Val Pro Ser Arg Phe Ser Gly Ser Gly Ser Gly Thr Glu Phe Thr Leu
            85                  90                  95

Thr Ile Ser Ser Leu Gln Pro Glu Asp Phe Ala Thr Tyr Tyr Cys Gln
            100                 105                 110

Gln Trp Thr Thr Thr Tyr Thr Phe Gly Gln Gly Thr Lys Leu Glu Ile
            115                 120                 125

Lys Arg
    130

<210> SEQ ID NO 199
<211> LENGTH: 423
<212> TYPE: DNA
<213> ORGANISM: Artificial Sequence
<220> FEATURE:
<223> OTHER INFORMATION: Humanized antibody sequence

<400> SEQUENCE: 199
atggattgga cctggagcat tctgtttctg gtggcggcgc cgaccggcgc gcatagcgaa      60
gtgcagctgg tgcagagcgg cgcggaagtg aaaaaaccgg gcgcgagcgt gaaagtgagc     120
tgcaaagcga gcggctttaa cattaaagat tattatattc attgggtgcg ccaggcgccg     180
ggccagggcc tggaatggat gggccgcatt gatccggata acggcgaaag cacctatgtg     240
ccgaaatttc agggccgcgt gaccatgacc accgatacca gcaccagcac cgcgtatatg     300
gaactgcgca gcctgcgcag cgatgatacc gcggtgtatt attgcgcgcg cgaaggcctg     360
gattatggcg attattatgc ggtggattat tggggccagg gcaccctggt gaccgtctcg     420
agc                                                                   423

<210> SEQ ID NO 200
<211> LENGTH: 141
<212> TYPE: PRT
<213> ORGANISM: Artificial Sequence
<220> FEATURE:
<223> OTHER INFORMATION: Humanized antibody sequence

<400> SEQUENCE: 200

Met Asp Trp Thr Trp Ser Ile Leu Phe Leu Val Ala Ala Pro Thr Gly
1               5                   10                  15

Ala His Ser Glu Val Gln Leu Val Gln Ser Gly Ala Glu Val Lys Lys
            20                  25                  30

Pro Gly Ala Ser Val Lys Val Ser Cys Lys Ala Ser Gly Phe Asn Ile
            35                  40                  45

Lys Asp Tyr Tyr Ile His Trp Val Arg Gln Ala Pro Gly Gln Gly Leu
    50                  55                  60

Glu Trp Met Gly Arg Ile Asp Pro Asp Asn Gly Glu Ser Thr Tyr Val
65                  70                  75                  80

Pro Lys Phe Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Glu Gly Leu Asp Tyr Gly Asp Tyr Tyr Ala Val
            115                 120                 125

Asp Tyr Trp Gly Gln Gly Thr Leu Val Thr Val Ser Ser
    130                 135                 140

<210> SEQ ID NO 201
<211> LENGTH: 11

```
<212> TYPE: PRT
<213> ORGANISM: Artificial Sequence
<220> FEATURE:
<223> OTHER INFORMATION: Ab-19, Ab-20 and Ab-23 LCDR1

<400> SEQUENCE: 201

Arg Ala Ser Gln Asp Ile Ser Ser Tyr Leu Asn
1               5                   10

<210> SEQ ID NO 202
<211> LENGTH: 7
<212> TYPE: PRT
<213> ORGANISM: Artificial Sequence
<220> FEATURE:
<223> OTHER INFORMATION: Ab-19, Ab-20 and Ab-23 LCDR2

<400> SEQUENCE: 202

Ser Thr Ser Arg Leu Asn Ser
1               5

<210> SEQ ID NO 203
<211> LENGTH: 8
<212> TYPE: PRT
<213> ORGANISM: Artificial Sequence
<220> FEATURE:
<223> OTHER INFORMATION: Ab-19, Ab-20 and Ab-23 LCDR3

<400> SEQUENCE: 203

Gln Gln Asp Ile Lys His Pro Thr
1               5

<210> SEQ ID NO 204
<211> LENGTH: 5
<212> TYPE: PRT
<213> ORGANISM: Artificial Sequence
<220> FEATURE:
<223> OTHER INFORMATION: Ab-19, Ab-20 and Ab-23 HCDR1

<400> SEQUENCE: 204

Asp Tyr Ile Met His
1               5

<210> SEQ ID NO 205
<211> LENGTH: 17
<212> TYPE: PRT
<213> ORGANISM: Artificial Sequence
<220> FEATURE:
<223> OTHER INFORMATION: Ab-19, Ab-20 and Ab-23 HCDR2

<400> SEQUENCE: 205

Tyr Ile Asn Pro Tyr Asn Asp Asp Thr Glu Tyr Asn Glu Lys Phe Lys
1               5                   10                  15

Gly

<210> SEQ ID NO 206
<211> LENGTH: 11
<212> TYPE: PRT
<213> ORGANISM: Artificial Sequence
<220> FEATURE:
<223> OTHER INFORMATION: Ab-19, Ab-20 and Ab-23 HCDR3

<400> SEQUENCE: 206

Ser Ile Tyr Tyr Tyr Asp Ala Pro Phe Ala Tyr
1               5                   10

<210> SEQ ID NO 207
```

```
<211> LENGTH: 107
<212> TYPE: PRT
<213> ORGANISM: Mus musculus

<400> SEQUENCE: 207

Asp Ile Gln Met Thr Gln Thr Thr Ser Ser Leu Ser Ala Ser Leu Gly
1               5                   10                  15

Asp Arg Val Asn Ile Ser Cys Arg Ala Ser Gln Asp Ile Ser Ser Tyr
            20                  25                  30

Leu Asn Trp Tyr Gln Gln Lys Pro Asp Gly Thr Val Lys Leu Leu Ile
        35                  40                  45

Tyr Ser Thr Ser Arg Leu Asn Ser Gly Val Pro Ser Arg Phe Ser Gly
50                  55                  60

Ser Gly Ser Gly Thr Asp Tyr Ser Leu Thr Ile Ser Asn Leu Ala Gln
65                  70                  75                  80

Glu Asp Ile Ala Thr Tyr Phe Cys Gln Gln Asp Ile Lys His Pro Thr
                85                  90                  95

Phe Gly Gly Gly Thr Lys Leu Glu Leu Lys Arg
            100                 105

<210> SEQ ID NO 208
<211> LENGTH: 120
<212> TYPE: PRT
<213> ORGANISM: Mus musculus

<400> SEQUENCE: 208

Glu Val Gln Leu Gln Gln Ser Gly Pro Glu Leu Val Lys Pro Gly Ala
1               5                   10                  15

Ser Val Lys Met Ser Cys Lys Ala Ser Gly Phe Thr Phe Thr Asp Tyr
            20                  25                  30

Ile Met His Trp Val Lys Gln Lys Pro Gly Gln Gly Leu Glu Trp Ile
        35                  40                  45

Gly Tyr Ile Asn Pro Tyr Asn Asp Asp Thr Gly Tyr Asn Glu Lys Phe
50                  55                  60

Lys Gly Lys Ala Thr Leu Thr Ser Asp Lys Ser Ser Ser Thr Ala Tyr
65                  70                  75                  80

Met Asp Leu Ser Ser Leu Thr Ser Glu Gly Ser Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser
        115                 120

<210> SEQ ID NO 209
<211> LENGTH: 381
<212> TYPE: DNA
<213> ORGANISM: Mus musculus

<400> SEQUENCE: 209
atgatgtcct ctgctcagtt ccttggtctc ctgttgctct gttttcaagg taccagatgt      60
gatatccaga tgacacagac tacatcctcc ctgtctgcct ctctgggaga cagagtcaac     120
atcagctgca gggcaagtca ggacattagc agttatttaa actggtatca gcagaaacca     180
gatggaactg ttaaactcct gatctactcc acatcaagat aaactcagg agtcccatca      240 aggttcagtg gcagtgggtc tgggacagat tattctctca ctattagcaa cctggcacaa     300
gaagatattg ccacttactt ttgccaacag gatattaagc atccgacgtt cggtggaggc     360
```
accaagttgg agctgaaacg t                                                 381

<210> SEQ ID NO 210
<211> LENGTH: 127
<212> TYPE: PRT
<213> ORGANISM: Mus musculus

<400> SEQUENCE: 210

Met Met Ser Ser Ala Gln Phe Leu Gly Leu Leu Leu Cys Phe Gln
1               5                   10                  15

Gly Thr Arg Cys Asp Ile Gln Met Thr Gln Thr Ser Ser Leu Ser
            20                  25                  30

Ala Ser Leu Gly Asp Arg Val Asn Ile Ser Cys Arg Ala Ser Gln Asp
            35                  40                  45

Ile Ser Ser Tyr Leu Asn Trp Tyr Gln Gln Lys Pro Asp Gly Thr Val
50                  55                  60

Lys Leu Leu Ile Tyr Ser Thr Ser Arg Leu Asn Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Ala Gln Glu Asp Ile Ala Thr Tyr Phe Cys Gln Gln Asp Ile
            100                 105                 110

Lys His Pro Thr Phe Gly Gly Gly Thr Lys Leu Glu Leu Lys Arg
        115                 120                 125

<210> SEQ ID NO 211
<211> LENGTH: 417
<212> TYPE: DNA
<213> ORGANISM: Mus musculus

<400> SEQUENCE: 211
atggaatgga tctggatatt tctcttcctc ctgtcaggaa ctgcaggtgt ccactctgag    60
gtccagctgc agcagtctgg acctgagctg gtaaagcctg gggcttcagt gaagatgtcc   120
tgcaaggctt ctgggttcac attcactgac tacattatgc actgggtgaa gcagaagcct   180
gggcagggcc ttgagtggat tggatatatt aatccttaca atgatgatac tgaatacaat   240
gagaagttca aggcaaggc cacactgact tcagacaaat cctccagcac agcctacatg   300
gatctcagca gtctgacctc tgagggctct gcggtctatt actgtgcaag atcgattta   360 tactacgatg ccccgtttgc ttactggggc caagggactc tggtcacagt ctcgagc     417

<210> SEQ ID NO 212
<211> LENGTH: 139
<212> TYPE: PRT
<213> ORGANISM: Mus musculus

<400> SEQUENCE: 212

Met Glu Trp Ile Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Phe Thr Phe
        35                  40                  45

Thr Asp Tyr Ile Met His Trp Val Lys Gln Lys Pro Gln Gly Leu
    50                  55                  60

Glu Trp Ile Gly Tyr Ile Asn Pro Tyr Asn Asp Asp Thr Glu Tyr Asn
65                  70                  75                  80

```
Glu Lys Phe Lys Gly Lys Ala Thr Leu Thr Ser Asp Lys Ser Ser Ser
                85                  90                  95

Thr Ala Tyr Met Asp Leu Ser Ser Leu Thr Ser Glu Gly Ser Ala Val
            100                 105                 110

Tyr Tyr Cys Ala Arg Ser Ile Tyr Tyr Asp Ala Pro Phe Ala Tyr
        115                 120                 125

Trp Gly Gln Gly Thr Leu Val Thr Val Ser Ser
130                 135
```

```
<210> SEQ ID NO 213
<211> LENGTH: 381
<212> TYPE: DNA
<213> ORGANISM: Artificial Sequence
<220> FEATURE:
<223> OTHER INFORMATION: Humanized antibody sequence

<400> SEQUENCE: 213
atgatgtcct ctgctcagtt ccttggtctc ctgttgctct gttttcaagg taccagatgt      60
gatatccaga tgacccagtc tccatcctcc ctgtctgcat ctgtaggtga ccgtgtcacc     120
atcacttgcc gcgcaagtca ggatattagc agctatttaa attggtatca gcagaaacca     180
gggaaagccc ctaagctcct gatctattct acttcccgtt tgaatagtgg ggtcccatca     240
cgcttcagtg gcagtggctc tgggacagat ttcactctca ccatcagcag tctgcaacct     300
gaagattttg caacttacta ctgtcaacag gatattaaac accctacgtt cggtcaaggc     360
accaaggtgg agatcaaacg t                                               381
```

```
<210> SEQ ID NO 214
<211> LENGTH: 127
<212> TYPE: PRT
<213> ORGANISM: Artificial Sequence
<220> FEATURE:
<223> OTHER INFORMATION: Humanized antibody sequence

<400> SEQUENCE: 214

Met Met Ser Ser Ala Gln Phe Leu Gly Leu Leu Leu Leu Cys Phe Gln
1               5                   10                  15

Gly Thr Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Ser Ser Tyr Leu Asn Trp Tyr Gln Gln Lys Pro Gly Lys Ala Pro
    50                  55                  60

Lys Leu Leu Ile Tyr Ser Thr Ser Arg Leu Asn Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Asp Ile
            100                 105                 110

Lys His Pro Thr Phe Gly Gln Gly Thr Lys Val Glu Ile Lys Arg
        115                 120                 125
```

```
<210> SEQ ID NO 215
<211> LENGTH: 417
<212> TYPE: DNA
<213> ORGANISM: Mus musculus

<400> SEQUENCE: 215
atggaatgga tctggatatt tctcttcctc ctgtcaggaa ctgcaggtgt ccactctgag      60
```

```
gtgcagctgg tgcagtctgg ggctgaggtg aagaagcctg gtcctcggt gaaggtctcc      120 tgcaaggctt ctggttttac cttcaccgac tatattatgc actgggtgcg tcaggcccct      180
ggtcaagggc ttgagtggat gggctatatc aaccttata atgatgacac cgaatacaac      240
gagaagttca agggccgtgt cacgattacc gcggacaaat ccacgagcac agcctacatg      300
gagctgagca gcctgcgctc tgaggacacg gccgtgtatt actgtgcgcg ttcgatttat      360
tactacgatg ccccgtttgc ttactggggc caagggactc tggtcacagt ctcgagc        417

<210> SEQ ID NO 216
<211> LENGTH: 139
<212> TYPE: PRT
<213> ORGANISM: Artificial Sequence
<220> FEATURE:
<223> OTHER INFORMATION: Humanized antibody sequence

<400> SEQUENCE: 216

Met Glu Trp Ile Trp Ile Phe Leu Phe Leu Leu Ser Gly Thr Ala Gly
1               5                   10                  15

Val His Ser Glu Val Gln Leu Val Gln Ser Gly Ala Glu Val Lys Lys
            20                  25                  30

Pro Gly Ser Ser Val Lys Val Ser Cys Lys Ala Ser Gly Phe Thr Phe
        35                  40                  45

Thr Asp Tyr Ile Met His Trp Val Arg Gln Ala Pro Gly Gln Gly Leu
    50                  55                  60

Glu Trp Met Gly Tyr Ile Asn Pro Tyr Asn Asp Asp Thr Glu Tyr Asn
65                  70                  75                  80

Glu Lys Phe Lys Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Ile Tyr Tyr Tyr Asp Ala Pro Phe Ala Tyr
        115                 120                 125

Trp Gly Gln Gly Thr Leu Val Thr Val Ser Ser
    130                 135

<210> SEQ ID NO 217
<211> LENGTH: 318
<212> TYPE: DNA
<213> ORGANISM: Mus musculus

<400> SEQUENCE: 217
gacatccaga tgacccagtc tccatcctcc ctgtctgcat ctgtaggtga ccgtgtcacc       60
atcacttgcc gcgcaagtca ggatattagc agctatttaa attggtatca gcagaaacca      120
gggaaagccc ctaagctcct gatctattct acttcccgtt tgaatagtgg ggtcccatca      180
cgcttcagtg gcagtggctc tgggacagat ttcactctca ccatcagcag tctgcaacct      240
gaagattttg caacttacta ctgtcaacag gatattaaac ccctacgtt cggtcaaggc       300 accaaggtgg agatcaaa                                                    318

<210> SEQ ID NO 218
<211> LENGTH: 106
<212> TYPE: PRT
<213> ORGANISM: Mus musculus

<400> SEQUENCE: 218

Asp Ile Gln Met Thr Gln Ser Pro Ser Ser Leu Ser Ala Ser Val Gly
```

```
                1               5                  10                 15
Asp Arg Val Thr Ile Thr Cys Arg Ala Ser Gln Asp Ile Ser Ser Tyr
                            20                  25                 30

Leu Asn Trp Tyr Gln Gln Lys Pro Gly Lys Ala Pro Lys Leu Leu Ile
                35                  40                  45

Tyr Ser Thr Ser Arg Leu Asn Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Ile Lys His Pro Thr
                85                  90                  95

Phe Gly Gln Gly Thr Lys Val Glu Ile Lys
                100                 105
```

<210> SEQ ID NO 219
<211> LENGTH: 360
<212> TYPE: DNA
<213> ORGANISM: Mus musculus

<400> SEQUENCE: 219

```
gaggtgcagc tggtgcagtc tggggctgag gtgaagaagc ctgggtcctc ggtgaaggtc    60
tcctgcaagg cttctggttt taccttcacc gactatatta tgcactgggt gcgtcaggcc   120
cctggtcaag gcttgagtg gatgggctat atcaaccctt ataatgatga caccgaatac   180
aacgagaagt tcaagggccg tgtcacgatt accgcggaca atccacgag cacagcctac   240
atggagctga gcagcctgcg ctctgaggac acggccgtgt attactgtgc gcgttcgatt   300
tattactacg atgccccgtt tgcttactgg ggccaaggga ctctggtcac cgtctctagt   360
```

<210> SEQ ID NO 220
<211> LENGTH: 120
<212> TYPE: PRT
<213> ORGANISM: Mus musculus

<400> SEQUENCE: 220

```
Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
                20                  25                  30

Ile Met His Trp Val Arg Gln Ala Pro Gly Gln Gly Leu Glu Trp Met
                35                  40                  45

Gly Tyr Ile Asn Pro Tyr Asn Asp Asp Thr Glu Tyr Asn Glu Lys Phe
            50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Tyr Tyr Asp Ala Pro Phe Ala Tyr Trp Gly Gln
                100                 105                 110

Gly Thr Leu Val Thr Val Ser Ser
            115                 120
```

<210> SEQ ID NO 221
<211> LENGTH: 639
<212> TYPE: DNA
<213> ORGANISM: Mus musculus

<400> SEQUENCE: 221

```
gacatccaga tgacccagtc tccatcctcc ctgtctgcat ctgtaggtga ccgtgtcacc    60
atcacttgcc gcgcaagtca ggatattagc agctatttaa attggtatca gcagaaacca   120
gggaaagccc ctaagctcct gatctattct acttcccgtt tgaatagtgg ggtcccatca   180
cgcttcagtg gcagtggctc tgggacagat ttcactctca ccatcagcag tctgcaacct   240
gaagattttg caacttacta ctgtcaacag gatattaaac accctacgtt cggtcaaggc   300
accaaggtgg agatcaaacg tacggtggct gcaccatctg tcttcatctt cccgccatct   360
gatgagcagt tgaaatctgg aactgcctct gttgtgtgcc tgctgaataa cttctatccc   420
agagaggcca agtacagtg gaaggtggat aacgccctcc aatcgggtaa ctcccaggag   480
agtgtcacag agcaggacag caaggacagc acctacagcc tcagcagcac cctgacgctg   540
agcaaagcag actacgagaa acacaaagtc tacgcctgcg aagtcaccca tcagggcctg   600
agctcgcccg tcacaaagag cttcaacagg ggagagtgt                          639

<210> SEQ ID NO 222
<211> LENGTH: 213
<212> TYPE: PRT
<213> ORGANISM: Mus musculus

<400> SEQUENCE: 222

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Ser Thr Ser Arg Leu Asn Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Ile Lys His Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 223
<211> LENGTH: 1338
<212> TYPE: DNA
<213> ORGANISM: Mus musculus
```

<400> SEQUENCE: 223

```
gaggtgcagc tggtgcagtc tggggctgag gtgaagaagc ctgggtcctc ggtgaaggtc      60
tcctgcaagg cttctggttt taccttcacc gactatatta tgcactgggt gcgtcaggcc     120
cctggtcaag gcttgagtg gatgggctat atcaacccctt ataatgatga caccgaatac     180
aacgagaagt tcaagggccg tgtcacgatt accgcggaca atccacgag cacagcctac      240
atggagctga gcagcctgcg ctctgaggac acggccgtgt attactgtgc gcgttcgatt     300
tattactacg atgccccgtt tgcttactgg ggccaaggga ctctggtcac cgtctctagt     360
gcctccacca agggcccatc ggtcttcccc ctggcgccct gctccaggag cacctccgag     420
agcacagcgg ccctgggctg cctggtcaag gactacttcc ccgaaccggt gacggtgtcg     480
tggaactcag gcgctctgac cagcggcgtg cacaccttcc cagctgtcct acagtcctca     540
ggactctact ccctcagcag cgtggtgacc gtgcctcca gcaacttcgg cacccagacc      600
tacacctgca acgtagatca caagcccagc aacaccaagg tggacaagac agttgagcgc     660
aaatgttgtg tcgagtgccc accgtgccca gcaccacctg tggcaggacc gtcagtcttc     720
ctcttcccccc caaaacccaa ggacaccctc atgatctccc ggacccctga ggtcacgtgc    780
gtggtggtgg acgtgagcca cgaagacccc gaggtccagt tcaactggta cgtggacggc     840
gtggaggtgc ataatgccaa gacaaagcca cgggaggagc agttcaacag cacgttccgt     900
gtggtcagcg tcctcaccgt tgtgcaccag gactggctga acggcaagga gtacaagtgc     960
aaggtctcca acaaaggcct cccagccccc atcgagaaaa ccatctccaa aaccaagggg   1020
cagccccgag aaccacaggt gtacaccctg cccccatccc gggaggagat gaccaagaac   1080
caggtcagcc tgacctgcct ggtcaaaggc ttctacccca gcgacatcgc cgtggagtgg   1140
gagagcaatg ggcagccgga gaacaactac aagaccacac ctcccatgct ggactccgac   1200
ggctccttct cctctacag caagctcacc gtggacaaga gcaggtggca gcaggggaac    1260
gtcttctcat gctccgtgat gcatgaggct ctgcacaacc actacacgca gaagagcctc   1320
tccctgtctc cgggtaaa                                                  1338
```

<210> SEQ ID NO 224
<211> LENGTH: 446
<212> TYPE: PRT
<213> ORGANISM: Mus musculus

<400> SEQUENCE: 224

```
Glu Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Ile Met His Trp Val Arg Gln Ala Pro Gly Gln Gly Leu Glu Trp Met
        35                  40                  45

Gly Tyr Ile Asn Pro Tyr Asn Asp Asp Thr Glu Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Tyr Tyr Asp Ala Pro Phe Ala Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 225
<211> LENGTH: 11
<212> TYPE: PRT
<213> ORGANISM: Artificial Sequence
<220> FEATURE:
<223> OTHER INFORMATION: Ab-21 and Ab-22 LCDR1

<400> SEQUENCE: 225

Lys Ala Ser Gln Asp Val Phe Thr Ala Val Ala
1               5                   10

<210> SEQ ID NO 226
<211> LENGTH: 7
<212> TYPE: PRT
<213> ORGANISM: Artificial Sequence
```

```
<220> FEATURE:
<223> OTHER INFORMATION: Ab-21 and Ab-22 LCDR2

<400> SEQUENCE: 226

Trp Ala Ser Thr Arg His Thr
1               5

<210> SEQ ID NO 227
<211> LENGTH: 9
<212> TYPE: PRT
<213> ORGANISM: Artificial Sequence
<220> FEATURE:
<223> OTHER INFORMATION: Ab-21 and Ab-22 LCDR3

<400> SEQUENCE: 227

Gln Gln Tyr Ser Ser Tyr Pro Leu Thr
1               5

<210> SEQ ID NO 228
<211> LENGTH: 5
<212> TYPE: PRT
<213> ORGANISM: Artificial Sequence
<220> FEATURE:
<223> OTHER INFORMATION: Ab-21 and Ab-22 HCDR1

<400> SEQUENCE: 228

Asp Tyr Tyr Met His
1               5

<210> SEQ ID NO 229
<211> LENGTH: 17
<212> TYPE: PRT
<213> ORGANISM: Artificial Sequence
<220> FEATURE:
<223> OTHER INFORMATION: Ab-21 and Ab-22 HCDR2

<400> SEQUENCE: 229

Arg Ile Asp Pro Glu Asn Gly Asp Ile Ile Tyr Asp Pro Lys Phe Gln
1               5                   10                  15

Gly

<210> SEQ ID NO 230
<211> LENGTH: 10
<212> TYPE: PRT
<213> ORGANISM: Artificial Sequence
<220> FEATURE:
<223> OTHER INFORMATION: Ab-21 and Ab-22 HCDR3

<400> SEQUENCE: 230

Asp Ala Gly Asp Pro Ala Trp Phe Thr Tyr
1               5                   10

<210> SEQ ID NO 231
<211> LENGTH: 381
<212> TYPE: DNA
<213> ORGANISM: Mus musculus

<400> SEQUENCE: 231
atgaagtcac agacccaggt ctttgtatac atgttgctgt ggttgtctgg tgttgaagga      60
gacattgtga tgacccagtc tcacaaattc atgtccacgt cagtaggaga cagggtcacc     120
atcacctgca aggccagtca ggatgtcttt actgctgtag cctggtatca acagaaacca     180
ggacaatctc ctaaaactac tgatttactg gcatccaccc ggcacactgg agtccctgat     240
cgcttcacag gcagtggatc tgggacagat ttcactctca ccattagcaa tgtgcagtct     300
```

```
gaagacttgg cagattattt ctgtcaacaa tatagcagct atcctctcac gttcggtgct    360
gggaccaagt tggagctgaa a                                              381
```

<210> SEQ ID NO 232
<211> LENGTH: 128
<212> TYPE: PRT
<213> ORGANISM: Mus musculus

<400> SEQUENCE: 232

```
Met Lys Ser Gln Thr Gln Val Phe Val Tyr Met Leu Leu Trp Leu Ser
1               5                   10                  15

Gly Val Glu Gly Asp Ile Val Met Thr Gln Ser His Lys Phe Met Ser
            20                  25                  30

Thr Ser Val Gly Asp Arg Val Thr Ile Thr Cys Lys Ala Ser Gln Asp
        35                  40                  45

Val Phe Thr Ala Val Ala Trp Tyr Gln Gln Lys Pro Gly Gln Ser Pro
    50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Asp Tyr Phe Cys Gln Gln Tyr Ser
            100                 105                 110

Ser Tyr Pro Leu Thr Phe Gly Ala Gly Thr Lys Leu Glu Leu Lys Arg
        115                 120                 125
```

<210> SEQ ID NO 233
<211> LENGTH: 411
<212> TYPE: DNA
<213> ORGANISM: Mus musculus

<400> SEQUENCE: 233

```
atgggatgga actggatcat cttcttcctg atggcagtgg ttacaggggt caattcagag    60
gttcagctgc agcagtctgg ggctgagctt gtgaggccag ggccttagt caagttgtcc    120 tgcaaagctt ctggcttcaa tattaaagac tactatatgc actgggtgaa gcagaggcct    180
gaacagggcc tggagtggat tggaaggatt gatcctgaga atggtgatat tatatatgac    240
ccgaagttcc agggcaaggc cagtataaca acagacacat cctccaacac agcctacctg    300
cagctcagca gcctgacgtc tgaggacact gccgtctatt actgtgctta cgatgctggt    360 gacccgcct ggtttactta ctggggccaa gggactctgg tcaccgtctc g              411
```

<210> SEQ ID NO 234
<211> LENGTH: 138
<212> TYPE: PRT
<213> ORGANISM: Mus musculus

<400> SEQUENCE: 234

```
Met Gly Trp Asn Trp Ile Ile Phe Phe Leu Met Ala Val Val Thr Gly
1               5                   10                  15

Val Asn Ser Glu Val Gln Leu Gln Gln Ser Gly Ala Glu Leu Val Arg
            20                  25                  30

Pro Gly Ala Leu Val Lys Leu Ser Cys Lys Ala Ser Gly Phe Asn Ile
        35                  40                  45

Lys Asp Tyr Tyr Met His Trp Val Lys Gln Arg Pro Glu Gln Gly Leu
    50                  55                  60
```

Glu Trp Ile Gly Arg Ile Asp Pro Glu Asn Gly Asp Ile Ile Tyr Asp
65                  70                  75                  80

Pro Lys Phe Gln Gly Lys Ala Ser Ile Thr Thr Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Tyr Asp Ala Gly Asp Pro Ala Trp Phe Thr Tyr Trp
        115                 120                 125

Gly Gln Gly Thr Leu Val Thr Val Ser Ser
    130                 135

<210> SEQ ID NO 235
<211> LENGTH: 324
<212> TYPE: DNA
<213> ORGANISM: Mus musculus

<400> SEQUENCE: 235

```
gatatccaga tgacccagag cccgagcagc ctgagcgcga gcgtgggcga tcgcgtgacc      60
attacctgca aagcgagcca ggatgtgttt accgcggtgg cgtggtatca gcagaaaccg     120
ggcaaagcgc cgaaactgct gatttattgg gcgagcaccc gccataccgg cgtgccgagt     180
cgctttagcg gcagcggcag cggcaccgat tttaccctga ccattagcag cctgcagccg     240
gaagattttg cgacctatta ttgccagcag tatagcagct atccgctgac ctttggcggc     300
ggcaccaaag tggaaattaa acgt                                           324
```

<210> SEQ ID NO 236
<211> LENGTH: 108
<212> TYPE: PRT
<213> ORGANISM: Mus musculus

<400> SEQUENCE: 236

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Phe Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Leu
                85                  90                  95

Thr Phe Gly Gly Gly Thr Lys Val Glu Ile Lys Arg
            100                 105

<210> SEQ ID NO 237
<211> LENGTH: 357
<212> TYPE: DNA
<213> ORGANISM: Mus musculus

<400> SEQUENCE: 237

```
gaagtgcagc tggtgcagag cggcgcggaa gtgaaaaaac cgggcgcgag cgtgaaagtg      60
agctgcaaag cgagcggctt taacattaaa gattattata tgcattgggt gcgccaggcg     120
ccgggccagg gcctggaatg gatcggccgc attgatccgg aaaacggcga tattatttat     180
gatccgaaat ttcagggccg cgtgaccatg accaccgata ccagcaccag caccgcgtat     240
```

```
atggaactgc gcagcctgcg cagcgatgat accgcggtgt attattgcgc gtatgatgcg    300
ggcgatccgg cgtggtttac ctattggggc cagggcaccc tggtgaccgt ctcgagc      357
```

<210> SEQ ID NO 238
<211> LENGTH: 119
<212> TYPE: PRT
<213> ORGANISM: Mus musculus

<400> SEQUENCE: 238

```
Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
                20                  25                  30

Tyr Met His Trp Val Arg Gln Ala Pro Gly Gln Gly Leu Glu Trp Ile
            35                  40                  45

Gly Arg Ile Asp Pro Glu Asn Gly Asp Ile Ile Tyr Asp Pro Lys Phe
        50                  55                  60

Gln Gly Arg Val Thr Met Thr Thr Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Ala Tyr Asp Ala Gly Asp Pro Ala Trp Phe Thr Tyr Trp Gly Gln Gly
            100                 105                 110

Thr Leu Val Thr Val Ser Ser
        115
```

<210> SEQ ID NO 239
<211> LENGTH: 15
<212> TYPE: PRT
<213> ORGANISM: Artificial Sequence
<220> FEATURE:
<223> OTHER INFORMATION: Synthetic peptide

<400> SEQUENCE: 239

```
Lys Ala Ser Gln Ser Val Asp Tyr Asp Gly Thr Ser Tyr Met Asn
1               5                   10                  15
```

<210> SEQ ID NO 240
<211> LENGTH: 7
<212> TYPE: PRT
<213> ORGANISM: Artificial Sequence
<220> FEATURE:
<223> OTHER INFORMATION: Synthetic peptide

<400> SEQUENCE: 240

```
Ala Ala Ser Asn Leu Glu Ser
1               5
```

<210> SEQ ID NO 241
<211> LENGTH: 9
<212> TYPE: PRT
<213> ORGANISM: Artificial Sequence
<220> FEATURE:
<223> OTHER INFORMATION: Synthetic peptide

<400> SEQUENCE: 241

```
Gln Gln Ser Asn Glu Asp Pro Phe Thr
1               5
```

<210> SEQ ID NO 242
<211> LENGTH: 5

<212> TYPE: PRT
<213> ORGANISM: Artificial Sequence
<220> FEATURE:
<223> OTHER INFORMATION: Synthetic peptide

<400> SEQUENCE: 242

Thr Tyr Trp Met Asn
1               5

<210> SEQ ID NO 243
<211> LENGTH: 17
<212> TYPE: PRT
<213> ORGANISM: Artificial Sequence
<220> FEATURE:
<223> OTHER INFORMATION: Synthetic peptide

<400> SEQUENCE: 243

Met Ile His Pro Ser Ala Ser Glu Ile Arg Leu Asp Gln Lys Phe Lys
1               5                   10                  15

Asp

<210> SEQ ID NO 244
<211> LENGTH: 9
<212> TYPE: PRT
<213> ORGANISM: Artificial Sequence
<220> FEATURE:
<223> OTHER INFORMATION: Synthetic peptide

<400> SEQUENCE: 244

Ser Gly Glu Trp Gly Ser Met Asp Tyr
1               5

<210> SEQ ID NO 245
<211> LENGTH: 657
<212> TYPE: DNA
<213> ORGANISM: Mus musculus

<400> SEQUENCE: 245
gacattgtgt tgacccagtc tccagcttct ttggctgtgt ctctagggca gagggccacc      60
atcgcctgca aggccagcca aagtgttgat tatgatggta ctagttatat gaattggtac     120
caacagaaac caggacagcc acccaaactc ctcatctatg ctgcatccaa tctagaatct     180
gagatcccag ccaggtttag tggcactggg tctgggacag acttcaccct caacatccat     240
cctgtggagg aggaggatat acaaacctat tactgtcagc aaagtaatga ggatccgttc     300
acgttcggag gggggaccaa gttggaaata aaacgggctg atgctgcacc aactgtatcc     360
atcttcccac catccagtga gcagttaaca tctggaggtg cctcagtcgt gtgcttcttg     420
aacaacttct accccaaaga catcaatgtc aagtggaaga ttgatggcag tgaacgacaa     480
aatggcgtcc tgaacagttg gactgatcag gacagcaaag acagcaccta cagcatgagc     540
agcaccctca cgttgaccaa ggacgagtat gaacgacata acagctatac ctgtgaggcc     600
actcacaaga catcaacttc acccattgtc aagagcttca caggaatga gtgttag         657

<210> SEQ ID NO 246
<211> LENGTH: 218
<212> TYPE: PRT
<213> ORGANISM: Mus musculus

<400> SEQUENCE: 246

Asp Ile Val Leu Thr Gln Ser Pro Ala Ser Leu Ala Val Ser Leu Gly
1               5                   10                  15

Gln Arg Ala Thr Ile Ala Cys Lys Ala Ser Gln Ser Val Asp Tyr Asp
                20                  25                  30

Gly Thr Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Glu Ile Pro Ala
        50                  55                  60

Arg Phe Ser Gly Thr Gly Ser Gly Thr Asp Phe Thr Leu Asn Ile His
65                  70                  75                  80

Pro Val Glu Glu Glu Asp Ile Thr Thr Tyr Tyr Cys Gln Gln Ser Asn
                85                  90                  95

Glu Asp Pro Phe Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 247
<211> LENGTH: 442
<212> TYPE: PRT
<213> ORGANISM: Mus musculus

<400> SEQUENCE: 247

Gln Val Gln Leu Gln Gln Pro Gly Thr Glu Leu Val Arg Pro Gly Thr
1               5                   10                  15

Ser Val Lys Leu Ser Cys Lys Ala Ser Gly Tyr Ile Phe Thr Thr Tyr
                20                  25                  30

Trp Met Asn Trp Val Lys Gln Arg Pro Gly Gln Gly Leu Glu Trp Ile
            35                  40                  45

Gly Met Ile His Pro Ser Ala Ser Glu Ile Arg Leu Asp Gln Lys Phe
        50                  55                  60

Lys Asp Lys Ala Thr Leu Thr Leu Asp Lys Ser Ser Ser Thr Ala Tyr
65                  70                  75                  80

Met His Leu Ser Gly Pro Thr Ser Val Asp Ser Ala Val Tyr Tyr Cys
                85                  90                  95

Ala Arg Ser Gly Glu Trp Gly Ser Met Asp Tyr Trp Gly Gln Gly Thr
            100                 105                 110

Ser Val Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

| | | | | | | | | | | | |
|---|---|---|---|---|---|---|---|---|---|---|---|
| Ser | Asp | Leu | Tyr | Thr | Leu | Ser | Ser | Val | Thr | Val | Pro | Ser | Ser | Thr |
| | | | 180 | | | | 185 | | | | 190 | | | |

Ser Asp Leu Tyr Thr Leu Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
            245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
        290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
            325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
            355                 360                 365

Pro Glu Asp Ile Thr Val Glu Trp Gln Trp Asn Gly Gln Pro Ala Glu
        370                 375                 380

Asn Tyr Lys Asn Thr Gln Pro Ile Met Asp Thr Asp Gly Ser Tyr Phe
385                 390                 395                 400

Ile Tyr Ser Lys Leu Asn Val Gln Lys Ser Asn Trp Glu Ala Gly Asn
            405                 410                 415

Thr Phe Thr Cys Ser Val Leu His Glu Gly Leu His Asn His His Thr
            420                 425                 430

Glu Lys Ser Leu Ser His Ser Pro Gly Lys
            435                 440

```
<210> SEQ ID NO 248
<211> LENGTH: 1329
<212> TYPE: DNA
<213> ORGANISM: Mus musculus

<400> SEQUENCE: 248
caggtccaac tacagcagcc tgggactgag ctggtgaggc ctggaacttc agtgaagttg      60
tcctgtaagg cttctggcta catcttcacc acctactgga tgaactgggt gaaacagagg     120
cctggacaag gccttgagtg gattggcatg attcatcctt ccgcaagtga aattaggttg     180
gatcagaaat tcaaggacaa ggccacattg actcttgaca atcctccag cacagcctat      240 atgcacctca gcggcccgac atctgtggat tctgcggtct attactgtgc aagatcaggg     300 gaatggggt ctatggacta ctggggtcaa ggaacctcag tcaccgtctc ctcagccaaa      360
acgacacccc catctgtcta tccactggcc cctggatctg ctgccaaac taactccatg      420 gtgaccctgg gatgcctggt caagggctat ttccctgagc cagtgacagt gacctggaac     480
tctggatccc tgtccagcgg tgtgcacacc ttcccagctg tcctgcagtc tgacctctac     540
actctgagca gctcagtgac tgtcccctcc agcacctggc ccagcgagac cgtcacctgc     600
```

```
aacgttgccc acccggccag cagcaccaag gtggacaaga aaattgtgcc cagggattgt    660
ggttgtaagc cttgcatatg tacagtccca gaagtatcat ctgtcttcat cttccccca    720 aagcccaagg atgtgctcac cattactctg actcctaagg tcacgtgtgt tgtggtagac    780
atcagcaagg atgatcccga ggtccagttc agctggtttg tagatgatgt ggaggtgcac    840
acagctcaga cgcaaccccg ggaggagcag ttcaacagca ctttccgctc agtcagtgaa    900
cttcccatca tgcaccagga ctggctcaat ggcaaggagt tcaaatgcag ggtcaacagt    960
gcagctttcc ctgcccccat cgagaaaacc atctccaaaa ccaaaggcag accgaaggct   1020
ccacaggtgt acaccattcc acctcccaag gagcagatgg ccaaggataa agtcagtctg   1080
acctgcatga taacagactt cttccctgaa gacattactg tggagtggca gtggaatggg   1140
cagccagcgg agaactacaa gaacactcag cccatcatgg acacagatgg ctcttacttc   1200
atctacagca agctcaatgt gcagaagagc aactgggagg caggaaatac tttcacctgc   1260
tctgtgttac atgagggcct gcacaaccac catactgaga agagcctctc ccactctcct   1320
ggtaaatga                                                           1329
```

HIGH CONCENTRATION ANTIBODY FORMULATIONS

CROSS-REFERENCE TO RELATED APPLICATIONS

The present application claims the benefit of priority of U.S. Provisional Application No. 61/334,986 filed May 14, 2010, the disclosure of which is incorporated herein by reference in its entirety.

BACKGROUND

Highly concentrated liquid antibody formulations are useful for delivering doses in smaller volume. However, highly concentrated protein formulations pose several problems. One problem is instability due to the formation of particulates. Another problem is increased viscosity as a result of numerous intermolecular interactions from the macromolecular nature of antibodies. Highly viscous formulations are difficult to manufacture, draw into a syringe, and inject. The use of force in manipulating the viscous formulations leads to excessive frothing, which can lead to denaturation and inactivation of active biologics.

U.S. Pat. No. 6,875,432 and U.S. Patent Application Publication Nos. 2006/0182740, 2007/0172479, 2008/0160014 disclose antibody formulations and methods of making them. None of these publications disclose the antibodies referenced herein.

SUMMARY OF INVENTION

The present disclosure is based on the discovery that the addition of calcium acetate at low concentrations, e.g., 5-10 mM, reduced the effective viscosity in formulations comprising a high concentration of a selected anti-sclerostin antibody. In contrast, the same concentration of calcium acetate did not significantly reduce viscosity of other antibody formulations. In one aspect, the formulation is sterile and when in liquid or reconstituted liquid form comprises (a) an anti-sclerostin antibody at a concentration of at least 70 mg/mL, wherein the antibody comprises a set of six CDRs selected from the group consisting of SEQ ID NOs: 1-5 (Ab-A and Ab-1 CDRs), 15-20 (Ab-B CDRs), 25-30 (Ab-C CDRs), 35-40 (Ab-D CDRs), 45-50 (Ab-2 CDRs), 55-60 (Ab-3 and Ab-15 CDRs), 73-78 (Ab-4 and Ab-5 CDRs), 91-96 (Ab-6 CDRs), 101-106 (Ab-7 CDRs), 111-116 (Ab-8 CDRs), 121-126 (Ab-9 CDRs), 131-136 (Ab-10 CDRs), 141-146 (Ab-11 and Ab-16 CDRs), 159-164 (Ab-12 CDRs), 169-174 (Ab-13 and Ab-14 CDRs), 187-192 (Ab-17 and Ab-18 CDRs), 201-206 (Ab-19, Ab-20 and Ab-23 CDRs), 225-229 (Ab-21 and Ab-22 CDRs), or 239-244 (Ab-24 CDRs); and (b) a calcium salt at a concentration ranging from about 1 mM to about 20 mM, or from about 5 mM to about 10 mM, wherein the formulation has an absolute viscosity of about 10 cP or less. Absolute viscosity as described herein is measured was measured using Brookfield LV-DVII cone and plate viscometer with a CPE-40 spindle with matching sample cup temperature regulated by a circulating water bath at constant 25° C.

In some embodiments, the calcium salt is selected from the group consisting of calcium acetate, calcium carbonate and calcium chloride. In one embodiment, the calcium salt is calcium acetate. Alternatively, in some embodiments, the calcium salt is present at a concentration that reduces viscosity of an antibody formulation by at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more compared to the same formulation of antibody lacking the calcium salt.

In a related aspect, the formulation is sterile and when in liquid or reconstituted liquid form comprises (a) an anti-sclerostin antibody at a concentration of from about 70 mg/mL to about 200 mg/mL, wherein the antibody comprises a set of six CDRs selected from the group consisting of SEQ ID NOs: 1-5 (Ab-A and Ab-1 CDRs), 15-20 (Ab-B CDRs), 25-30 (Ab-C CDRs), 35-40 (Ab-D CDRs), 45-50 (Ab-2 CDRs), 55-60 (Ab-3 and Ab-15 CDRs), 73-78 (Ab-4 and Ab-5 CDRs), 91-96 (Ab-6 CDRs), 101-106 (Ab-7 CDRs), 111-116 (Ab-8 CDRs), 121-126 (Ab-9 CDRs), 131-136 (Ab-10 CDRs), 141-146 (Ab-11 and Ab-16 CDRs), 159-164 (Ab-12 CDRs), 169-174 (Ab-13 and Ab-14 CDRs), 187-192 (Ab-17 and Ab-18 CDRs), 201-206 (Ab-19, Ab-20 and Ab-23 CDRs), 225-229 (Ab-21 and Ab-22 CDRs), or 239-244 (Ab-24 CDRs); and (b) calcium acetate at a concentration ranging from about 5 mM to about 15 mM, or from about 5 mM to about 10 mM, wherein the formulation has an absolute viscosity of about 10 cP or less. Alternatively, in some embodiments, the calcium acetate is present at a concentration that reduces viscosity of an antibody formulation by at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%. 40%, 41%, 42%, 43%, 44%, 45%, 46%, 47%, 48%, 49%, 50%, 51%, 52%, 53%, 54%, 55%, 56%, 57%, 58%, 59%, 60% or more compared to the same formulation of antibody lacking the calcium acetate.

Also provided is a method for reducing the viscosity of a protein formulation, the method comprising; adding calcium acetate at a concentration of between about 1 mM and about 20 mM, to an anti-sclerostin immunoglobulin formulation, wherein the formulation comprises an immunoglobulin at a concentration of from about 70 mg/mL to about 200 mg/mL, wherein the viscosity of the formulation with the calcium acetate is reduced compared to the viscosity of an antibody formulation without the calcium acetate.

In another aspect, the formulation is sterile and has an absolute viscosity of about 10 cP or less comprising: (a) Ab-5 at a concentration of at least 70 mg/mL to about 200 mg/mL; (b) calcium acetate at a concentration ranging from about 1 mM to about 20 mM; and (c) a polyol such as sucrose, for example, in an amount ranging from about 1% w/v to about 12% w/v. In certain embodiments, the polyol is in amount ranging from about 4% to 10%. In some embodiments, the immunoglobulin comprises the amino acid sequences of SEQ ID NO: 86 (Ab-5 heavy chain variable region) and/or SEQ ID NO: 84 (Ab-5 light chain variable region).

In another aspect, the formulation is sterile and has an absolute viscosity of about 10 cP or less and comprises (a) Ab-5 at a concentration of at least 70 mg/mL to about 200 mg/mL; (b) calcium acetate at a concentration ranging from about 1 mM to about 20 mM; and (c) a polyol such as sucrose, for example, in an amount ranging from about 4% w/v to about 6% w/v.

In any of the preceding aspects, in some embodiments, the formulation further comprises (c) an acetate buffer, for example, sodium acetate, at a concentration of from about 5 mM to about 15 mM, or from about 5 mM to about 10 mM. In some embodiments, the total concentration of acetate is about 10 mM to about 50 mM, or about 20 mM to about 40 mM.

In a different aspect, the formulation is sterile and when in liquid or reconstituted liquid form comprises (a) an anti-sclerostin antibody at a concentration of from about 70 mg/mL to about 200 mg/mL, wherein the antibody comprises a set of six CDRs selected from the group consisting of SEQ ID NOs: 1-5 (Ab-A and Ab-1 CDRs), 15-20 (Ab-B CDRs), 25-30 (Ab-C CDRs), 35-40 (Ab-D CDRs), 45-50 (Ab-2 CDRs), 55-60 (Ab-3 and Ab-15 CDRs), 73-78 (Ab-4 and Ab-5 CDRs), 91-96 (Ab-6 CDRs), 101-106 (Ab-7 CDRs), 111-116 (Ab-8 CDRs), 121-126 (Ab-9 CDRs), 131-136 (Ab-10 CDRs), 141-146 (Ab-11 and Ab-16 CDRs), 159-164 (Ab-12 CDRs), 169-174 (Ab-13 and Ab-14 CDRs), 187-192 (Ab-17 and Ab-18 CDRs), 201-206 (Ab-19, Ab-20 and Ab-23 CDRs), 225-229 (Ab-21 and Ab-22 CDRs), or 239-244 (Ab-24 CDRs); and (b) an acetate salt and/or acetate buffer at a concentration ranging from about 10 mM to about 50 mM acetate, or from about 20 mM to about 40 mM acetate, wherein the formulation has an absolute viscosity of about 10 cP or less. In some embodiments, the acetate salt and/or buffer comprises calcium acetate and/or sodium acetate. Alternatively, in some embodiments, the acetate salt and/or buffer is present at a concentration that reduces viscosity of an antibody formulation by at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60% or more compared to the same formulation of antibody lacking the acetate salt and/or buffer.

In any of the preceding aspects, in some embodiments, the total concentration of ions (cations and anions) in solution is about 20 mM to about 70 mM, or about 30 mM to about 60 mM. In any of these embodiments, the total osmolarity is less than about 400 mOsm/L or 350 mOsm/L, and is preferably close to isotonic, e.g. 250-350 mOsm/L. In some embodiments, the formulation is hypotonic. For example, in such embodiments, the osmolarity of the formulation is less than about 250 mOsm/L. In other embodiments, the formulation hypertonic. Thus, in such embodiments, the total osmolarity of the formulation is greater than about 350 mOsm/L.

In any of the formulations described herein, in some embodiments, an anti-sclerostin antibody in the formulation can comprise mature heavy and/or light chain variable regions of any of antibodies Ab-A, Ab-B, Ab-C, Ab-D, Ab-2, Ab-3, Ab-4, Ab-5, Ab-6, Ab-7, Ab-8, Ab-9, Ab-10, Ab-11, Ab-12, Ab-15, Ab-16, Ab-17, Ab-19, Ab-21, Ab-23 or Ab-24. Thus, in specific embodiments, the antibody comprises the amino acid sequences of: SEQ ID NO: 14 (Ab-1 heavy chain variable region), and/or SEQ ID NO: 12 (Ab-1 light chain variable region); or SEQ ID NO: 68 (Ab-15 heavy chain variable region), and/or SEQ ID NO: 66 (Ab-15 light chain variable region); or SEQ ID NO: 86 (Ab-5 heavy chain variable region), and/or SEQ ID NO: 84 (Ab-5 light chain variable region); or SEQ ID NO: 154 (Ab-16 heavy chain variable region), and/or SEQ ID NO: 152 (Ab-16 light chain variable region); or SEQ ID NO: 182 (Ab-14 heavy chain variable region) and/or SEQ ID NO: 180 (Ab-14 light chain variable region); or SEQ ID NO: 208 (Ab-19 heavy chain variable region) and/or SEQ ID NO: 207 (Ab-19 light chain variable region); or SEQ ID NO: 216 (Ab-20 heavy chain variable region) and/or SEQ ID NO: 214 (Ab-20 light chain variable region); or SEQ ID NO: 220 (Ab-23 heavy chain variable region) and/or SEQ ID NO: 218 (Ab-23 light chain variable region); or SEQ ID NO: 238 (Ab-22 heavy chain variable region) and/or SEQ ID NO: 236 (Ab-22 light chain variable region). In some embodiments, the antibody comprises the mature heavy and/or light chains of any of antibodies Ab-A, Ab-B, Ab-C, Ab-D, Ab-2, Ab-3, Ab-4, Ab-5, Ab-6, Ab-7, Ab-8, Ab-9, Ab-10, Ab-11, Ab-12, Ab-15, Ab-16, Ab-19, Ab-23 or Ab-24. In some embodiments, the antibody comprises amino acid sequences obtainable by expressing in mammalian host cells the cDNA encoding the heavy and/or light chain, or alternatively the heavy and/or light chain variable region, of any of antibodies Ab-A, Ab-B, Ab-C, Ab-D, Ab-2, Ab-3, Ab-4, Ab-5, Ab-6, Ab-7, Ab-8, Ab-9, Ab-10, Ab-11, Ab-12, Ab-15, Ab-16, Ab-19, Ab-23 or Ab-24, as described herein.

In any of the formulations described herein, in some embodiments, the anti-sclerostin antibody comprises the CDRs, or the mature heavy and light chain variable regions, or the mature heavy and light chains, of any of Ab-4 or Ab-5; Ab-13 or Ab-14; or Ab-19, Ab-20 or Ab-23. In any of the formulations described herein, in some embodiments, the antibody binds to sclerostin of SEQ ID NO: 1 with a $K_D$ of $10^{-7}$ or less (lower numbers meaning higher binding affinity).

In any of the formulations described herein, in some embodiments, the antibody in the formulation is present at a concentration of at least 120 mg/mL, or at least 140 mg/mL. In any of the formulations described herein, in some embodiments, the absolute viscosity of the formulation is about 8 cP or less, or about 6 cP or less. In alternative embodiments, the antibody in the formulation is present at a concentration of about 70 mg/mL to about 130 mg/mL, wherein the formulation has an absolute viscosity of about 10 cP or less.

In some embodiments, any of the formulations described herein further comprises a polyol such as sucrose, for example, in an amount ranging from about 4% w/v to about 6%. In some embodiments, the formulation comprises about 9% sucrose. In some embodiments, any of the formulations described herein optionally comprises other pharmaceutically acceptable excipients, e.g. salt, buffer, amino acid, stabilizer, polyol, other tonicity agent, surfactant, bulking agent, cryoprotectant, lyoprotectant, antioxidant, metal ion, chelating agent, and/or preservative. In some embodiments, the formulation has less than 0.05% by weight surfactant.

In any of the formulations described herein, in some embodiments, the formulation has a pH ranging from about 4.5 to about 6, or about 5 to about 6, or about 5 to about 5.5. In some embodiments, the formulation has a pH of 5.2.

Also described herein are methods of using the formulations described herein to treat any disorder associated with decreased bone density, including but not limited to, achondroplasia, cleidocranial dysostosis, enchondromatosis, fibrous dysplasia, Gaucher's Disease, hypophosphatemic rickets, Marfan's syndrome, multiple hereditary exotoses, neurofibromatosis, osteogenesis imperfecta, osteopetrosis, osteopoikilosis, sclerotic lesions, pseudoarthrosis, pyogenic osteomyelitis, periodontal disease, anti-epileptic drug induced bone loss, primary or secondary hyperparathyroidism, familial hyperparathyroidism syndromes, weightlessness induced bone loss, osteoporosis in men, postmenopausal bone loss, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell anemia/disease, organ transplant related bone loss, kidney transplant related bone loss, systemic lupus erythematosus, ankylosing spondylitis, epilepsy, juvenile arthritides, thalassemia, mucopolysaccharidoses, Fabry Disease, Turner Syndrome, Down Syndrome, Klinefelter Syndrome, leprosy, Perthe's Disease, adolescent idiopathic scoliosis, infantile onset multi-system inflammatory disease, Winchester Syndrome, Menkes Disease, Wilson's Disease, ischemic bone disease (such as Legg-Calve-Perthes disease or regional migratory osteoporosis), anemic states, conditions caused by steroids, glucocorticoid-induced bone loss, heparin-induced bone loss, bone marrow disorders, scurvy, malnutrition, calcium deficiency, osteoporosis, osteopenia, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, pregnancy, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone loss associated with joint replacement, HIV associated bone loss, bone loss associated with loss of growth hormone, bone loss associated with cystic fibrosis, chemotherapy-associated bone loss, tumor-induced bone loss, cancer-related bone loss, hormone ablative bone loss, multiple myeloma, drug-induced bone loss, anorexia nervosa, disease-associated facial bone loss, disease-associated cranial bone loss, disease-associated bone loss of the jaw, disease-associated bone loss of the skull, bone loss associated with aging, facial bone loss associated with aging, cranial bone loss associated with aging, jaw bone loss associated with aging, skull bone loss associated with aging, or bone loss associated with space travel.

The formulations described herein, in some embodiments, are useful for improving outcomes in orthopedic procedures, dental procedures, implant surgery, joint replacement, bone grafting, bone cosmetic surgery and bone repair such as fracture healing, nonunion healing, delayed union healing and facial reconstruction. One or more formulations may be administered before, during and/or after the procedure, replacement, graft, surgery or repair.

Such methods may comprise administering a formulation in a therapeutically effective amount, e.g. an amount effective to improve bone density, and may further comprise administering a second therapeutic agent.

Also disclosed herein is a vial, kit or container, e.g. a pre-filled syringe or injection device, comprising a formulation described herein and optionally a label comprising instructions to use the appropriate volume or amount of the formulation necessary to achieve a dose of from about 0.5-20 mg/kg, or 0.5-10 mg/kg of patient body weight.

It should be understood that while various embodiments in the specification are presented using "comprising" language, under various circumstances, a related embodiment may also be described using "consisting of" or "consisting essentially of" language. It is to be noted that the term "a" or "an", refers to one or more, for example, "an immunoglobulin molecule," is understood to represent one or more immunoglobulin molecules. As such, the terms "a" (or "an"), "one or more," and "at least one" can be used interchangeably herein.

It should also be understood that when describing a range of values, the characteristic being described could be an individual value found within the range. For example, "a pH from about pH 4 to about pH 6," could be, but is not limited to, pH 4, 4.2, 4.6, 5.1 5.5 etc. and any value in between such values. Additionally, "a pH from about pH 4 to about pH 6," should not be construed to mean that the pH of a formulation in question varies 2 pH units in the range from pH 4 to pH 6 during storage, but rather a value may be picked in that range for the pH of the solution, and the pH remains buffered at about that pH. In some embodiments, when the term "about" is used, it means the recited number plus or minus 5%, 10%, 15% or more of that recited number. The actual variation intended is determinable from the context.

In any of the ranges described herein, the endpoints of the range are included in the range. However, the description also contemplates the same ranges in which the lower and/or the higher endpoint is excluded. Additional features and variations of the invention will be apparent to those skilled in the art from the entirety of this application, including the drawing and detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

DETAILED DESCRIPTION

Described herein are formulations comprising high concentrations of antibody that contain calcium salts and/or acetate salts or buffers to reduce viscosity, methods of using these formulations, and containers or kits comprising these formulations.

I. Antibodies in the Formulation

In some embodiments, the anti-sclerostin antibody in the formulation is present at a concentration of at least about 70 mg/ml, about 71 mg/ml, about 72 mg/ml, about 73 mg/ml, about 74 mg/ml, about 75 mg/ml, about 76 mg/ml, about 77 mg/ml, about 78 mg/ml, about 79 mg/ml, about 80 mg/ml, about 81 mg/ml, about 82 mg/ml, about 83 mg/ml, about 84 mg/ml, about 85 mg/ml, about 86 mg/ml, about 87 mg/ml, about 88 mg/ml, about 89 mg/ml, about 90 mg/ml, about 91 mg/ml, about 92 mg/ml, about 93 mg/ml, about 94 mg/ml, about 95 mg/ml, about 96 mg/ml, about 97 mg/ml, about 98 mg/ml, about 99 mg/ml, about 100 mg/ml, about 101 mg/ml, about 102 mg/ml, about 103 mg/ml, about 104 mg/ml, about 105 mg/ml, about 106 mg/ml, about 107 mg/ml, about 108 mg/ml, about 109 mg/ml, about 110 mg/ml, about 111 mg/ml, about 112 mg/ml, about 113 mg/ml, about 114 mg/ml, about 115 mg/ml, about 116 mg/ml, about 117 mg/ml, about 118 mg/ml, about 119 mg/ml, about 120 mg/ml, about 121 mg/ml, about 122 mg/ml, about 123 mg/ml, about 124 mg/ml, about 125 mg/ml, about 126 mg/ml, about 127 mg/ml, about 128 mg/ml, about 129 mg/ml, about 130 mg/ml, about 131 mg/ml, about 132 mg/ml, about 132 mg/ml, about 133 mg/ml, about 134 mg/ml, about 135 mg/ml, about 136 mg/ml, about 137 mg/ml, about 138 mg/ml, about 139 mg/ml, about 140 mg/ml, about 141 mg/ml, about 142 mg/ml, about 143 mg/ml, about 144 mg/ml, about 145 mg/ml, about 146 mg/ml, about 147 mg/ml, about 148 mg/ml, about 149 mg/ml, about 150 mg/ml, about 151 mg/ml, about 152 mg/ml, about 153 mg/ml, about 154 mg/ml, about 155 mg/ml, about 156 mg/ml, about 157 mg/ml, about 158 mg/ml, about 159 mg/ml, or about 160 mg/ml, and may range up to, e.g., about 300 mg/ml, about 290 mg/ml, about 280 mg/ml, about 270 mg/ml, about 260 mg/ml, about 250 mg/ml, about 240 mg/ml, about 230 mg/ml, about 220 mg/ml, about 210 mg/ml, about 200 mg/ml, about 190 mg/ml, about 180 mg/ml, or about 170 mg/ml. Any range featuring a combination of the foregoing endpoints is contemplated, including but not limited to: about 70 mg/ml to about 250 mg/ml, about 70 mg/ml to about 200 mg/ml, about 70 mg/ml to about 160 mg/ml, about 100 mg/ml to about 250 mg/ml, about 100 mg/1 to about 200 mg/ml, or about 100 mg/ml to about 180 mg/ml.

Antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23 and Ab-24 were previously described in U.S. Patent Application Publication No. 2007/0110747, the disclosure of which including sequence listing is incorporated herein by reference in its entirety.

The anti-sclerostin antibodies described herein bind to sclerostin of SEQ ID NO: 1 with a $K_D$ of $10^{-6}$ or less, or $10^{-7}$ or less, or $10^{-8}$ or less, or 10 or less (lower numbers meaning higher binding affinity). Affinity can be determined by any means known in the art, including via Biacore technology.

In some exemplary embodiments, the antibody comprises the heavy and/or light chain of any of antibodies Ab-A, Ab-B, Ab-C, Ab-D, Ab-2, Ab-3, Ab-4, Ab-5, Ab-6, Ab-7, Ab-8, Ab-9, Ab-10, Ab-11, Ab-12, Ab-15, Ab-16, Ab-19, Ab-23 or Ab-24. The amino acid sequences of the mature full length light chain of antibodies Ab-A, Ab-B, Ab-C, Ab-D, Ab-2, Ab-3, Ab-4, Ab-5, Ab-6, Ab-7, Ab-8, Ab-9, Ab-10, Ab-11, Ab-12, Ab-15, Ab-16, Ab-17, Ab-19, Ab-23 and Ab-24, including the constant region, are set forth in SEQ ID NOs: 8, 22, 32, 42, 52, 62, 80, 88, 98, 108, 118, 128, 138, 148, 166, 176, 184, 70, 210 222, and 246, respectively. The amino acid sequences of the mature full length heavy chain of antibodies Ab-A, Ab-B, Ab-C, Ab-D, Ab-2, Ab-3, Ab-4, Ab-5, Ab-6, Ab-7, Ab-8, Ab-9, Ab-10, Ab-11, Ab-12, Ab-15, Ab-16, Ab-19, Ab-23 and Ab-24, including the constant region, are set forth in SEQ ID NOs: 10, 24, 34, 44, 54, 64, 82, 90, 100, 110, 120, 130, 140, 150, 168, 178, 186, 72, 224, and 248.

Corresponding cDNA sequences encoding the full length light chain of antibodies Ab-A, Ab-B, Ab-C, Ab-D, Ab-2, Ab-3, Ab-4, Ab-5, Ab-6, Ab-7, Ab-8, Ab-9, Ab-10, Ab-11, Ab-12, Ab-15, Ab-16, Ab-19, Ab-23 and Ab-24, including the constant region, are set forth in SEQ ID NOs: 7, 21, 31, 41, 51, 61, 79, 87, 97, 107, 117, 127, 137, 147, 165, 175, 183, 69, 209, 221 and 245, respectively. Corresponding cDNA sequences encoding the full length heavy chain, including the constant region of antibodies Ab-A, Ab-B, Ab-C, Ab-D, Ab-2, Ab-3, Ab-4, Ab-5, Ab-6, Ab-7, Ab-8, Ab-9, Ab-10, Ab-11, Ab-12, Ab-15, Ab-16, Ab-19, Ab-23 and Ab-24, are set forth in SEQ ID NOs: 9, 23, 33, 43, 53, 63, 81, 89, 99, 109, 119, 129, 139, 149, 167, 177, 185, 71, 211, 223, and 247, respectively.

In other exemplary embodiments, the antibody comprises the heavy and/or light chain variable region of any of antibodies Ab-A, Ab-B, Ab-C, Ab-D, Ab-2, Ab-3, Ab-4, Ab-5, Ab-6, Ab-7, Ab-8, Ab-9, Ab-10, Ab-11, Ab-12, Ab-15, Ab-16, Ab-17, Ab-19, Ab-21, Ab-23 or Ab-24. For example, the antibody comprises SEQ ID NO: 14 (Ab-1 heavy chain variable region), and/or SEQ ID NO: 12 (Ab-1 light chain variable region); SEQ ID NO: 68 (Ab-15 heavy chain variable region), and/or SEQ ID NO: 66 (Ab-15 light chain variable region); or SEQ ID NO: 86 (Ab-5 heavy chain variable region), and/or SEQ ID NO: 84 (Ab-5 light chain variable region); or SEQ ID NO: 154 (Ab-16 heavy chain variable region), and/or SEQ ID NO: 152 (Ab-16 light chain variable region); or SEQ ID NO: 182 (Ab-14 heavy chain variable region) and/or SEQ ID NO: 180 (Ab-14 light chain variable region); or SEQ ID NO: 208 (Ab-19 heavy chain variable region) and/or SEQ ID NO: 207 (Ab-19 light chain variable region); or SEQ ID NO: 216 (Ab-20 heavy chain variable region) and/or SEQ ID NO: 214 (Ab-20 light chain variable region); or SEQ ID NO: 220 (Ab-23 heavy chain variable region) and/or SEQ ID NO: 218 (Ab-23 light chain variable region); or SEQ ID NO: 238 (Ab-22 heavy chain variable region) and/or SEQ ID NO: 236 (Ab-22 light chain variable region).

In some embodiments, the antibody comprises the CDRs set forth in SEQ ID NOs: 1-5 (Ab-A and Ab-1 CDRs), or 15-20 (Ab-B CDRs), or 25-30 (Ab-C CDRs), or 35-40 (Ab-D CDRs), or 45-50 (Ab-2 CDRs), or 55-60 (Ab-3 and Ab-15 CDRs), or 73-78 (Ab-4 and Ab-5 CDRs), or 91-96 (Ab-6 CDRs), or 101-106 (Ab-7 CDRs), or 111-116 (Ab-8 CDRs), or 121-126 (Ab-9 CDRs), or 131-136 (Ab-10 CDRs), or 141-146 (Ab-11 and Ab-16 CDRs), or 159-164 (Ab-12 CDRs), or 169-174 (Ab-13 and Ab-14 CDRs), or 187-192 (Ab-17 and Ab-18 CDRs), or 201-206 (Ab-19, Ab-20 and Ab-23 CDRs), or 225-229 (Ab-21 and Ab-22 CDRs), or 239-244 (Ab-24 CDRs).

In some embodiments, the antibody comprises amino acid sequences obtainable by expressing in mammalian host cells the cDNA encoding the heavy and/or light chain, or alternatively the heavy and/or light chain variable region, of any of antibodies Ab-A, Ab-B, Ab-C, Ab-D, Ab-2, Ab-3, Ab-4, Ab-5, Ab-6, Ab-7, Ab-8, Ab-9, Ab-10, Ab-11, Ab-12, Ab-15, Ab-16, Ab-19, Ab-23 or Ab-24, as described herein. In any of the formulations described herein, in some embodiments, the antibody is a tetrameric immunoglobulin consisting of two heavy chains and two light chains.

In some embodiments, the antibody comprises the CDRs of any of antibodies Ab-A, Ab-B, Ab-C, Ab-D, Ab-2, Ab-3, Ab-4, Ab-5, Ab-6, Ab-7, Ab-8, Ab-9, Ab-10, Ab-11, Ab-12, Ab-15, Ab-16, Ab-19, Ab-23 or Ab-24, and comprises a heavy and/or light chain comprising an amino acid sequence at least 75%, 80%, 85%, 90%, 95%, 96%, 97%, 98% or 99% identical to the heavy and/or light chain of antibody Ab-A, Ab-B, Ab-C, Ab-D, Ab-2, Ab-3, Ab-4, Ab-5, Ab-6, Ab-7, Ab-8, Ab-9, Ab-10, Ab-11, Ab-12, Ab-15, Ab-16, Ab-19, Ab-23 or Ab-24, respectively. In some embodiments, the antibody comprises the CDRs of any of antibodies Ab-A, Ab-B, Ab-C, Ab-D, Ab-2, Ab-3, Ab-4, Ab-5, Ab-6, Ab-7, Ab-8, Ab-9, Ab-10, Ab-11, Ab-12, Ab-15, Ab-16, Ab-19, Ab-23 or Ab-24, and comprises a heavy and/or light chain comprising an amino acid sequence at least 75%, 80%, 85%, 90%, 95%, 96%, 97%, 98% or 99% identical to the heavy and/or light chain variable region of antibody Ab-A, Ab-B, Ab-C, Ab-D, Ab-2, Ab-3, Ab-4, Ab-5, Ab-6, Ab-7, Ab-8, Ab-9, Ab-10, Ab-11, Ab-12, Ab-15, Ab-16, Ab-19, Ab-23 or Ab-24, respectively.

In some embodiments, the antibody:

1) retains any one, two, three, four, five, or six of CDRH1, CDRH2, CDRH3, CDRL1, CDRL2 and/or CDRL3 of any of antibodies Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23 or Ab-24, optionally including one or two mutations in such CDR(s), 2) retains all of CDRH1, CDRH2, CDRH3, or the heavy chain variable region of, any of antibody Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23 or Ab-24, optionally including one or two mutations in such CDR(s), 3) retains all of CDRL1, CDRL2, CDRL3, or the light chain variable region of, any of antibody Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23 or Ab-24, optionally including one or two mutations in such CDR(s), 4) binds to the same epitope of sclerostin as antibody Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23 or Ab-24, e.g. as determined through X-ray crystallography, or an amino acid within a loop formed by amino acids 86-111 of SEQ ID NO: 249; and/or 5) competes with antibody Ab-A, Ab-B, Ab-C, Ab-D, Ab-1, Ab-2, Ab-3, Ab-4, Ab-5, Ab-6, Ab-7, Ab-8, Ab-9, Ab-10, Ab-11, Ab-12, Ab-13, Ab-14, Ab-15, Ab-16, Ab-17, Ab-18, Ab-19, Ab-20, Ab-21, Ab-22, Ab-23 or Ab-24 for binding to sclerostin by more than about 75%, more than about 80%, or more than about 81%, 82%, 83%, 84%, 85%, 86%, 87%, 88%, 89%, 90%, 91%, 92%, 93%, 94% or 95%.

In some embodiments, the antibody comprises all three light chain CDRs, the mature light chain variable region, all three heavy chain CDRs, the mature heavy chain variable region, all six CDRs, or both the mature light chain and the mature heavy chain variable region. In some exemplary embodiments, two light chain CDRs from an antibody may be combined with a third light chain CDR from a different antibody. Alternatively, a CDRL1 from one antibody can be combined with a CDRL2 from a different antibody and a CDRL3 from yet another antibody, particularly where the CDRs are highly homologous. Similarly, two heavy chain CDRs from an antibody may be combined with a third heavy chain CDR from a different antibody; or a CDRH1 from one antibody can be combined with a CDRH2 from a different antibody and a CDRH3 from yet another antibody, particularly where the CDRs are highly homologous.

The term "antibody" refers to an intact antibody or a binding fragment thereof. An antibody may comprise a complete antibody molecule (including polyclonal, monoclonal, chimeric, humanized, or human versions having full length heavy and/or light chains), or comprise an antigen binding fragment thereof. Antibody fragments include F(ab')$_2$, Fab, Fab', Fv, Fc, and Fd fragments, and can be incorporated into single domain antibodies, single-chain antibodies, maxibodies, minibodies, intrabodies, diabodies, triabodies, tetrabodies, v-NAR and bis-scFv (see, e.g., Hollinger and Hudson, Nature Biotechnology, 23(9):1126-1136 (2005)).

An "isolated" antibody refers to an antibody, as that term is defined herein, that has been identified and separated from a component of its natural environment. Contaminant components of its natural environment are materials that would interfere with diagnostic or therapeutic uses for the antibody, and may include enzymes, hormones, and other proteinaceous or nonproteinaceous solutes. In certain embodiments, the antibody will be purified (1) to greater than 95% by weight of antibody, and most preferably more than 99% by weight, (2) to a degree sufficient to obtain at least 15 residues of N-terminal or internal amino acid sequence, or (3) to homogeneity by SDS-PAGE under reducing or nonreducing conditions using Coomassie blue or, preferably, silver stain. Isolated naturally occurring antibody includes the antibody in situ within recombinant cells since at least one component of the antibody's natural environment will not be present. Ordinarily, however, isolated antibody will be prepared by at least one purification step.

An "immunoglobulin" or "native antibody" is a tetrameric glycoprotein. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a "variable" ("V") region of about 100 to 110 or more amino acids primarily responsible for antigen recognition. The carboxy-terminal portion of each chain defines a constant region primarily responsible for effector function. Immunoglobulins can be assigned to different classes depending on the amino acid sequence of the constant domain of their heavy chains. Heavy chains are classified as mu (μ), delta (Δ), gamma (γ), alpha (α), and epsilon (ε), and define the antibody's isotype as IgM, IgD, IgG, IgA, and IgE, respectively. Several of these may be further divided into subclasses or isotypes, e.g. IgG1, IgG2, IgG3, IgG4, IgA1 and IgA2. Different isotypes have different effector functions; for example, IgG1 and IgG3 isotypes have antibody-dependent cellular cytotoxicity (ADCC) activity. Human light chains are classified as kappa (κ) and lambda (λ) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)).

Allotypes are variations in antibody sequence, often in the constant region, that can be immunogenic and are encoded by specific alleles in humans. Allotypes have been identified for five of the human IGHC genes, the IGHG1, IGHG2, IGHG3, IGHA2 and IGHE genes, and are designated as G1m, G2m, G3m, A2m, and Em allotypes, respectively. At least 18 Gm allotypes are known: nG1m(1), nG1m(2), G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g1, c5, u, v, g5). There are two A2m allotypes A2m(1) and A2m(2).

The term "hypervariable" region refers to amino acid residues from a complementarity determining region or CDR (i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5$^{th}$ Ed. Public Health Service, National Institutes of Health, Bethesda, Md. (1991)). Even a single CDR may recognize and bind antigen, although with a lower affinity than the entire antigen binding site containing all of the CDRs.

An alternative definition of residues from a hypervariable "loop" is described by Chothia et al., *J. Mol. Biol.* 196: 901-917 (1987) as residues 26-32 (L1), 50-52 (L2) and 91-96 (L3) in the light chain variable domain and 26-32 (H1), 53-55 (H2) and 96-101 (H3) in the heavy chain variable domain.

"Framework" or FR residues are those variable region residues other than the hypervariable region residues.

"Antibody fragments" comprise a portion of an intact immunoglobulin, preferably an antigen binding or variable region of the intact antibody, and include multispecific (bispecific, trispecific, etc.) antibodies formed from antibody fragments. Fragments of immunoglobulins may be produced by recombinant DNA techniques or by enzymatic or chemical cleavage of intact antibodies.

Nonlimiting examples of antibody fragments include Fab, Fab', F(ab')$_2$, Fv (variable region), domain antibodies (dAb, containing a VH domain) (Ward et al., Nature 341:544-546, 1989), complementarity determining region (CDR) fragments, single-chain antibodies (scFv, containing VH and VL domains on a single polypeptide chain) (Bird et al., Science 242:423-426, 1988, and Huston et al., Proc. Natl. Acad. Sci. USA 85:5879-5883, 1988, optionally including a polypeptide linker; and optionally multispecific, Gruber et al., J. Immunol. 152: 5368 (1994)), single chain antibody fragments, diabodies (VH and VL domains on a single polypeptide chain that pair with complementary VL and VH domains of another chain) (EP 404,097; WO 93/11161; and Hollinger et al., Proc. Natl. Acad. Sci. USA, 90:6444-6448 (1993)), triabodies, tetrabodies, minibodies (scFv fused to CH3 via a peptide linker (hingeless) or via an IgG hinge) (Olafsen, et al., Protein Eng Des Sel. 2004 April; 17(4):315-23), linear antibodies (tandem Fd segments (VH-CH1-VH-CH1) (Zapata et al., Protein Eng., 8(10):1057-1062 (1995)); chelating recombinant antibodies (crAb, which can bind to two adjacent epitopes on the sane antigen) (Neri et al., J Mol Biol. 246: 367-73, 1995), bibodies (bispecific Fab-scFv) or tribodies (trispecific Fab-(scFv)(2)) (Schoonjans et al., J Immunol. 165:7050-57, 2000; Willems et al., J Chromatogr B Analyt Technol Biomed Life Sci. 786:161-76, 2003), intrabodies (Biocca, et al., EMBO J. 9:101-108, 1990; Colby et al., Proc Natl Acad Sci USA. 101:17616-21, 2004) which may also comprise cell signal sequences which retain or direct the antibody intracellularly (Mhashilkar et al, EMBO J 14:1542-51, 1995; Wheeler et al., FASEB J. 17:1733-5, 2003), transbodies (cell-permeable antibodies containing a protein transduction domain (PTD) fused to scFv (Heng et al., Med Hypotheses. 64:1105-8, 2005), nanobodies (approximately 15 kDa variable domain of the heavy chain) (Cortez-Retamozo et al., Cancer Research 64:2853-57, 2004), small modular immunopharmaceuticals (SMIPs) (WO03/041600, U.S. Patent publication 20030133939 and US Patent Publication 20030118592), an antigen-binding-domain immunoglobulin fusion protein, a camelized antibody (in which VH recombines with a constant region that contains hinge, CH1, CH2 and CH3 domains) (Desmyter et al., J. Biol. Chem. 276:26285-90, 2001; Ewert et al., Biochemistry 41:3628-36, 2002; U.S. Patent Publication Nos. 20050136049 and 20050037421), a VHH containing antibody, heavy chain antibodies (HCAbs, homodimers of two heavy chains having the structure H2L2), or variants or derivatives thereof, and polypeptides that contain at least a portion of an immunoglobulin that is sufficient to confer specific antigen binding to the polypeptide, such as a CDR sequence, as long as the antibody retains the desired biological activity.

The term "variant" when used in connection with antibodies refers to a polypeptide sequence of an antibody that contains at least one amino acid substitution, deletion, or insertion in the variable region or the portion equivalent to the variable region, provided that the variant retains the desired binding affinity or biological activity. In addition, the antibodies as described herein may have amino acid modifications in the constant region to modify effector function of the antibody, including half-life or clearance, ADCC and/or CDC activity. Such modifications can enhance pharmacokinetics or enhance the effectiveness of the antibody in treating cancer, for example. See Shields et al., J. Biol. Chem., 276(9): 6591-6604 (2001), incorporated by reference herein in its entirety. In the case of IgG1, modifications to the constant region, particularly the hinge or CH2 region, may increase or decrease effector function, including ADCC and/or CDC activity. In other embodiments, an IgG2 constant region is modified to decrease antibody-antigen aggregate formation. In the case of IgG4, modifications to the constant region, particularly the hinge region, may reduce the formation of half-antibodies.

The term "modification" when used in connection with antibodies or polypeptides described herein, includes but is not limited to, one or more amino acid change (including substitutions, insertions or deletions); chemical modifications that do not interfere with hepcidin-binding activity; covalent modification by conjugation to therapeutic or diagnostic agents; labeling (e.g., with radionuclides or various enzymes); covalent polymer attachment such as pegylation (derivatization with polyethylene glycol) and insertion or substitution by chemical synthesis of non-natural amino acids. In some embodiments, modified polypeptides (including antibodies) of the invention will retain the binding properties of unmodified molecules of the invention.

The term "derivative" when used in connection with antibodies or polypeptides of the invention refers to antibodies or polypeptides that are covalently modified by conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids. In some embodiments, derivatives of the invention will retain the binding properties of underivatized molecules of the invention.

Methods for making bispecific or other multispecific antibodies are known in the art and include chemical cross-linking, use of leucine zippers [Kostelny et al., J. Immunol. 148:1547-1553, 1992]; diabody technology [Hollinger et al., Proc. Natl. Acad. Sci. USA 90:6444-48, 1993]; scFv dimers [Gruber et al., J. Immunol. 152: 5368, 1994], linear antibodies [Zapata et al., Protein Eng. 8:1057-62, 1995]; and chelating recombinant antibodies [Neri et al., J Mol Biol. 246:367-73, 1995].

Proteins and non-protein agents may be conjugated to the antibodies by methods that are known in the art. Conjugation methods include direct linkage, linkage via covalently attached linkers, and specific binding pair members (e.g., avidin-biotin). Such methods include, for example, that described by Greenfield et al., Cancer Research 50, 6600-6607 (1990) for the conjugation of doxorubicin and those described by Arnon et al., Adv. Exp. Med. Biol. 303, 79-90 (1991) and by Kiseleva et al., Mol. Biol. (USSR) 25, 508-514 (1991) for the conjugation of platinum compounds.

In some embodiments, antibodies and antibody fragments described herein are obtained, for example, from naturally-occurring antibodies, or Fab or scFv phage display libraries. The phrase "humanized antibody" refers to an antibody derived from a sequence of a non-human antibody, typically a rodent monoclonal antibody, which comprises modifications that render the sequence more human-like. Alternatively, a humanized antibody may be derived from a chimeric antibody.

Antibody fragments include domain antibody (dAb) fragment (Ward et al., Nature 341:544-546, 1989) which consists of a $V_H$ domain, "linear antibodies" comprise a pair of tandem Fd segments ($V_H$-$C_H$1-$V_H$-$C_H$1) which form a pair of antigen binding regions. Linear antibodies can be bispecific or monospecific (Zapata et al. Protein Eng. 8:1057-62 (1995)); "minibody" consisting of scFv fused to CH3 via a peptide linker (hingeless) or via an IgG hinge has been described in Olafsen, et al., Protein Eng Des Sel. 2004 April; 17(4):315-23; "maxibody" refers to bivalent scFvs covalently attached to the Fc region of an immunoglobulin, see, for example, Fredericks et al, Protein Engineering, Design & Selection, 17:95-106 (2004) and Powers et al., Journal of Immunological Methods, 251:123-135 (2001); heavy-chain antibodies, e.g. the $VH_H$ domain, or $H_2L_2$ (referred to as "heavy-chain antibodies" or "HCAbs"); or camelized $V_{HH}$ (See, e.g., Reichman, et al., J Immunol Methods 1999, 231:25-38, Desmyter et al., *J. Biol. Chem.* 276:26285-90, 2001, Ewert et al., *Biochemistry* 41:3628-36, 2002; nanobody (Cortez-Retamozo et al., *Cancer Research* 64:2853-57, 2004); intrabodies are single chain antibodies which demonstrate intracellular expression and can manipulate intracellular protein function (Biocca, et al., *EMBO J.* 9:101-108, 1990; Colby et al., *Proc Natl Acad Sci USA.* 101:17616-21, 2004, Mhashilkar et al, *EMBO J* 14: 1542-51, 1995, Wheeler et al. (*FASEB J.* 17:1733-5. 2003); transbodies are cell-permeable antibodies in which a protein transduction domains (PTD) is fused with single chain variable fragment (scFv) antibodies Heng et al., (*Med Hypotheses.* 64:1105-8, 2005); SMIPs or binding domain immunoglobulin fusion proteins specific for target protein are single-chain polypeptides comprising antigen binding domains fused to immunoglobulin domains necessary to carry out antibody effector functions. See e.g., WO03/041600, U.S. Patent publication 20030133939 and US Patent Publication 20030118592.

II. Calcium and Acetate Salts or Buffers

It has been found that adding relatively low concentrations of calcium acetate to formulations of a selected antibody reduces the viscosity of the formulation. The term "viscosity" as used herein refers to "absolute viscosity." Absolute viscosity, sometimes called dynamic or simple viscosity, is the product of kinematic viscosity and fluid density: Absolute Viscosity=Kinematic Viscosity x Density. The dimension of kinematic viscosity is $L^2/T$ where L is a length and T is a time. Commonly, kinematic viscosity is expressed in centistokes (cSt). The SI unit of kinematic viscosity is $mm^2/s$, which is 1 cSt. Absolute viscosity is expressed in units of centipoise (cP). The SI unit of absolute viscosity is the millipascal-second (mPa-s), where 1 cP=1 mPa-s.

Such viscosity measurements may be made hours (e.g., 1-23 hours), days (e.g., 1-10 days), weeks (e.g., 1-5 weeks), or months (e.g., 1-12 months), or years (e.g., 1-2 years, 1-3 years) after the addition of a viscosity reducing agent to an antibody formulation. Viscosity measurements may be made at a storage or administration temperature, e.g. 2-8° C. or 25° C. (room temperature). In some embodiments, absolute viscosity of the liquid or reconstituted liquid formulation at the storage and/or administration temperature is 15 cP or less, or 14, 13, 12, 11, 10, 9, 8, 7, 6, 5, or 4 cP or less.

In some embodiments, the viscosity of the protein formulation is measured prior to and after the addition of the calcium salt, and/or acetate salt (and/or buffer). Methods of measuring viscosity are well known in the art and include, for example, using a capillary viscometer, or a cone-plate rheometer. Any methods may be used provided the same method is used to compare the test and reference formulations.

The viscosity of an antibody formulation can be reduced by the addition of a calcium salt, and/or an acetate salt (and/or buffer) to the formulation. Viscosity of an antibody formulation can be reduced by about 5%, about 10%, about 15%, about 20%, about 25%, about 30%, about 35%, about 40%, about 45%, about 50%, about 55%, about 60%, about 65%, about 70%, about 75%, about 80%, about 85%, and about 90% compared to the viscosity of a comparable antibody formulation lacking the calcium salt, and/or acetate salt (and/or buffer).

Exemplary calcium salts include, but are not limited to, calcium acetate, calcium carbonate and calcium chloride. In some embodiments, the calcium salt is at a concentration of at least 0.5 mM, 1 mM, 2 mM, 3 mM, 4 mM, 5 mM, 6 mM, 7 mM, 8 mM, 9 mM or 10 mM. In certain embodiments, the concentration of calcium salt is not greater than 11 mM, 12 mM, 13 mM, 14 mM, 15 mM, 16 mM, 17 mM, 18 mM, 19 mM, 20 mM, 21 mM, 22 mM, 23 mM, 24 mM, or 25 mM. Any range featuring a combination of the foregoing endpoints is contemplated, including but not limited to from about 0.5 mM to about 10 mM, about 5 mM to about 10 mM, or about 5 mM to about 15 mM. In some embodiments, the calcium salt is present at a concentration that reduces viscosity of an antibody formulation by at least 30%, 40%, 50%, 60% or more compared to the same formulation of antibody lacking the acetate salt and/or buffer, or that achieves a viscosity of 10 cP or less, or 9, 8, 7, 6, or 5 cP or less. In certain embodiments, the calcium salt is added at low concentrations so as not to negatively impact the protein formulation. For example, at calcium chloride or magnesium chloride concentrations of 20 mM or greater, proteins may form a gel at low storage temperatures (e.g., 2-8° C.). Accordingly, a concentration of a calcium salt is generally selected for which the viscosity is reduced at the intended storage temperature of the reduced viscosity formulation.

In all of the ranges described herein, the concentration of cation, anion or salt described is the final concentration in the liquid or reconstituted liquid formulation that is to be administered. In any of the ranges described herein, the endpoints of the range are included in the range. However, the description also contemplates the same ranges in which the lower and/or the higher endpoint is excluded.

In some embodiments, a formulation described herein further comprises, in addition to the calcium salt, an acetate buffer at a concentration of at least 5 mM, 6 mM, 7 mM, 8 mM, 9 mM, 10 mM, or 15 mM. In some embodiments, the concentration is no greater than 10 mM, 15 mM, 20 mM, 25 mM, 30 mM, 35 mM, 40 mM, 45 mM or 50 mM. Any range featuring a combination of the foregoing endpoints is contemplated, including but not limited to from about 5 mM to about 15 mM, or from about 5 mM to about 10 mM. The buffer is preferably added to a concentration that maintains pH around 5-6 or 5-5.5 or 4.5-5.5. When the calcium salt in the formulation is calcium acetate, in some embodiments, the total concentration of acetate is about 10 mM to about 50 mM, or about 20 mM to about 40 mM.

In some aspects, the formulation comprises a total concentration of acetate that is at least about 10 mM, 15 mM, 20 mM, 25 mM, 30 mM, 35 mM, 40 mM, 45 mM, or 50 mM. In some embodiments, the concentration of acetate is no greater than about 30 mM, 35 mM, 40 mM, 45 mM, 50 mM, 55 mM, 60 mM, 65 mM, 70 mM, 75 mM, 80 mM, 85 mM, or 90 mM. Any range featuring a combination of the foregoing endpoints is contemplated, including but not limited to: about 10 mM to about 50 mM, about 20 mM to about 50 mM, about 20 mM to about 40 mM, about 30 mM to about 50 mM, or about 30 mM to about 75 mM. In some embodiments, the acetate salt or buffer comprises calcium acetate and/or sodium acetate. Alternatively, in some embodiments, the acetate salt and/or buffer is present at a concentration that reduces viscosity of an antibody formulation by at least 30%, 40%, 50%, 60% or more compared to the same formulation of antibody lacking the acetate salt and/or buffer, or that achieves a viscosity of 10 cP or less, or 9, 8, 7, 6, or 5 cP or less. By way of nonlimiting example, a solution containing 10 mM calcium acetate will have 20 mM acetate anion and 10 mM of calcium cation, because of the divalent nature of the calcium cation, while a solution containing 10 mM sodium acetate will have 10 mM sodium cation and 10 mM acetate anion.

In some embodiments, the total concentration of ions (cations and anions) in solution is at least 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, or 85 mM. In some embodiments, the total concentration of ions is no greater than about 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM or 200 mM. Any range featuring a combination of the foregoing endpoints is contemplated, including but not limited to: about 30 mM to about 60 mM, or about 30 mM to about 70 mM, or about 30 mM to about 80 mM, or about 40 mM to about 150 mM, or about 50 mM to about 150 mM. By way of nonlimiting example, a solution of 10 mM calcium acetate will have a 30 mM total concentration of ions (10 mM cations and 20 mM anions).

In any of the formulations described herein, in some embodiments, the total osmolarity is no greater than 500 mOsm/L, 450 mOsm/L, 400 mOsm/L, or 350 mOsm/L, and is preferably close to isotonic, e.g. 250-350 mOsm/L.

Other excipients known in the art or described herein can be further included in the formulation.

III. Excipients in the Formulation

Protein formulations are generally administered parenterally. When given parenterally, they must be sterile. Sterile diluents include liquids that are pharmaceutically acceptable (safe and non-toxic for administration to a human) and useful for the preparation of a liquid formulation, such as a formulation reconstituted after lyophilization. Exemplary diluents include sterile water, bacteriostatic water for injection (BWFI), a pH buffered solution (e.g. phosphate-buffered saline), sterile saline solution, Ringer's solution or dextrose solution. Diluents can include aqueous solutions of salts and/or buffers.

Excipients are additives that are included in a formulation because they either impart or enhance the stability, delivery and manufacturability of a drug product. Regardless of the reason for their inclusion, excipients are an integral component of a drug product and therefore need to be safe and well tolerated by patients. For protein drugs, the choice of excipients is particularly important because they can affect both efficacy and immunogenicity of the drug. Hence, protein formulations need to be developed with appropriate selection of excipients that afford suitable stability, safety, and marketability.

The excipients described herein are organized either by their chemical type or their functional role in formulations. Brief descriptions of the modes of stabilization are provided when discussing each excipient type. Given the teachings and guidance provided herein, those skilled in the art will readily be able to vary the amount or range of excipient without increasing viscosity to an undesirable level. Excipients may be chosen to achieve a desired osmolality (i.e., isotonic, hypotonic or hypertonic) of the final solution, pH, desired stability, resistance to aggregation or degradation or precipitation, protection under conditions of freezing, lyophilization or high temperatures, or other properties. A variety of types of excipients are known in the art. Exemplary excipients include salts, amino acids, other tonicity agents, surfactants, stabilizers, bulking agents, cryoprotectants, lyoprotectants, anti-oxidants, metal ions, chelating agents and/or preservatives.

Further, where a particular excipient is reported in a formulation by, e.g., percent (%) w/v, those skilled in the art will recognize that the equivalent molar concentration of that excipient is also contemplated.

A. Buffers

The pH range of optimal stability needs to be identified early during pre-formulation studies. Several approaches such as accelerated stability studies and calorimetric screening studies have been demonstrated to be useful in this endeavor (Remmele R. L. Jr., et al., Biochemistry, 38(16): 5241-7 (1999)). Once a formulation is finalized, the drug product must be manufactured and maintained within a predefined specification throughout its shelf-life. Hence, buffering agents are almost always employed to control pH in the formulation.

Organic acids, phosphates and Tris have been employed routinely as buffers in protein formulations (Table 1). The buffer capacity of the buffering species is maximal at a pH equal to the pKa and decreases as pH increases or decreases away from this value. Ninety percent of the buffering capacity exists within one pH unit of its pKa. Buffer capacity also increases proportionally with increasing buffer concentration.

Several factors need to be considered when choosing a buffer. First and foremost, the buffer species and its concentration need to be defined based on its pKa and the desired formulation pH. Equally important is to ensure that the buffer is compatible with the protein drug, other formulation excipients, and does not catalyze any degradation reactions. Recently, polyanionic carboxylate buffers such as citrate and succinate have been shown to form covalent adducts with the side chain residues of proteins. A third important aspect to be considered is the sensation of stinging and irritation the buffer may induce. For example, citrate is known to cause stinging upon injection (Laursen T, et al., Basic Clin Pharmacol Toxicol., 98(2): 218-21 (2006)). The potential for stinging and irritation is greater for drugs that are administered via the SC or IM routes, where the drug solution remains at the site for a relatively longer period of time than when administered by the IV route where the formulation gets diluted rapidly into the blood upon administration. For formulations that are administered by direct IV infusion, the total amount of buffer (and any other formulation component) needs to be monitored. For example, it has been reported that potassium ions administered in the form of the potassium phosphate buffer, can induce cardiovascular effects in a patient (Hollander-Rodriguez J C, et al., Am. Fam. Physician., 73(2): 283-90 (2006)).

TABLE 1

Commonly used buffering agents and their $pK_a$ values

| Buffer | $pK_a$ | Example drug product |
|---|---|---|
| Acetate | 4.8 | Neupogen, Neulasta |
| Succinate | $pK_{a1} = 4.8$, $pK_{a2} = 5.5$ | Actimmune |
| Citrate | $pK_{a1} = 3.1$, $pK_{a2} = 4.8$, $pK_{a3} = 6.4$ | Humira |
| Histidine (imidazole) | 6.0 | Xolair |
| Phosphate | $pK_{a1} = 2.15$, $pK_{a2} = 7.2$, $pK_{a3} = 12.3$ | Enbrel (liquid formulation) |
| Tris | 8.1 | Leukine |

The buffer system present in the formulation is selected to be physiologically compatible and to maintain a desired pH.

The pH buffering compound may be present in any amount suitable to maintain the pH of the formulation at a predetermined level. The pH buffering agent, e.g. acetate, may be present at a concentration between 0.1 mM and 1000 mM (1 M). In one embodiment, the pH buffering agent is at least 0.1, 0.5, 0.7, 0.8 0.9, 1.0, 1.2, 1.5, 1.7, 2, 3, 4, 5, 6, 7, 8, 9, 10, 11, 12, 13, 14, 15, 16, 17, 18, 19, 20, 30, 40, 50, 60, 70, 80, 90, 100, 200, 500, 700, or 900 mM. In another embodiment, the concentration of the pH buffering agent is between 1, 1.2, 1.5, 1.7, 2, 3, 4, 5, 6, 7, 8, 9, 10, 11, 12, 13, 14, 15, 16, 17, 18, 19, 20, 30, 40, 50, 60, 70, 80, or 90 mM and 100 mM. In still another embodiment, the concentration of the pH buffering agent is between 5, 6, 7, 8, 9, 10, 11, 12, 13, 14, 15, 16, 17, 18, 19, 20, 30, or 40 mM and 50 mM. In yet another embodiment, the concentration of the pH buffering agent is 10 mM.

Other exemplary pH buffering agents used to buffer the formulation as set out herein include, but are not limited to glycine, glutamate, succinate, phosphate, acetate, and aspartate. Amino acids such as histidine and glutamic acid can also be used as buffering agents.

B. Stabilizers and Bulking Agents

Stabilizers include a class of compounds that can serve as cryoprotectants, lyoprotectants, and glass forming agents. Cryoprotectants act to stabilize proteins during freezing or in the frozen state at low temperatures. Lyoprotectants stabilize proteins in the freeze-dried solid dosage form by preserving the native-like conformational properties of the protein during dehydration stages of freeze-drying. Glassy state properties have been classified as "strong" or "fragile" depending on their relaxation properties as a function of temperature. It is important that cryoprotectants, lyoprotectants, and glass forming agents remain in the same phase with the protein in order to impart stability. Sugars, polymers, and polyols fall into this category and can sometimes serve all three roles.

Polyols encompass a class of excipients that includes sugars, (e.g. mannitol, sucrose, sorbitol), and other polyhydric alcohols (e.g., glycerol and propylene glycol). The polymer polyethylene glycol (PEG) is included in this category. Polyols are commonly used as stabilizing excipients and/or isotonicity agents in both liquid and lyophilized parenteral protein formulations. Polyols can protect proteins from both physical and chemical degradation pathways.

Exemplary C3-C6 polyols include propylene glycol, glycerin (glycerol), threose, threitol, erythrose, erythritol, ribose, arabinose, arabitol, lyxose, maltitol, sorbitol, sorbose, glucose, mannose, mannitol, levulose, dextrose, maltose, trehalose, fructose, xylitol, inositol, galactose, xylose, fructose, sucrose, 1,2,6-hexanetriol and the like. Higher order sugars include dextran, propylene glycol, or polyethylene glycol. Reducing sugars such as fructose, maltose or galactose oxidize more readily than do non-reducing sugars. Additional examples of sugar alcohols are glucitol, maltitol, lactitol or iso-maltulose. Additional exemplary lyoprotectants include glycerin and gelatin, and the sugars mellibiose, melezitose, raffinose, mannotriose and stachyose. Examples of reducing sugars include glucose, maltose, lactose, maltulose, iso-maltulose and lactulose. Examples of non-reducing sugars include non-reducing glycosides of polyhydroxy compounds selected from sugar alcohols and other straight chain polyalcohols. Monoglycosides include compounds obtained by reduction of disaccharides such as lactose, maltose, lactulose and maltulose.

In some embodiments, the formulations described herein also comprise a stabilizer (or a combination of stabilizers) is added to the formulation. The term "stabilizer" means an excipient capable of preventing aggregation or other physical degradation, as well as chemical degradation (for example, autolysis, deamidation, oxidation, etc.) in an aqueous and solid state. Stabilizers that are conventionally employed in pharmaceutical compositions include, but are not limited to, sucrose, trehalose, mannose, maltose, lactose, glucose, raffinose, cellobiose, gentiobiose, isomaltose, arabinose, glucosamine, fructose, mannitol, sorbitol, glycine, arginine HCL, poly-hydroxy compounds, including polysaccharides such as dextran, starch, hydroxyethyl starch, cyclodextrins, N-methyl pyrollidene, cellulose and hyaluronic acid, sodium chloride, [Carpenter et al., Develop. Biol. Standard 74:225, (1991)]. In one embodiment, the stabilizer is incorporated in a concentration of about 0% to about 40% w/v. In another embodiment, the stabilizer is incorporated in a concentration of at least 0.5, 1, 2, 3, 4, 5, 6, 7, 8, 9, 10, 11, 12, 13, 14, 15, 16, 17, 18, 19, 20, 30, or 40% w/v. In another embodiment, the stabilizer is incorporated in a concentration of about 1, 2, 3, 4, 5, 6, 7, 8, 9% to about 10% w/v. In still another embodiment, the stabilizer is incorporated in a concentration of about 2% to about 6% w/v. In yet another embodiment, the stabilizer is incorporated in a concentration of about 4% w/v. In yet another embodiment, the stabilizer is incorporated in a concentration of about 6% w/v.

If desired, the formulations also include appropriate amounts of bulking and osmolarity regulating agents suitable for forming a lyophilized "cake". Bulking agents may be either crystalline (for example, mannitol, glycine) or amorphous (for example, sucrose, polymers such as dextran, polyvinylpyrolidone, carboxymethylcellulose). Other exemplary bulking agents include lactose, sorbitol, trehalose, or xylitol. In a further embodiment, the bulking agent is incorporated in a concentration of about 0% to about 10% w/v. In another embodiment, the bulking agent is incorporated in a concentration of at least 0.2, 0.5, 0.7, 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5% w/v. In a yet further embodiment the bulking agent is in a concentration of about 1, 1.5, 2.0, 2.5, 3.0, 3.5, 4.0, 4.5% to 5.0% w/v, to produce a mechanically and pharmaceutically stable cake.

C. Surfactants

Protein molecules have a high propensity to interact with surfaces making them susceptible to adsorption and denaturation at air-liquid, vial-liquid, and liquid-liquid (silicone oil) interfaces. This degradation pathway has been observed to be inversely dependent on protein concentration and result in either the formation of soluble and insoluble protein aggregates or the loss of protein from solution via adsorption to surfaces. In addition to container surface adsorption, surface-induced degradation is exacerbated with physical agitation, as would be experienced during shipping and handling of the product.

Surfactants are commonly used in protein formulations to prevent surface-induced degradation. Surfactants are amphipathic molecules with the capability of out-competing proteins for interfacial positions. Hydrophobic portions of the surfactant molecules occupy interfacial positions (e.g., air/liquid), while hydrophilic portions of the molecules remain oriented towards the bulk solvent. At sufficient concentrations (typically around the detergent's critical micellar concentration), a surface layer of surfactant molecules serve to prevent protein molecules from adsorbing at the interface. Thereby, surface-induced degradation is minimized. The most commonly used surfactants are fatty acid esters of sorbitan polyethoxylates, i.e. polysorbate 20 and polysorbate 80 (e.g., Avonex®, Neupogen®, Neulasta®). The two differ only in the length of the aliphatic chain that imparts hydrophobic character to the molecules, C-12 and C-18, respectively. Accordingly, polysorbate-80 is more surface-active and has a lower critical micellar concentration than polysorbate-20. The surfactant poloxamer 188 has also been used in several marketed liquid products such Gonal-F®, Norditropin®, and Ovidrel®.

Detergents can also affect the thermodynamic conformational stability of proteins. Here again, the effects of a given excipient will be protein specific. For example, polysorbates have been shown to reduce the stability of some proteins and increase the stability of others. Detergent destabilization of proteins can be rationalized in terms of the hydrophobic tails of the detergent molecules that can engage in specific binding with partially or wholly unfolded protein states. These types of interactions could cause a shift in the conformational equilibrium towards the more expanded protein states (i.e. increasing the exposure of hydrophobic portions of the protein molecule in complement to binding polysorbate). Alternatively, if the protein native state exhibits some hydrophobic surfaces, detergent binding to the native state may stabilize that conformation.

Another aspect of polysorbates is that they are inherently susceptible to oxidative degradation. Often, as raw materials, they contain sufficient quantities of peroxides to cause oxidation of protein residue side-chains, especially methionine. The potential for oxidative damage arising from the addition of stabilizer emphasizes the point that the lowest effective concentrations of excipients should be used in formulations. For surfactants, the effective concentration for a given protein will depend on the mechanism of stabilization. It has been postulated that if the mechanism of surfactant stabilization is related to preventing surface-denaturation the effective concentration will be around the detergent's critical micellar concentration. Conversely, if the mechanism of stabilization is associated with specific protein-detergent interactions, the effective surfactant concentration will be related to the protein concentration and the stoichiometry of the interaction (Randolph T. W., et al., *Pharm Biotechnol.*, 13:159-75 (2002)).

Surfactants may also be added in appropriate amounts to prevent surface related aggregation phenomenon during freezing and drying [Chang, B, J. Pharm. Sci. 85:1325, (1996)]. Exemplary surfactants include anionic, cationic, nonionic, zwitterionic, and amphoteric surfactants including surfactants derived from naturally-occurring amino acids. Anionic surfactants include, but are not limited to, sodium lauryl sulfate, dioctyl sodium sulfosuccinate and dioctyl sodium sulfonate, chenodeoxycholic acid, N-lauroylsarcosine sodium salt, lithium dodecyl sulfate, 1-octanesulfonic acid sodium salt, sodium cholate hydrate, sodium deoxycholate, and glycodeoxycholic acid sodium salt. Cationic surfactants include, but are not limited to, benzalkonium chloride or benzethonium chloride, cetylpyridinium chloride monohydrate, and hexadecyltrimethylammonium bromide. Zwitterionic surfactants include, but are not limited to, CHAPS, CHAPSO, SB3-10, and SB3-12. Non-ionic surfactants include, but are not limited to, digitonin, Triton X-100, Triton X-114, TWEEN-20, and TWEEN-80. In another embodiment, surfactants include lauromacrogol 400, polyoxyl 40 stearate, polyoxyethylene hydrogenated castor oil 10, 40, 50 and 60, glycerol monostearate, polysorbate 40, 60, 65 and 80, soy lecithin and other phospholipids such as DOPC, DMPG, DMPC, and DOPG; sucrose fatty acid ester, methyl cellulose and carboxymethyl cellulose.

Formulations described herein may further comprise these surfactants, either individually or as a mixture in different ratios. In one embodiment, the surfactant is incorporated in a concentration of about 0% to about 5% w/v. In another embodiment, the surfactant is incorporated in a concentration of at least 0.001, 0.002, 0.005, 0.007, 0.01, 0.05, 0.1, 0.2, 0.3, 0.4, 0.5, 0.6, 0.7, 0.7, 0.8, 0.9, 1.0, 1.5, 2.0, 2.5, 3.0, 3.5, 4.0, or 4.5% w/v. In another embodiment, the surfactant is incorporated in a concentration of about 0.001% to about 0.5% w/v. In still another embodiment, the surfactant is incorporated in a concentration of about 0.004, 0.005, 0.007, 0.01, 0.05, or 0.1% w/v to about 0.2% w/v. In yet another embodiment, the surfactant is incorporated in a concentration of about 0.01% to about 0.1% w/v.

In some embodiments, viscosity reduction is achieved with relatively little or no surfactant, e.g. 0.1% or less total surfactant, or 0.05% or less, or 0.01% or less.

D. Amino Acids

Amino acids have found versatile use in protein formulations as buffers, bulking agents, stabilizers and antioxidants. Histidine and glutamic acid are employed to buffer protein formulations in the pH range of 5.5-6.5 and 4.0-5.5 respectively. The imidazole group of histidine has a pKa=6.0 and the carboxyl group of glutamic acid side chain has a pKa of 4.3 which makes them suitable for buffering in their respective pH ranges. Glutamic acid is found in some formulations (e.g., Stemgen®). Histidine is commonly found in marketed protein formulations (e.g., Xolair®, Herceptin®, Recombinate®). It provides a good alternative to citrate, a buffer known to sting upon injection. Interestingly, histidine has also been reported to have a stabilizing effect when used at high concentrations in both liquid and lyophilized presentations (Chen B, et al., *Pharm Res.*, 20(12): 1952-60 (2003)). Histidine (up to 60 mM) was also observed to reduce the viscosity of a high concentration formulation of this antibody. However, in the same study, the authors observed increased aggregation and discoloration in histidine containing formulations during freeze-thaw studies of the antibody in stainless steel containers. The authors attributed this to an effect of iron ions leached from corrosion of steel containers. Another note of caution with histidine is that it undergoes photo-oxidation in the presence of metal ions (Tomita M, et al., *Biochemistry*, 8(12): 5149-60 (1969)). The use of methionine as an antioxidant in formulations appears promising; it has been observed to be effective against a number of oxidative stresses (Lam X M, et al., *J Pharm Sci.*, 86(11): 1250-5 (1997)).

The amino acids glycine, proline, serine and alanine stabilize proteins. Glycine is also a commonly used bulking agent in lyophilized formulations (e.g., Neumega®, Genotropin®, Humatrope®). Arginine has been shown to be an effective agent in inhibiting aggregation and has been used in both liquid and lyophilized formulations (e.g., Activase®, Avonex®, Enbrel® liquid).

E. Antioxidants

Oxidation of protein residues arises from a number of different sources. Beyond the addition of specific antioxidants, the prevention of oxidative protein damage involves the careful control of a number of factors throughout the manufacturing process and storage of the product such as atmospheric oxygen, temperature, light exposure, and chemical contamination. The most commonly used pharmaceutical antioxidants are reducing agents, oxygen/free-radical scavengers, or chelating agents. Antioxidants in therapeutic protein formulations must be water-soluble and remain active throughout the product shelf-life. Reducing agents and oxygen/free-radical scavengers work by ablating active oxygen species in solution. Chelating agents such as EDTA can be effective by binding trace metal contaminants that promote free-radical formation. For example, EDTA was utilized in the liquid formulation of acidic fibroblast growth factor to inhibit the metal ion catalyzed oxidation of cysteine residues. EDTA has been used in marketed products like Kineret® and Ontak®.

However, antioxidants themselves can induce other covalent or physical changes to the protein. A number of such cases have been reported in the literature. Reducing agents (like glutathione) can cause disruption of intramolecular disulfide linkages, which can lead to disulfide shuffling. In the presence of transition metal ions, ascorbic acid and EDTA have been shown to promote methionine oxidation in a number of proteins and peptides (Akers M J, and Defelippis M R. Peptides and Proteins as Parenteral Solutions. In: Pharmaceutical Formulation Development of Peptides and Proteins. Sven Frokjaer, Lars Hovgaard, editors. Pharmaceutical Science. Taylor and Francis, U K (1999)); Fransson J. R., *J. Pharm. Sci.* 86(9): 4046-1050 (1997); Yin J, et al., *Pharm Res.*, 21(12): 2377-83 (2004)). Sodium thiosulfate has been reported to reduce the levels of light and temperature induced methionine-oxidation in rhuMab HER2; however, the formation of a thiosulfate-protein adduct was also reported in this study (Lam X M, Yang J Y, et al., *J Pharm Sci.* 86(11): 1250-5 (1997)). Selection of an appropriate antioxidant is made according to the specific stresses and sensitivities of the protein.

F. Metal Ions

In general, transition metal ions are undesired in protein formulations because they can catalyze physical and chemical degradation reactions in proteins. However, specific metal ions are included in formulations when they are co-factors to proteins and in suspension formulations of proteins where they form coordination complexes (e.g., zinc suspension of insulin). Recently, the use of magnesium ions (10-120 mM)

has been proposed to inhibit the isomerization of aspartic acid to isoaspartic acid (WO 2004/039337).

Two examples where metal ions confer stability or increased activity in proteins are human deoxyribonuclease (rhDNase, Pulmozyme®), and Factor VIII. In the case of rhDNase, $Ca^{+2}$ ions (up to 100 mM) increased the stability of the enzyme through a specific binding site (Chen B, et al., *J Pharm Sci.*, 88(4): 477-82 (1999)). In fact, removal of calcium ions from the solution with EGTA caused an increase in deamidation and aggregation. However, this effect was observed only with $Ca^{+2}$ ions; other divalent cations—$Mg^{+2}$, $Mn^{+2}$ and $Zn^{+2}$ were observed to destabilize rhDNase. Similar effects were observed in Factor VIII. $Ca^{+2}$ and $Sr^{+2}$ ions stabilized the protein while others like $Mg^{+2}$, $Mn^{+2}$ and $Zn^{+2}$, $Cu^{+2}$ and $Fe^{+2}$ destabilized the enzyme (Fatouros, A., et al., *Int. J. Pharm.*, 155, 121-131 (1997). In a separate study with Factor VIII, a significant increase in aggregation rate was observed in the presence of $Al^{+3}$ ions (Derrick T S, et al., *J. Pharm. Sci.*, 93(10): 2549-57 (2004)). The authors note that other excipients like buffer salts are often contaminated with $Al^{+3}$ ions and illustrate the need to use excipients of appropriate quality in formulated products.

G. Preservatives

Preservatives are necessary when developing multi-use parenteral formulations that involve more than one extraction from the same container. Their primary function is to inhibit microbial growth and ensure product sterility throughout the shelf-life or term of use of the drug product. Commonly used preservatives include phenol, benzyl alcohol, meta-cresol, alkyl parabens such as methyl paraben or propyl paraben, benzalkonium chloride, and benzethonium chloride. Other examples of compounds with antimicrobial preservative activity include octadecyldimethylbenzyl ammonium chloride, hexamethonium chloride. Other types of preservatives include aromatic alcohols such as butyl alcohol, phenol, benzyl alcohol; atechol, resorcinol, cyclohexanol, 3-pentanol. Although preservatives have a long history of use, the development of protein formulations that includes preservatives can be challenging. Preservatives almost always have a destabilizing effect (aggregation) on proteins, and this has become a major factor in limiting their use in multi-dose protein formulations (Roy S, et al., *J Pharm Sci.*, 94(2): 382-96 (2005)).

Multi-use injection pen presentations include preserved formulations. For example, preserved formulations of hGH are currently available on the market. Norditropin® (liquid, Novo Nordisk), Nutropin AQ® (liquid, Genentech) & Genotropin (lyophilized—dual chamber cartridge, Pharmacia & Upjohn) contain phenol while Somatrope® (Eli Lilly) is formulated with m-cresol.

Several aspects need to be considered during the formulation development of preserved dosage forms. The effective preservative concentration in the drug product must be optimized. This requires testing a given preservative in the dosage form with concentration ranges that confer anti-microbial effectiveness without compromising protein stability. For example, three preservatives were successfully screened in the development of a liquid formulation for interleukin-1 receptor (Type I), using differential scanning calorimetry (DSC). The preservatives were rank ordered based on their impact on stability at concentrations commonly used in marketed products (Remmele R L Jr., et al., *Pharm Res.*, 15(2): 200-8 (1998)).

Some preservatives can cause injection site reactions, which is another factor that needs consideration when choosing a preservative. In clinical trials that focused on the evaluation of preservatives and buffers in Norditropin, pain perception was observed to be lower in formulations containing phenol and benzyl alcohol as compared to a formulation containing m-cresol (Kappelgaard A. M., *Horm Res.* 62 Suppl 3:98-103 (2004)). Interestingly, among the commonly used preservative, benzyl alcohol possesses anesthetic properties (Minogue S C, and Sun D A., *Anesth Analg.*, 100(3): 683-6 (2005)).

IV. Kits

As an additional aspect, the described herein are kits which comprise one or more formulations described herein packaged in a manner which facilitates their use for administration to subjects. In one embodiment, such a kit includes a formulation described herein (e.g., a composition comprising any of the antibodies described therein), packaged in a container such as a sealed bottle, vessel, single-use or multi-use vial, prefilled syringe, or prefilled injection device, optionally with a label affixed to the container or included in the package that describes use of the compound or composition in practicing the method. In one aspect, the compound or composition is packaged in a unit dosage form. The kit may further include a device suitable for administering the composition according to a specific route of administration. Preferably, the kit contains a label that describes use of an antibody described herein or formulation described herein.

V. Dosages

The dosage regimen involved in a method for treating a condition described herein will be determined by the attending physician, considering various factors which modify the action of drugs, e.g. the age, condition, body weight, sex and diet of the patient, the severity of any infection, time of administration and other clinical factors. In various aspects, the daily regimen is in the range of 0.1-50 mg of a preparation of antibody per kilogram of body weight (calculating the mass of the protein alone, without chemical modification). In some embodiments, the dosage is about 0.5 mg/kg to 20 mg/kg, or about 0.5-10 mg/kg.

The formulations are generally administered parenterally, e.g. intravenously, subcutaneously, intramuscularly, via aerosol (intrapulmonary or inhalational administration), or via depot for long-term release. In some embodiments, the formulation is administered intravenously by an initial bolus followed by a continuous infusion to maintain therapeutic circulating levels of drug product. In other embodiments, the formulation is administered as a one-time dose. Those of ordinary skill in the art will readily optimize effective dosages and administration regimens as determined by good medical practice and the clinical condition of the individual patient. The frequency of dosing will depend on the pharmacokinetic parameters of the agents and the route of administration. The optimal pharmaceutical formulation will be determined by one skilled in the art depending upon the route of administration and desired dosage. See for example, Remington's Pharmaceutical Sciences, 18th Ed. (1990, Mack Publishing Co., Easton, Pa. 18042) pages 1435-1712, the disclosure of which is hereby incorporated by reference. Such formulations may influence the physical state, stability, rate of in vivo release, and rate of in vivo clearance of the administered agents. Depending on the route of administration, a suitable dose may be calculated according to body weight, body surface area or organ size. Further refinement of the calculations necessary to determine the appropriate dosage for treatment involving each of the above mentioned formulations is routinely made by those of ordinary skill in the art without undue experimentation, especially in light of the dosage information and assays disclosed herein, as well as the pharmacokinetic data observed in the human clinical trials discussed above. Appropriate dosages may be ascertained through use of established assays for determining blood level dosages in conjunction with appropriate dose-response data. The final dosage regimen will be determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. As studies are conducted, further information will emerge regarding the appropriate dosage levels and duration of treatment for various diseases and conditions.

VI. Therapeutic Uses of the Formulation

The formulations described herein are useful for treating or preventing bone-related disorders, such as bone-related disorders associated with abnormal osteoblast or osteoclast activity. In some embodiments, the formulation is administered to a subject suffering from a bone related disorder selected from the group consisting of achondroplasia, cleidocranial dysostosis, enchondromatosis, fibrous dysplasia, Gaucher's Disease, hypophosphatemic rickets, Marfan's syndrome, multiple hereditary exotoses, neurofibromatosis, osteogenesis imperfecta, osteopetrosis, osteopoikilosis, sclerotic lesions, pseudoarthrosis, pyogenic osteomyelitis, periodontal disease, anti-epileptic drug induced bone loss, primary and secondary hyperparathyroidism, familial hyperparathyroidism syndromes, weightlessness induced bone loss, osteoporosis in men, postmenopausal bone loss, osteoarthritis, renal osteodystrophy, infiltrative disorders of bone, oral bone loss, osteonecrosis of the jaw, juvenile Paget's disease, melorheostosis, metabolic bone diseases, mastocytosis, sickle cell anemia/disease, organ transplant related bone loss, kidney transplant related bone loss, systemic lupus erythematosus, ankylosing spondylitis, epilepsy, juvenile arthritides, thalassemia, mucopolysaccharidoses, Fabry Disease, Turner Syndrome, Down Syndrome, Klinefelter Syndrome, leprosy, Perthe's Disease, adolescent idiopathic scoliosis, infantile onset multi-system inflammatory disease, Winchester Syndrome, Menkes Disease, Wilson's Disease, ischemic bone disease (such as Legg-Calve-Perthes disease and regional migratory osteoporosis), anemic states, conditions caused by steroids, glucocorticoid-induced bone loss, heparin-induced bone loss, bone marrow disorders, scurvy, malnutrition, calcium deficiency, osteoporosis, osteopenia, alcoholism, chronic liver disease, postmenopausal state, chronic inflammatory conditions, rheumatoid arthritis, inflammatory bowel disease, ulcerative colitis, inflammatory colitis, Crohn's disease, oligomenorrhea, amenorrhea, pregnancy, diabetes mellitus, hyperthyroidism, thyroid disorders, parathyroid disorders, Cushing's disease, acromegaly, hypogonadism, immobilization or disuse, reflex sympathetic dystrophy syndrome, regional osteoporosis, osteomalacia, bone loss associated with joint replacement, HIV associated bone loss, bone loss associated with loss of growth hormone, bone loss associated with cystic fibrosis, chemotherapy-associated bone loss, tumor-induced bone loss, cancer-related bone loss, hormone ablative bone loss, multiple myeloma, drug-induced bone loss, anorexia nervosa, disease-associated facial bone loss, disease-associated cranial bone loss, disease-associated bone loss of the jaw, disease-associated bone loss of the skull, bone loss associated with aging, facial bone loss associated with aging, cranial bone loss associated with aging, jaw bone loss associated with aging, skull bone loss associated with aging, and bone loss associated with space travel.

In some embodiments, the formulations described herein are useful for improving outcomes in orthopedic procedures, dental procedures, implant surgery, joint replacement, bone grafting, bone cosmetic surgery and bone repair such as fracture healing, nonunion healing, delayed union healing and facial reconstruction. One or more compositions may be administered before, during and/or after the procedure, replacement, graft, surgery or repair.

The formulation need not cure the subject of the disorder or completely protect against the onset of a bone-related disorder to achieve a beneficial biological response. The formulation may be used prophylactically, meaning to protect, in whole or in part, against a bone-related disorder or symptom thereof. The formulation also may be used therapeutically to ameliorate, in whole or in part, a bone-related disorder or symptom thereof, or to protect, in whole or in part, against further progression of a bone-related disorder or symptom thereof. Indeed, the materials and methods of the invention are particularly useful for increasing bone mineral density and maintaining the increased bone mineral density over a period of time.

One or more administrations of a formulation described herein may be carried out over a therapeutic period of, for example, about 1 month to about 12 months (e.g., about 2 months, about 3 months, about 4 months, about 5 months, about 6 months, about 7 months, about 8 months, about 9 months, about 10 months, or about 11 months). In some embodiments, a subject is administered one or more doses of the formulation to maintain bone mineral density. The term "maintain bone mineral density" as used herein means that the increased bone mineral density resulting the initial dose of the formulation does not fall more than about 1% to about 5% over the course of about 6 months, about 9 months about 1 year, about 18 months, about 2 years, or over the course of the patient's life). It will be appreciated that a patient can require alternate treatment phases for increasing bone density and maintaining bone density.

In addition, it may be advantageous to administer multiple doses of the formulation or space out the administration of doses, depending on the therapeutic regimen selected for a particular subject. The formulation can be administered periodically over a time period of one year or less (e.g., 9 months or less, 6 months or less, or 3 months or less). In this regard, the formulation can be administered to the human once every about 7 days, or 2 weeks, or 3 weeks, or 1 month, or 5 weeks, or 6 weeks, or 7 weeks, or 2 months, or 9 weeks, or 10 weeks, or 11 weeks, or 3 months, or 13 weeks, or 14 weeks, or 15 weeks, or 4 months, or 17 weeks, or 18 weeks, or 19 weeks, or 5 months, or 21 weeks, or 22 weeks, or 23 weeks, or 6 months, or 12 months.

VII. Combination Therapy

Treatment of a pathology by combining two or more agents that target the same pathogen or biochemical pathway sometimes results in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect can be synergistic (the efficacy of the combination is greater than the sum of the effects of each drug given alone). As used herein, the term "combination therapy" means the two compounds can be delivered in a simultaneous manner, e.g. concurrently, or wherein one of the compounds is administered first, followed by the second agent, e.g., sequentially. The desired result can be either a subjective relief of one or more symptoms or an objectively identifiable improvement in the recipient of the dosage.

In some embodiments, the formulation is administered along with a standard of care therapeutic for the treatment of decreased bone mineral density. As used herein, the term "standard of care" refers to a treatment that is generally accepted by clinicians for a certain type of patient diagnosed with a type of illness. In some embodiments, the standard of care therapeutic is selected from the group consisting of an anti-resorptive drug, a bone-forming agent, an estrogen receptor antagonist (including, but not limited to, raloxifene, bazedoxifene and lasofoxifene) and a drug that has a stimulatory effect on osteoclasts. In some embodiments, the anti-resorptive drug includes, but is not limited to, a bisphosphonate (including, but not limited to, alendronate, risedronate, ibandronate and zoledronate), an estrogen or estrogen analogue, a selective estrogen receptor modulator (SERM) and a calcium source, Tibolone, calcitonin, a calcitriol and hormone replacement therapy. In some embodiments, the bone-forming agent includes, but is not limited to parathyroid hormone (PTH) or a peptide fragment thereof, PTH-related protein (PTHrp), bone morphogenetic protein, osteogenin, NaF, a $PGE_2$ agonist, a statin, and a RANK ligand (RANKL). In some embodiments, the drug having a stimulatory effect on osteoclasts includes, but it not limited to, vitamin D, or a vitamin D derivative or mimic thereof.

In some embodiments, the formulation is administered to a subject when treatment of a standard of care therapeutic described herein is contraindicated.

EXAMPLES

Example 1

Calcium Acetate Reduced the Effective Viscosity of Sclerostin Antibody Formulations 10 ml of a selected anti-sclerostin antibody (75.7 mg/ml) was dialyzed against 2 liters of 10 mM Na(OAc) and 9% sucrose at 4° C. for 2 hours. A selected anti-sclerostin antibody (75.7 mg/ml) was concentrated to approximately 160 mg/ml and diluted with water to approximately 140 mg/ml and 120 mg/ml. Absorbance of the diluted samples were determined to be 120, 142 and 157 mg/ml, respectively 10 μl 1.0M $Ca(OAc)_2$ was added to 1 ml of the 120 mg/ml, 140 mg/ml and 160 mg/ml samples. Absolute viscosity, pH and osmolarity of the samples were determined (See Table 2). Absolute viscosity of the samples (500 μl) was measured using Brookfield LV-DVII cone and plate viscometer with a CPE-40 spindle with matching sample cup temperature regulated by a circulating water bath at constant 25° C.

TABLE 2

| Sample | Viscosity (cP) | pH | Osmolarity |
|---|---|---|---|
| 120 mg/ml (Control) | 18 | 5.3 | 375 |
| 120 mg/ml + 10 mM $Ca(OAc)_2$ | 8.4 | 5.4 | 398 |
| 142 mg/ml + 10 mM $Ca(OAc)_2$ | 17 | 5.4 | 450 |
| 157 mg/ml + 10 mM $Ca(OAc)_2$ | 36 | 5.4 | 610 |

Results indicated that 10 mM $Ca(OAc)_2$ spiked into a liquid composition of the selected antibody reduced viscosity by about half. This experiment is performed for each of antibodies Ab-4, Ab-5, Ab-13, Ab-14, Ab-19, Ab-20 and Ab-23.

Example 2

Formulations Adjustment 10 ml of a selected anti-sclerostin antibody (75.7 mg/ml) was dialyzed against 2 liters of 10 mM Na(OAc), 6% sucrose or 4% sucrose at 4° C. for 2 hours. Each sucrose formulation was then concentrated using Amicons to approximately 140 mg/ml then diluted with water back down to the targeted concentrations (i.e., 120 mg/ml, 140 mg/ml and 160 mg/ml). Absorbance values of the diluted samples were determined to be 124 mg/ml (4% sucrose), 119.5 mg/ml (6% sucrose), 137.5 mg/ml (4% sucrose) and 142 mg/ml (6% sucrose), respectively.

10 μl 1.0M $Ca(OAc)_2$ was added to 1 ml of the samples. Viscosity, osmolarity and pH of the samples were determined (See Table 3)

TABLE 3

| Sample | mM | Mg/mL | pH | Osmolarity | Viscosity (cP) |
|---|---|---|---|---|---|
| 120 mg/mL + 10 mM CaOAC + 4% sucrose | 10 | 124 | 5.285 | 214 | 6.2 |
| 120 mg/mL + 10 mM CaOAC + 6% sucrose | 10 | 119.5 | 5.25 | 282 | 5.7 |
| 140 mg/mL + 10 mM CaOAC + 4% sucrose | 10 | 137.5 | 5.303 | 231 | 9.5 |
| 140 mg/mL + 10 mM CaOAC + 6% sucrose | 10 | 142 | 5.307 | 294 | 11 |

The assay was repeated as follows: 10 ml of a selected anti-sclerostin antibody (75.7 mg/ml) was dialyzed against 2 liters of 10 mM Na(OAc), 6% sucrose or 4% sucrose at 4° C. for 2 hours. Each sucrose formulation was then concentrated using Amicon filter to approximately 140 mg/ml then diluted with water back down to the targeted concentrations (i.e., 70 mg/ml, 100 mg/ml and 120 mg/ml). Absorbance values of the diluted samples were determined to be 71 mg/ml (4% sucrose), 68.2 mg/ml (6% sucrose), 99.4 mg/ml (4% sucrose), 100.5 (6% sucrose), 122 mg/ml (4% sucrose) and 113 mg/ml (6% sucrose), respectively.

pH, osmolarity and viscosity of the samples were determined. See Table 4.

TABLE 4

| Sample | mM | Mg/mL | pH | Osmolarity | Viscosity (cP) |
|---|---|---|---|---|---|
| 70 mg/mL + 4% sucrose | 10 | 71 | 5.205 | 154 | 3.5 |
| 70 mg/mL + 10 mM CaOAC + 4% sucrose | 10 | 71 | 5.233 | 183 | 2.2 |
| 70 mg/mL 6% sucrose | 10 | 68.2 | 5.201 | 231 | 3.4 |
| 70 mg/mL + 10 mM CaOAC + 6% sucrose | 10 | 68.2 | 5.279 | 256 | 2.4 |
| 100 mg/mL + 4% sucrose | 10 | 99.4 | 5.265 | 165 | 8.1 |
| 100 mg/mL + 10 mM CaOAC + 4% sucrose | 10 | 99.4 | 5.288 | 191 | 4.1 |
| 100 mg/mL + 6% sucrose | 10 | 100.5 | 5.273 | 241 | 8.4 |
| 100 mg/mL + 10 mM CaOAC + 6% sucrose | 10 | 100.5 | 5.303 | 270 | 4.3 |
| 120 mg/mL + 4% sucrose | 10 | 122 | 5.295 | 177 | 15.6 |
| 120 mg/mL + 10 mM CaOAC + 4% sucrose | 10 | 122 | 5.306 | 202 | 6.9 |
| 120 mg/mL + 6% sucrose | 10 | 113 | 5.3 | 249 | 15.4 |
| 120 mg/mL + 10 mM CaOAC + 6% sucrose | 10 | 113 | 5.311 | 274 | 6.6 |

Lowering pH of $Ca(OAc)_2$ buffer to 5.2 kept all final formulation pHs between 5.25 and 5.307. The 4% sucrose formulations were below the isotonic range (250-350 mOsm/kg), but the 6% sucrose formulations were near the middle of the isotonic range.

To further assess the effect of 6% sucrose with 10 mM $Ca(OAc)_2$ in reducing viscosity, the assay above was repeated with further concentrations of anti-sclerostin antibody up to 160 mg/ml.

Samples were prepared as described above with the following concentrations: 120 mg/ml, 140 mg/ml and 160 mg/ml. 10 µl of 1.0M Ca(OAc)$_2$, pH 5.2, was added to each of the samples. pH, osmolarity and viscosity of the samples were determined. See Table 5.

TABLE 5

| Sample | mM | Mg/mL | pH | Osmolarity | Viscosity (cP) |
|---|---|---|---|---|---|
| 100 mg/mL + 10 mM CaOAC + 6% sucrose | 10 | 107 | 5.285 | 271 | 4.3 |
| 100 mg/mL + 10 mM CaOAC + 6% sucrose | 10 | 107 | 5.285 | 277 | 4.3 |
| 120 mg/mL + 10 mM CaOAC + 6% sucrose | 10 | 120 | 5.311 | 279 | 6.1 |
| 120 mg/mL + 10 mM CaOAC + 6% sucrose | 10 | 120 | 5.311 | 278 | 6 |
| 140 mg/mL + 10 mM CaOAC + 6% sucrose | 10 | 145 | 5.329 | X | 12 |
| 140 mg/mL + 10 mM CaOAC + 6% sucrose | 10 | 145 | 5.329 | 309 | 11.7 |
| 160 mg/mL + 10 mM CaOAC + 6% sucrose | 10 | 168.7 | 5.343 | X | 18.8 |
| 160 mg/mL + 10 mM CaOAC + 6% sucrose | 10 | 168.7 | 5.343 | X | 18.8 |

The above-described experiments are performed for each of antibodies Ab-4, Ab-5, Ab-13, Ab-14, Ab-19, Ab-20 and Ab-23.

Example 3

Effect of Calcium Acetate in Other High Protein Concentration Formulations

The following Example determined whether calcium acetate reduces the viscosity of formulations containing high concentration of protein other than a sclerostin antibody.

Non-sclerostin antibodies #1-#5 were determined to have a concentration of 131.6 mg/ml, 94 mg/ml, 113.2 mg/ml, 50 mg/ml and 106.3, respectively. The term "non-sclerostin antibody" as used herein means an antibody other than a sclerostin antibody described herein.

10 µl 1.0M Ca(OAc)$_2$ was added to 1 ml of the 5 samples discussed above. Viscosity, pH and osmolarity of the samples were determined (See Table 6).

TABLE 6

| Sample | Mg/mL | Viscosity (cP) |
|---|---|---|
| Non-sclerostin antibody #1 | 94 | 6.8 |
| Non-sclerostin antibody #1 + 10 mM Ca(OAc)$_2$ | 94 | 5.10 |
| Non-sclerostin antibody #2 | 135 | 9.8 |
| Non-sclerostin antibody #2 + 10 mM Ca(OAc)$_2$ | 135 | 8.3 |
| Protein #1 | 50 | 3.3 |
| Protein #1 + 10 mM Ca(OAc)$_2$ | 50 | 3.2 |
| Protein #1 | 106.3 | 16.6 |
| Protein #1 + 10 mM Ca(OAc)$_2$ | 106.3 | 15.6 |

Calcium acetate did not significantly reduce the viscosity of any of the samples.

Example 4

Effect of Non-Calcium Salts on the Viscosity of High Concentration Anti-Sclerostin Antibody Formulation The following experiment was performed to determine whether non-calcium salts would be capable of reducing the viscosity of an anti-sclerostin antibody formulation.

A selected anti-sclerostin antibody (the same as in Examples 1-2 above) was concentrated to ~130 mg/mL. 10 µl of either 1.0M (NH$_4$)$_2$SO$_4$ or 1.0M MgSO$_4$ was added to 1 ml of antibody sample. Viscosity of the control was determined to be 30 cP. MgSO$_4$ was determined to significantly reduce viscosity of the sample (MgSO$_4$+sample=16 cP). (NH$_4$)$_2$SO$_4$ did not significantly reduce viscosity of the sample.

Example 5

Effect of Other Calcium Salts on the Viscosity of High Concentration Anti-Sclerostin Antibody Formulation The following experiment was performed to determine whether calcium salts other than calcium acetate would be capable of reducing the viscosity of an anti-sclerostin antibody formulation.

A selected anti-sclerostin antibody (the same as in Examples 1-2 above) was concentrated to ~125 mg/mL. 10 µl of either 25 mM CaCl$_2$ or 25 mM MgCl$_2$ was added to 1 ml of antibody sample. Viscosity of the control was determined to be 18.5 cP. CaCl$_2$ and MgCl$_2$ were determined to significantly reduce viscosity of the sample (CaCl$_2$+sample=9 cP and MgCl$_2$+sample=8).

Example 6

Effect of Calcium Acetate on Another Anti-Sclerostin Antibody

The following experiment was performed to determine whether calcium acetate would be capable of reducing the viscosity of an anti-sclerostin antibody formulation comprising a different anti-sclerostin antibody than in Examples 1-2 above.

A selected anti-sclerostin antibody was concentrated to ~131 mg/mL. 10 µl 1.0M Ca(OAc)$_2$ was added to 1 ml of antibody sample. Viscosity of the control was determined to be 17.3 cP. Ca(OAc)$_2$ was determined to slightly reduce viscosity of the sample (15.3 cP)

Numerous modifications and variations in the practice of the invention are expected to occur to those of skill in the art upon consideration of the presently preferred embodiments thereof. Consequently, the only limitations which should be placed upon the scope of the invention are those which appear in the appended claims.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

What is claimed is:

1. A sterile liquid formulation that has an absolute viscosity of about 10 cP or less consisting essentially of: (a) an anti-sclerostin immunoglobulin at a concentration of from about 70 mg/mL to about 120 mg/mL, wherein the anti-sclerostin immunoglobulin comprises the amino acid sequences of SEQ ID NO: 86 and SEQ ID NO: 84; (b) calcium acetate at a concentration ranging from about 1 mM to about 20 mM; and (c) a polyol in an amount ranging from about 4% w/v to about 6% w/v.

2. The formulation of claim 1, that has a total osmolarity of less than about 350 mOsm/L.

3. The formulation of claim 1, wherein the immunoglobulin is present at a concentration of at least 120 mg/mL.

4. The formulation of claim 1, wherein the absolute viscosity of the formulation is about 8 cP or less.

5. The formulation of claim 4, wherein the absolute viscosity of the formulation is about 6 cP or less.

6. The formulation of claim 1, wherein the formulation has a pH ranging from about 4.5 to about 6.

7. The formulation of claim 6, wherein the formulation has a pH ranging from about 5 to about 5.5.

8. The formulation of claim 1, comprising the immunoglobulin at a concentration of 90 mg/mL.

9. The sterile liquid formulation of claim 1, wherein the polyol is sucrose.

10. A method for reducing the viscosity of a protein formulation, the method consisting essentially of:
    adding (i) calcium acetate to an anti-sclerostin immunoglobulin formulation, wherein the calcium acetate is at a concentration of between about 1 mM and about 20 mM, wherein the immunoglobulin comprises the amino acid sequences of SEQ ID NO: 86 and SEQ ID NO: 84 and is present at a concentration of from about 70 mg/mL to about 120 mg/mL and (ii) a polyol in an amount ranging from about 4% w/v to about 6% w/v, wherein the viscosity of the formulation with the calcium acetate is reduced compared to the viscosity of an immunoglobulin formulation without the calcium acetate.

11. The sterile liquid formulation of claim 10, wherein the polyol is sucrose.

12. A sterile liquid formulation that has an absolute viscosity of about 10 cP or less consisting essentially of: (a) an immunoglobulin having a heavy chain comprising the amino acid sequence of SEQ ID NO: 90 and a light chain comprising the amino acid sequence of SEQ ID NO: 88 at a concentration of from about 70 mg/mL to about 120 mg/mL; (b) calcium acetate at a concentration ranging from about 1 mM to about 20 mM; and (c) a polyol in an amount ranging from about 4% w/v to about 6% w/v.

13. The formulation of claim 12, wherein the polyol is sucrose.

14. The formulation of claim 12, comprising the immunoglobulin at a concentration of 90 mg/mL.

15. The sterile liquid formulation of claim 12, wherein the formulation consists of: (a) an antibody having a heavy chain comprising the amino acid sequence of SEQ ID NO: 90 and a light chain comprising the amino acid sequence of SEQ ID NO: 88 at a concentration of from about 70 mg/mL to about 120 mg/mL; (b) calcium acetate at a concentration of ranging from about 1 mM to about 20 mM; (c) a polyol in an amount ranging from about 4% w/v to about 6% w/v; and (d) a surfactant.

16. The sterile liquid formulation of claim 15, wherein the surfactant is polysorbate 20.

17. The sterile liquid formulation of claim 15, wherein the concentration of the surfactant is from about 0.004% to about 0.2% w/v.

18. A sterile liquid formulation consisting essentially of:
    (a) an anti-sclerostin immunoglobulin at a concentration of from about 70 mg/mL to about 120 mg/mL, wherein the immunoglobulin comprises the amino acid sequences of SEQ ID NO: 86 and SEQ ID NO: 84;
    (b) calcium acetate at a concentration ranging from about 1 mM to about 20 mM, wherein the calcium acetate reduces the absolute viscosity of the formulation by at least 50% compared to the viscosity of an immunoglobulin formulation without the calcium acetate; and
    (c) a polyol in an amount ranging from about 4% w/v to about 6% w/v.

19. The formulation of claim 18, comprising the immunoglobulin at a concentration of 90 mg/mL.

20. The sterile liquid formulation of claim 18, wherein the polyol is sucrose.

21. A method of using a therapeutically effective amount of the formulation of claim 1 to treat a patient undergoing orthopedic procedures, dental procedures, implant surgery, joint replacement, bone grafting, bone cosmetic surgery, fracture healing, nonunion healing, delayed union healing and facial reconstruction, comprising administering a dose of said formulation to said patient effective to increase bone density.

22. A sterile liquid formulation that has an absolute viscosity of about 10 cP or less consisting essentially of:
   (a) an anti-sclerostin immunoglobulin at a concentration of from about 70 mg/mL to about 120 mg/mL, wherein the anti-sclerostin immunoglobulin comprises the amino acid sequences of SEQ ID NO: 86 and SEQ ID NO: 84;
   (b) calcium acetate at a concentration ranging from about 1 mM to about 20 mM;
   (c) a polyol in an amount ranging from about 4% w/v to about 6% w/v; and
   (d) an acetate buffer, such that the total concentration of acetate in the formulation is from about 30 mM to about 75 mM.

23. The sterile liquid formulation of claim 22, further comprising a surfactant.

24. The sterile liquid formulation of claim 23, wherein the concentration of the surfactant is from 0.004% w/v to about 0.2% w/v.

25. The sterile liquid formulation of claim 23, wherein the surfactant is polysorbate 20.

26. The sterile liquid formulation of claim 23, wherein the concentration of the surfactant is from about 0.004% to about 0.2% w/v.

27. The sterile liquid formulation of claim 22, wherein the polyol is sucrose.

* * * * *